United States Patent
Allen et al.

(10) Patent No.: US 6,537,792 B1
(45) Date of Patent: Mar. 25, 2003

(54) PROTEIN ENGINEERING OF GLUCOAMYLASE TO INCREASE PH OPTIMUM, SUBSTRATE SPECIFICITY AND THERMOSTABILITY

(75) Inventors: Martin J. Allen, Denver, CO (US); Tsuei-Yun Fang, Ames, IA (US); Yuxing Li, Ames, IA (US); Hsuan-Liang Liu, Ames, IA (US); Hsiu-Mei Chen, Taipei (TW); Pedro Coutinho, Angers (FR); Richard Honzatko, Ames, IA (US); Clark Ford, Ames, IA (US)

(73) Assignee: Iowa State University, Ames, IA (US)

( * ) Notice: Subject to any disclaimer, the term of this patent is extended or adjusted under 35 U.S.C. 154(b) by 0 days.

(21) Appl. No.: 09/236,063

(22) Filed: Jan. 22, 1999

Related U.S. Application Data

(63) Continuation-in-part of application No. PCT/US97/12983, filed on Jul. 24, 1997.
(60) Provisional application No. 60/022,578, filed on Jul. 24, 1996, and provisional application No. 60/023,077, filed on Aug. 2, 1996.

(51) Int. Cl.[7] .............................. C12N 9/24; C12N 9/00
(52) U.S. Cl. ...................... 435/200; 435/183; 435/440; 530/350
(58) Field of Search ................................ 435/183, 200, 435/440; 530/350

(56) References Cited

PUBLICATIONS

Li et al., Genetic Construction and Biochemical Analysis of Thermostability Mutants of Glucoamylase from *Aspergillus awamori*, Dissertation Abstracts vol. 57/11–B p. 6761, 1996.*
Fierobe et al., Mutational Modulation of Substrate Bond––Type Specificity and Thermostability of Glucoamylase from *Aspergillus* awamori by Replacement with Short Homologue Active Site Sequences and Thiol/Disulfide Engineering, Biochemistry 35:8696–8704, 19.*
Ackers, G.K. and Smith, F.R. (1985) *Annu. Rev. Biochem.*, 54, 597–629.
Allen, M., Coutinho, P.M. and Ford, C. (1998) *Protein Eng.*, accepted for publication.
Carter, P.J. Winter, G., Wilkinson, A.J. and Fersht, A.R. (1984) *Cell*, 38, 835–840.
Carter, P., Nilsson, B. Burnier, J.P., Burdick, D. and Wells, J.A. (1989) *Proteins: Struct. Funct. Genet.*, 6, 240–248.
Corn Annual (1998) Corn Refiners Association, Inc., Washington, D.C.
Coutinho, P.M. (1996) Ph.D. Dissertation, Iowa State University, Ames, Ia.
Coutinho, P.M. and Reilly, P.J. (1997) *Proteins: Struct. Funct Genet.*, 29, 334–347.
Cunningham, B.C. and Wells, J.A. (1987) *Protein Eng.*, 1, 319–325.
Fang, T.–Y and Ford, C. (1998) *Protein Eng.*, 11, 383–388.
Fang, T.–Y., Coutinho, P.M. Reilly, P.J. and Ford, C. (1988a) *Protein Eng.*, 11, 119–126.
Fang, T.–Y., Honzatko, R.B., Reilly, P.J. and Ford, C. (1998b) *Protein Eng.*, 11, 127–133.
Frandsen, T.P., Christensen, T., Stoffer, B. Lehmbeck, J., Dupont, C., Honzatko, R.B. and Svensson, B. (1995) *Biochemistry*, 34, 10162–10169.
Frandsen, T.P., Stoffer, B., Palcic, M.M. Hof, S. and Svensson, B. (1996) *J. Mol. Biol.*, 263, 79–89.
Hecht, M.H., Sturtevant, J.M. and Sauer, R.T. (1986) *Proteins: Struct. Funct. Genet.*, 1, 43–46.
Hehre, E.J., Okada, G. and Genghof, D.S. (1969) *Arch. Biochem. Biophys.*, 135, 74–89.
Hiromi, K., Kawai, M. and Ono, S. (1966b) *J. Biochem.*, 59, 476–480.
Kraulis, P.J. (1991) *J. Appl. Crystallogr.* 34, 946–950.
Li, Y., Reilly, P.J. and Ford, C (1997) *Protein Eng.*, 10, 1199–1204.
Li, Y., Coutinho, P.M. and Ford, C. (1998) *Protein Eng.*, accepted for publication.
Liao, H. McKenzie, T. and Hageman, R. (1986) *Proc. Natl. Acad Sci. U.S.A.*, 83, 576–580.
Liu, H.–L., Coutinho, P.M., Ford, C. and Reilly, P.J. (1998) *Protein Eng.*, 11, 389–398.
Natarajan, S. and Sierks, M.R. (1996) *Biochemistry*, 35, 15269–15279.
Nikolov, Z.L., Meagher, M.M. and Reilly, P.J. (1989) *Biotechnol. Bioeng.*, 34, 694–704.

(List continued on next page.)

*Primary Examiner*—Rebecca E. Prouty
*Assistant Examiner*—Richard Hutson
(74) *Attorney, Agent, or Firm*—Kohn & Associates

(57) ABSTRACT

A fungal glucoamylase including a mutation pair Asn20Cys coupled with Ala27Cys forming a disulfide bond between the two members of the pair. The mutation provides increased thermal stability and reduced isomaltose formation to the enzyme. A fungal glucoamylase including a 311-314Loop mutation wherein reduced isomaltose formation is provided by the mutation is also provided. A fungal glucoamylase including a mutation Ser411Ala wherein increased pH optimum and reduced isomaltose formation is provided by the mutation is also provided. Combinations of the mutations in engineered glucoamylases are also provided as are combinations with other glucoamylase mutations that provide increased thermal stability, increased pH optimum and reduced isomaltose froamtion for cumulative improvements in the engineered glucoamylases. Also provided is a fungal glucoamylase including a mutation of Ser30Pro coupled with at least two stabilizing mutations forming a disulfide bond between the two stabilizing members. A fungal glucoamylase including a Ser30Pro/Gly137Ala/311-314 Loop is provided. A fungal glucoamylase including a mutation Ser30Pro/Glu137Ala/Ser411Ala is also provided.

10 Claims, 16 Drawing Sheets

OTHER PUBLICATIONS

O'Rourke, T., Bentley, I.S. and Williams, E.C. (1996) Godfrey, T. and West, S. (eds). *Industrial Enzymology*, Secton edition. Stockton Press, New York.

Pantoiiano, M.W., Whitlow, M., Wood, J.F., Dodd, S.W., Hardman, K.D., Rollence, M.L. and Bryan, P.N. (1989) *Biochemistry*, 28, 7205–7213.

Pazur, J.H. and Okada, S. (1967) *Charbohydr. Res.*, 4, 371–379.

Pazur, J.H. Cepure, A., Okada, S. and Forsberg, L.S. (1977) *Carbohydr. Res.*, 58, 193–202.

Przybyt, M. and Sugier, H. (1988) *Starch/Starke*, 40, 171–174.

Russell, A.J. and Fersht, A.R. (1987) *Nature*, 328, 496–500.

Schimmel, P.R. and Flory, P.J. (1968) *J. Mol. Biiol.*, 34, 105–120.

Scrutton, N.S., Berry A. and Perham, R.N. (1990) *Nature*, 343, 38–43.

Shein, C.H. (1990) *Bio–Technology*, 8, 308–317.

Sinitsyn, A.P. Klibanov, A.M., Klesov, A.A. and Martiek, K. (1978) *Prikl, Biokhim. Mikrobiol.*, 14, 236–243.

Stoffer, B.B., Dupont, C., Frandsen, T.P., Lehmbeck, J. and Svensson, B. (1997) *Protein Eng.*, 10, 81–87.

Svensson, B. Brandsen, T.P., Matsui, I., Juge, N., Fierobe, H.–P., Stoffer, B. and Rodenburg, K.W. (1995) *Carbohydrate Bioengineering*, Petersen, S.B., Svensson, B. and Pedersen, S., eds., Elsevier, Amsterdam, pp. 125–145.

Teague, W.M. and Brumm, P.J. (1992) *Starch Hydrolysis Products: Woldwide Technology, Production, and Applications*, Schenck, F.W. and Hebeda, R.E., eds., VCH, New York, p. 45–77.

Watanabe, T. Kawamura, S., Sasaki, S. and Matsuda, K. (1969a) *Starke*, 21, 18–21.

Watanabe, T., Kawamura, S., Sasaki, S. and Matsuda, K. (1969b) *Starke*, 21, 44–47.

Wells, J.A., Cunningham, B.C., Graycar, T.P. and Estell, D.A. (1987a) *Proc. Natl, Acad. Sci. U.S.A.*, 84, 1219–1223.

\* cited by examiner

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 616 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: Aspergillus (xi) SEQUENCE DESCRIPTION: SEQ ID NO:1:

```
Ala Thr Leu Asp Ser Trp Leu Ser Asn Glu Ala Thr Val Ala Arg Thr
 1               5                  10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Leu Lys Thr Leu Val
    50                  55                  60

Asp Leu Phe Arg Asn Gly Asp Thr Ser Leu Leu Ser Thr Ile Glu Asn
 65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110

Glu Thr Ala Tyr Thr Gly Ser Trp Gly Arg Pro Gln Arg Asp Gly Pro
            115                 120                 125

Ala Leu Arg Ala Thr Ala Met Ile Gly Phe Gly Gln Trp Leu Leu Asp
        130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
            180                 185                 190

His Arg Ala Leu Val Glu Gly Ser Ala Phe Ala Thr Ala Val Gly Ser
        195                 200                 205

Ser Cys Ser Trp Cys Asp Ser Gln Ala Pro Glu Ile Leu Cys Tyr Leu
    210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
            260                 265                 270

Arg Ala Leu Ala Asn His Lys Glu Val Val Asp Ser Phe Arg Ser Ile
        275                 280                 285

Tyr Thr Leu Asn Asp Gly Leu Ser Asp Ser Glu Ala Val Ala Val Gly
    290                 295                 300

Arg Tyr Pro Glu Asp Thr Tyr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
                325                 330                 335

Lys Gln Gly Ser Leu Glu Val Thr Asp Val Ser Leu Asp Phe Phe Lys
            340                 345                 350

Ala Leu Tyr Ser Asp Ala Ala Thr Gly Thr Tyr Ser Ser Ser Ser Ser
        355                 360                 365

Thr Tyr Ser Ser Ile Val Asp Ala Val Lys Thr Phe Ala Asp Gly Phe
    370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415
```

```
Trp Ser Tyr Ala Ala Leu Leu Thr Ala Asn Asn Arg Arg Asn Ser Val
            420                 425                 430
Val Pro Ala Ser Trp Gly Glu Thr Ser Ala Ser Ser Val Pro Gly Thr
        435                 440                 445
Cys Ala Ala Thr Ser Ala Ile Gly Thr Tyr Ser Ser Val Thr Val Thr
    450                 455                 460
Ser Trp Pro Ser Ile Val Ala Thr Gly Gly Thr Thr Thr Thr Ala Thr
465                 470                 475                 480
Pro Thr Gly Ser Gly Ser Val Ser Thr Ser Lys Thr Thr Ala Thr
                485                 490                 495
Ala Ser Lys Thr Ser Thr Ser Thr Ser Ser Thr Ser Cys Thr Thr Pro
            500                 505                 510
Thr Ala Val Ala Val Thr Phe Asp Leu Thr Ala Thr Thr Thr Tyr Gly
        515                 520                 525
Glu Asn Ile Tyr Leu Val Gly Ser Ile Ser Gln Leu Gly Asp Trp Glu
    530                 535                 540
Thr Ser Asp Gly Ile Ala Leu Ser Ala Asp Lys Tyr Thr Ser Ser Asp
545                 550                 555                 560
Pro Leu Trp Tyr Val Thr Val Thr Leu Pro Ala Gly Glu Ser Phe Glu
                565                 570                 575
Tyr Lys Phe Ile Arg Ile Glu Ser Asp Asp Ser Val Glu Trp Glu Ser
            580                 585                 590
Asp Pro Asn Arg Glu Tyr Thr Val Pro Gln Ala Cys Gly Thr Ser Thr
        595                 600                 605
Ala Thr Val Thr Asp Thr Trp Arg
    610                 615

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asn Gly Asn Gly Asn Ser Gln
1               5

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:3:

CAGAGTCCGC GCCCGGCACC CAAGCACCGT C                              31

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
```

(D) TOPOLOGY: linear (ii) MOLECULE TYPE: other nucleic acid
           (A) DESCRIPTION: /desc = "PRIMER"

(xi) SEQUENCE DESCRIPTION: SEQ ID NO:4:

AAGTCCAGCG ACACAGGTGT GACCTCCAAC GAC                                     33

(2) INFORMATION FOR SEQ ID NO:5:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: other nucleic acid
           (A) DESCRIPTION: /desc = "PRIMER"

(xi) SEQUENCE DESCRIPTION: SEQ ID NO:5:

CGAGCGGAAA GCTGCGGGCC ATCAGACTTG TC                                      32

(2) INFORMATION FOR SEQ ID NO:6:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: other nucleic acid
           (A) DESCRIPTION: /desc = "PRIMER"

(xi) SEQUENCE DESCRIPTION: SEQ ID NO:6:

CGTACTGCCA TCCTGTGTAA CATCGGGGCG GA                                      32

(2) INFORMATION FOR SEQ ID NO:7:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
           (A) DESCRIPTION: /desc = "PRIMER"

(xi) SEQUENCE DESCRIPTION: SEQ ID NO:7:

ATCGGGGCGG ACGGTTGTTG GGTGTCGGGC GCG                                     33

(2) INFORMATION FOR SEQ ID NO:8:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: other nucleic acid
           (A) DESCRIPTION: /desc = "PRIMER"

(xi) SEQUENCE DESCRIPTION: SEQ ID NO:8:

GAGTATCGTG TGTACTGGCG GCACC                                              25

(2) INFORMATION FOR SEQ ID NO:9:

(i) SEQUENCE CHARACTERISTICS:
          (A) LENGTH: 30 base pairs
          (B) TYPE: nucleic acid

```
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:9:

GGTCTCGGTG AGCCCAGGTT CAATGTCGAT                              30

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:10:

GGTCTCGGTG AGCCCATGTT CAATGTCGAT                              30

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:11:

GAGGACACGT ACTGGAACGG CAACCCG                                 27

(2) INFORMATION FOR SEQ ID NO:12:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:12:

TACCCTGAGG ACACGTACAA CGGCAACGGC AACTCGCAGG GCAACCCGTG G TTCCTGTGC    60
```

US 6,537,792 B1

PROTEIN ENGINEERING OF GLUCOAMYLASE TO INCREASE PH OPTIMUM, SUBSTRATE SPECIFICITY AND THERMOSTABILITY

This application is a continuation-in-part of PCT/US97/12983, filed Jul. 24, 1997 which claims the benefit of U.S. Provisional No. 60/022,578 filed Jul. 24, 1996, and No. 60/023,077 filed Aug. 2, 1996.

FIELD OF THE INVENTION

The field of the invention relates to mutations to produce a fungal glucoamylase enzyme that is more selective for the production of glucose rather than the α-1,6 linked disaccharide isomaltose, is more thermostable, and has increased pH optimum and produces increased amounts of glucose compared to wildtype enzymes.

BACKGROUND OF THE INVENTION

Glucoamylase (EC 3.2.1.3) is a carbohydrase. Discovered in 1951, it is an exo-hydrolase that cleaves D-glucose from the nonreducing ends of maltooligosaccharides, attacking α-(1,4)-, and at a much slower rate, α-(1,6)-glucosidic bonds. It is one of more than one hundred carbohydrates (EC 3.2.1) that cleave O-glycosidic bonds of either α- or β-configuration. The functional and structural relatedness of these enzymes is reflected in the presence of at least three discrete regions of sequence homology between glucoamylase and several α-amylases, α-glucosidases, and transglucanosylases [Svensson, 1988], and a similar domain structure to carbohydrates that attack insoluble substrates [Knowles et al., 1987; Svensson et al., 1989)]. *Aspergillus awamori* glucoamylase (1,4-α-D-glucan glucohydrolase; EC 3.2.1.3) is one of the most important of the glucoamylases.

Glucoamylase is primarily used in industry for the production of high-fructose corn sweeteners in a process that involves 1) α-amylase to hydrolyze starch to maltooligosaccharides of moderate length (dextrin); 2) Glucoamylase to hydrolyze dextrin to glucose; and 3) glucose isomerase to convert glucose to fructose. Corn sweeteners have captured over 50% of the U. S. sweetener market, and the three enzymes used to make them are among the enzymes made in highest volume. In addition, glucose produced by glucoamylase can be crystallized or used in fermentation to produce organic products such as citric acid, ascorbic acid, lysine, glutamic acid or ethanol for beverages and fuel. Approximately 12% of the country's corn production is processed with glucoamylase. Although glucoamylase has been successfully used for many years, it would be a more attractive product if it produced higher amounts of glucose instead of disaccharides, if it were more stable, and if it could be used in the same vessel with glucose isomerase.

Glucoamylase does not give 100% yield of glucose from dextrin because it makes various di- and trisaccharides, especially isomaltose and isomaltotriose, from glucose [Nikolov et al., 1989]. These products, formed at high substrate concentrations, result from the ability of glucoamylase to form α-(1,6)-glucosidic bonds. Glucoamylase is not as thermostable as either α-amylase or glucose isomerase. The optimum pH of GA (pH4–4.5) is lower than that of αamylase (pH5.5–6.5) and glucose isomerase (pH7–8). Therefore glucoamylase hydrolysis must be done separately from the other enzymatic reactions in a different vessel and at lower temperatures, causing higher capital costs.

Glucoamylase from the filamentous fungus *Aspergillus niger* is the most widely used glucoamylase, and its biochemical properties have been extensively characterized. This enzyme is found mainly in two forms, GAI (616 amino acids; referred to as AA hereinafter) and GAII (512 AA), differing by the presence in GAI of a 104-AA C-terminal domain required for adsorption to native starch granules [Svensson et al., 1982; Svensson et al., 1989]. Both forms have a catalytic domain (AA1–440) followed by a Ser/Thr-rich, highly O-glycosylated region (AA441–512) [Gunnarsson et al., 1984]. The first thirty residues of this region are included in the three-dimensional structure of the enzyme [Aleshin et al., 1994; 1996; Stoffer et al., 1995]; they wrap around the catalytic domain like a belt. There is strong AA sequence homology among fungal glucoamylase's in four distinct regions of the catalytic domain that correspond to the loops that form the substrate binding site [Itoh et al., 1987]. In *A. niger* glucoamylase these regions are AA35–59, AA104–134, AA162–196, and AA300–320. The second and third regions partially or completely overlap the three regions of homology to α-amylases [Svensson, 1988]. In addition, the raw starch binding domain (AA512–616) has high homology to similar domains from several starch-degrading enzymes [Svensson et al., 1989].

Kinetic analysis showed that the substrate binding site is composed of up to seven subsites [Savel'ev et al., 1982] with hydrolysis occurring between subsites 1 and 2. The $pK_a$'s of hydrolysis, 2.75 and 5.55 [Savel'ev and Firsov, 1982], suggest that carboxylic acid residues at subsites 1 and 2 provide the catalytic acid and base for hydrolysis. Chemical modification experiments showed that three highly conserved residues, Asp176, Glu179, and Glu180, are protected and are in the active site, suggesting that one or more of them are the possible catalytic residues [Svensson et al., 1990]. Chemical modification experiments also indicated that the highly conserved residue Trp120 is essential, and is located in subsite 4 [Clarke and Svensson, 1984]. Trp120 is homologous to Trp83 of *Aspergillus oyzae* α-amylase [Clarke and Svensson, 1984], which is also located in the active site of that enzyme [Matsuura et al., 1984]. Site directed mutagenesis studies have indicated that Glu179 is the catalytic acid residue, while Glu400 is the catalytic base residue [Frandse et al, 1994; Harris et al, 1993; Sierks et al, 1990]

Glucoamylases from *A. niger* [Svensson et al., 1983; Boel et al., 1984] and *Aspergillus awamori* [Nunberg et al., 1984] have been cloned and sequenced, and have identical primary structures. Innis et al. [1985] and more recently Cole et al. [1988] have developed vectors (pGAC9 and pPM18, respectively) for glucoamylase expression in yeast, allowing convenient manipulation and testing of glucoamylase mutants.

SUMMARY OF THE INVENTION

According to the present invention, a fungal glucoamylase (1,4-α-D-glucan glucohydrolase; EC 3.2.1) with decreased thermal inactivation (increased thermostability) and reduced isomaltose formation provided by the mutation Asn20Cys coupled with Ala27Cys forming a disulfide bond between the two is provided. Cumulative thermostability is also provided for GA by including the mutation Asn20Cys coupled with Ala27Cys and at least one mutation from Table 13. An engineered GA including Ser30Pro, Gly137Ala, and Asn20Cys coupled with Ala27Cys provides even more thermostability. Cumulative thermostability is also provided for GA by including the mutation Asn20Cys coupled with Ala27Cys and at least two mutations from Table 13.

The present invention also provides a fungal glucoamylase with reduced isomaltose formation including an Asn20Cys coupled with Ala27Cys mutation (S-S mutation) and at least one mutation selected from Table 14. In an embodiment Asn20Cys coupled with Ala27Cys mutation and a 311-314Loop (also referred to as 300Loop) mutation are included in an engineered GA. In a further preferred embodiment the engineered glucoamylase with reduced isomaltose formation includes Asn20Cys coupled with Ala27Cys mutations Ser30Pro and Gly137Ala.

The present invention also provides engineered fungal glucoamylase including a 311-314Loop mutation whereby reduced isomaltose formation is provided by the mutation.

In a further embodiment fungal glucoamylase including a 311-314Loop mutation and at least one mutation from Table 14 are prepared whereby cumulative reduced isomaltose formation is provided by the additional mutation.

The present invention provides a fungal glucoamylase including a mutation Ser411Ala whereby increased pH optimum and reduced isomaltose formation is provided by the mutation. In an embodiment the Ser411Ala mutation is combined with at least one mutation from Table 15 whereby cumulative increased pH optimum is provided by the mutations. In an embodiment the Ser411Ala mutation is combined with at least one mutation from Table 14 whereby cumulative reduced isomaltose formation is provided by the mutations.

In a further embodiment an engineered fungal glucoamylase includes a mutation Ser411Ala and a mutation pair Asn20Cys coupled with Ala27Cys forming a disulfide bond between the two members of the pair whereby increased thermal stability, increased pH optimum and reduced isomaltose formation are provided by the mutations.

In a still further embodiment a fungal glucoamylase is engineered to include a Ser411Ala mutation and a mutation pair Asn20Cys coupled with Ala27Cys forming a disulfide bond between the two members of the pair and a 311-314Loop mutation whereby increased thermal stability, increased pH optimum and reduced isomaltose formation are provided by the mutations.

The present invention provides a method to obtain a fungal glucoamylase with reduced isomaltose formation by designing mutations to decrease the α-(1,6)-glucosidic linkage affinity of GA.

The present invention also provides a method to obtain a fungal glucoamylase with decreased thermal inactivation by designing mutations to decrease the enzyme's conformational entropy of unfolding and/or increase stability of α-helices, increase disulfide bonds, hydrogen bonding, electrostatic interactions, hydrophic interactions, Vanderwalls interactions and packing compactness.

The present invention also provides a fungal glucoamylase with increased pH optimum including changing the polarity, charge distribution and hydrogen bonding in the microenvironment of the catalytic base Glu400.

The present invention also provides a method of genetically engineering glucoamylase carrying at least two cumulatively additive mutations. Individual mutations are generated by site-directed mutagenesis. These individual mutations are screened and those selected which show increased pH optimum and which show decreased irreversible thermal inactivation rates or reduced isomaltose formation. Site directed mutagenesis is then performed to produce enzymes carrying at least two of the isolated selected mutations. Finally the engineered enzymes are screened for cumulatively additive effects of the mutations on thermal stabilizing or reduced isomaltose formation by the produced enzymes carrying at least two of the isolated selected mutations. Alternatively, the engineered enzyme is screened for cumulatively additive effects of both of the mutations on pH optimum, thermostability and/or reduced isomaltose formation by the produced enzymes carrying at least two of the isolated selected mutations.

Vectors for each of the mutations and mutation combinations are also provided by the present invention as well as host cells transformed by the vectors. Also provided is a fungal glucoamylase including a mutation of Ser30Pro coupled with at least two stabilizng mutations forming a disulfide bond between the two stabilizing members. A fungal glucoamylase including a Ser30Pro/Gly137Ala/311-314 Loop is provided. A fungal glucoamylase including a mutation Ser30Pro/Glu137Ala/Ser411Ala is also provided.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5A Wildtype (●), S30P (■), G137A (_) S30P/G137A (□); FIG. 5B Wildtype (●), S30P (■), S-S (hexagon), S-S/S30P (filed circle with empty center); FIG. 5C Wildtype (●), S30P/G137A (□), S-S/S30P (filed circle with empty center), S-S/S30P/G137A (▼)

maltodextrin in 0.05M sodium acetate buffer at pH4.4 with 0.02% sodium azide for 12 days.

Figure 10:
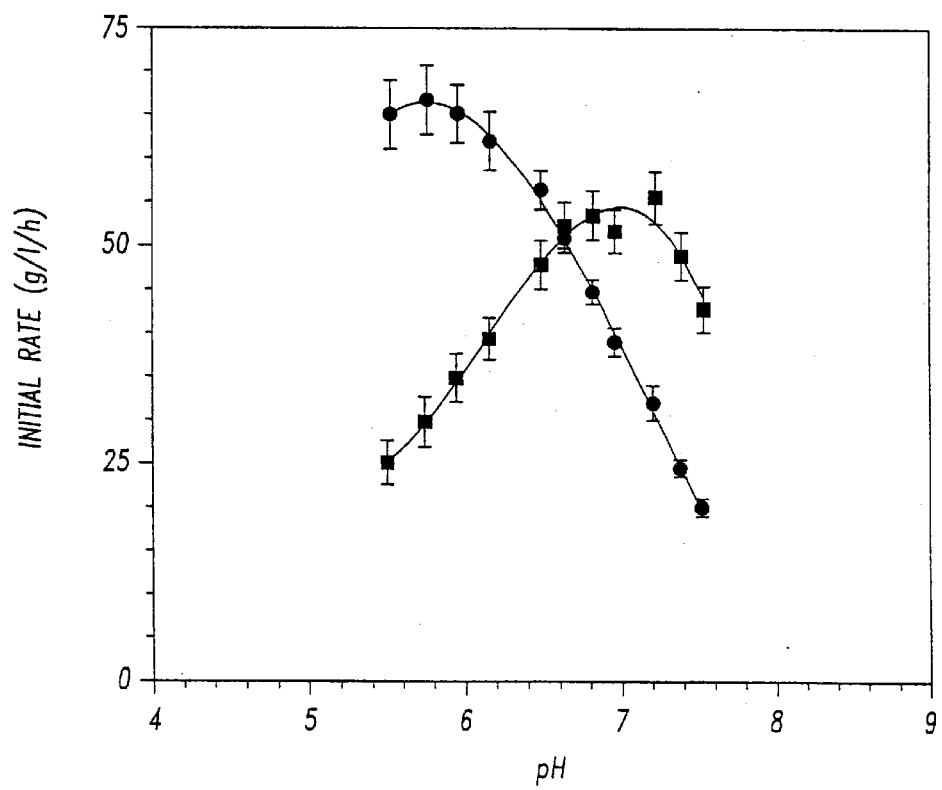

FIG. 10 is a graph showing the initial rates of glucose production by wildtype (●) and S411A (■) glucoamylases during DE 10 maltodextrin hydrolysis at different pH values. Hydrolysis was performed at 36° C. with 28% (w/v) maltodextrin in 25 mM citrate-phosphate buffer at indicated pHs with 0.02% sodium azide for 4 days.

Figure 11:
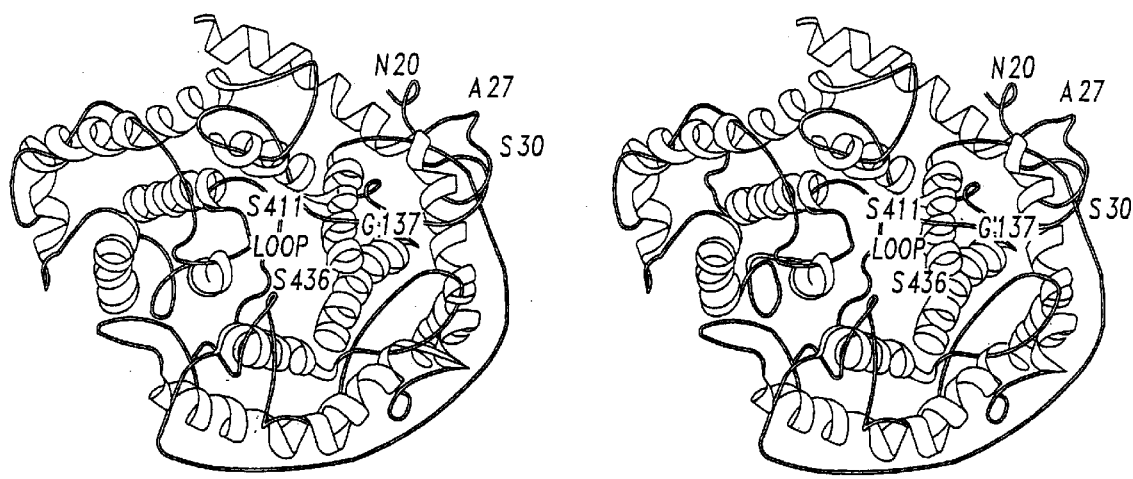

FIG. 11 is a three-dimensional view of A. awamori/A. niger GA, showing mutated residues.

Figure 12A:
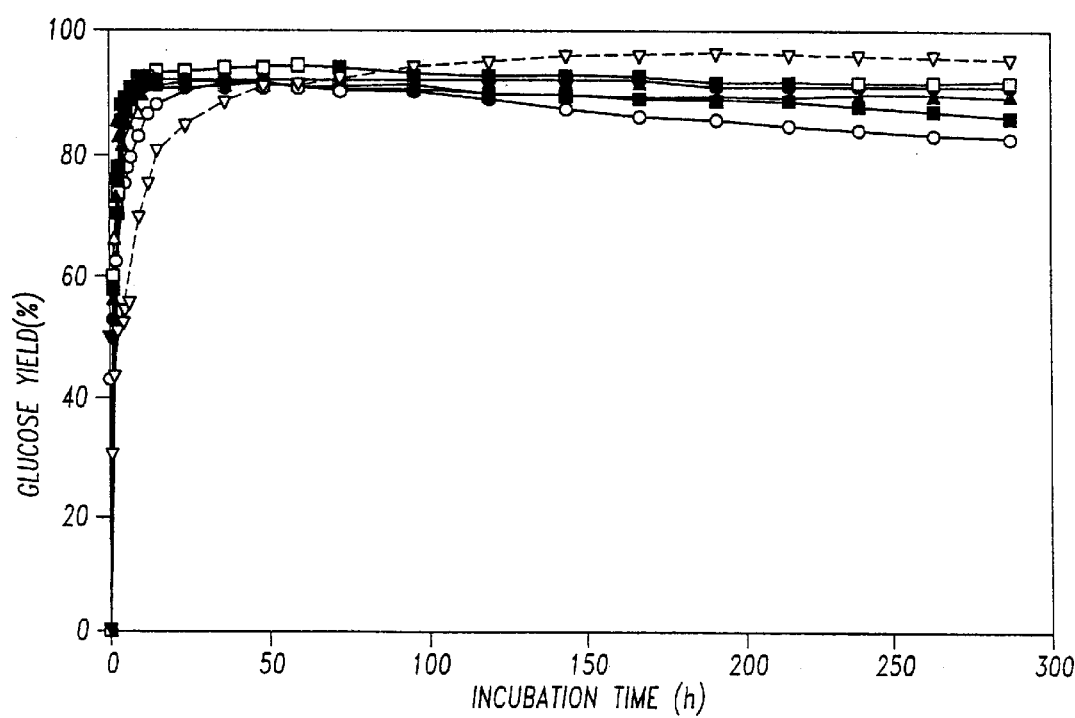
Figure 12B:
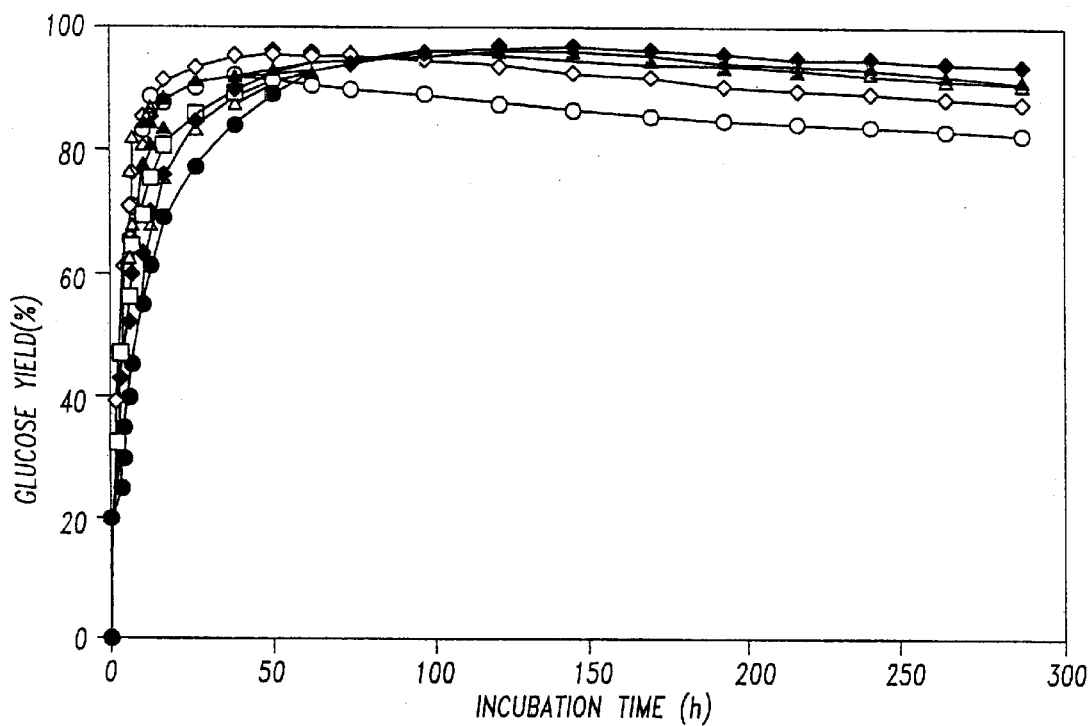

FIGS. 12A and 12B are graphs showing the glucose formation during the incubation of 30% (w/v) DE 10 maltodextrin with 1.98 μM GA in 0.05 M naOAc buffer, pH 4.4 at 55° C.; (A: wild-type (○, _), SS/Ser30→Pro (Δ, _ _), SS/Gly137→Ala (□, _ _ _), SS/Ser411→Ala (∇, _ _ _), SS/Ser436→Pro (●, . . . ), Ser30→Pro/Gly137→Ala (▲, —._._), Gly137→Ala/Ser436→Pro (■, _.._), SS/Ser30→Pro/Gly137→Ala (▼, _); (b): wild-type (○, _), SS/311-314 Loop (▼, _ _), SS/Ser411→Ala (∇, _ _ _), Ser30→Pro/311-314 Loop (▲, _ _ _ _); Ser30→Pro/Ser411→Ala (Δ, . . . ), Gly137→Ala/311-314 Loop (■, _._._), Gly137→Ala/Ser411→Ala (□, _.._._), 311-314 Loop/Ser411→Ala (●, _), Ser30→Pro/Gly137→Ala/311-314 Loop (♦, _ _) and Ser30→Pro/Gly137→Ala/Ser411→Ala (♦, _ _ _).

Figure 13A:
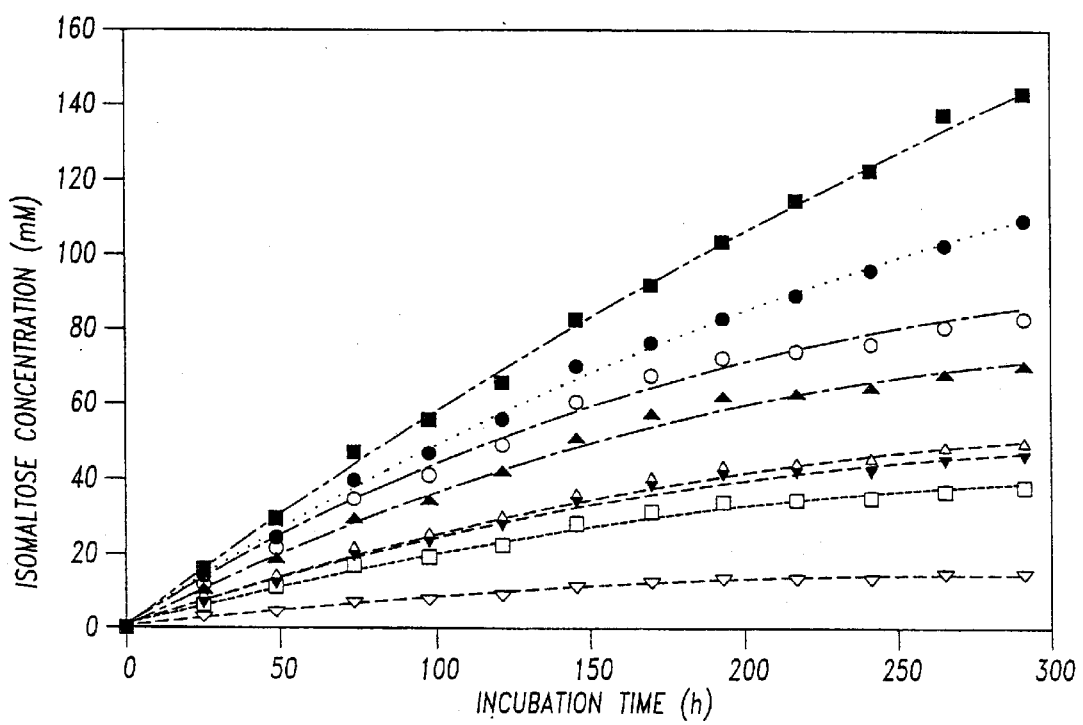
Figure 13B:
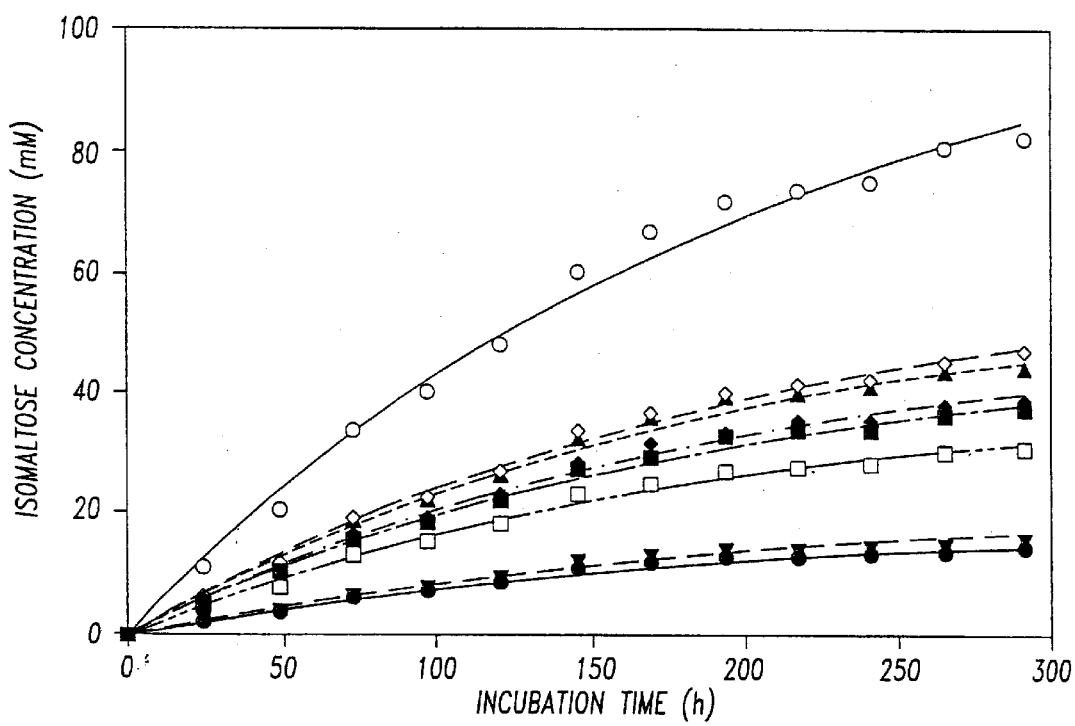

FIGS. 13A and 13B are graphs showing the formation of iG$_2$ for 30% (w/v) glucose condensation with wild-type and mutated GAs. Conditions as in FIG. 2. (A): Symbols as in FIG. 2(a); (B): Symbols as in FIG. 2(b).

Figure 14A:
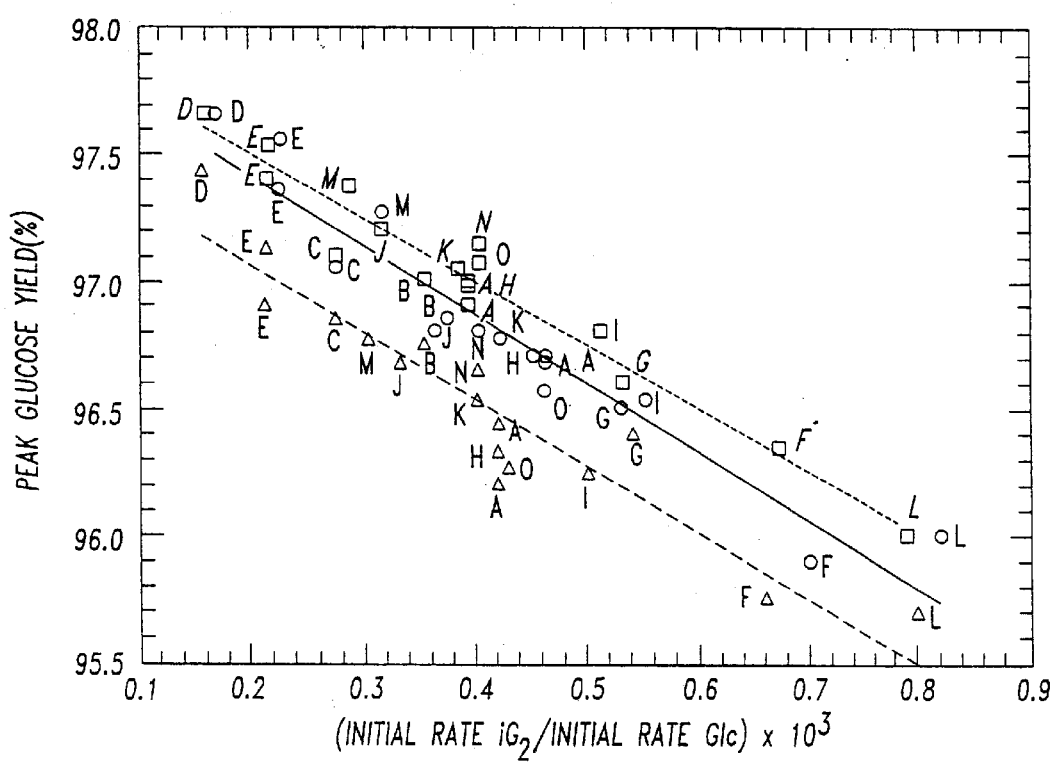

FIGS. 14A, B, and C are graphs showing the peak glucose yields vs. initial rate ratios (×10$^3$) with 1.98 μM GA in 0.05 M NaOAc buffer, pH 4.4 DE 10 (○, _, bold letters); DE 18 (Δ, - - , normal letters), and DE 25 (□, . . . , italicized letters) maltodextrins; (A): wild-type; (B): Ss/Ser30→Pro; (C): SS/Gly137→Ala; (D) : SS/311-314 Loop; (E): SS/Ser411→Ala; (F): SS/Ser436→Pro; (G): Ser30→Pro/Gly137→Ala; (H) Ser30→Pro/311-314 Loop; (I): Ser30→Pro/Ser411→Ala; (J): Gly137→Ala/311-314 Loop; (K) Gly137→Ala/Ser411Ala; (L): Gly137→Ala/Ser436→Pro; (M): 311-314 Loop/Ser411→Ala; (N): SS/Ser30→Pro/Gly137→Ala; (O): Ser30→Pro/Gly137→Ala/311-314 Loop GAs; (A): at 35° C.; (B): at 45° C.; and at (C): and at 55° C.

Figure 15:
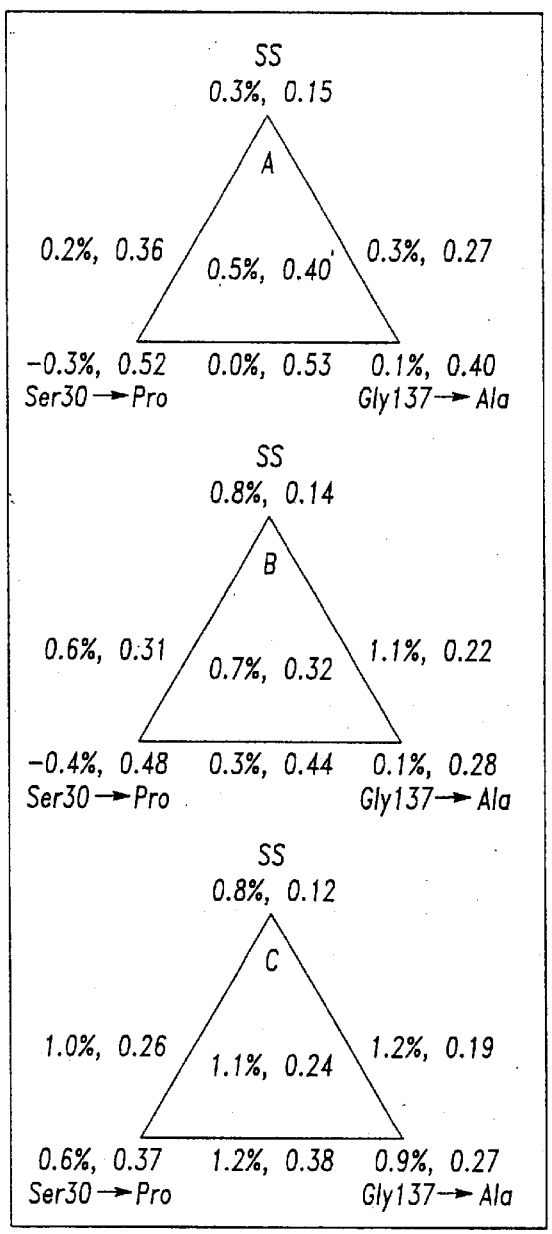

FIG. 15 is a depiction of the cumulative effects of mutatins on GA selectivity for combinations of SS, Ser30→Pro and Gly137→Ala mutations; variations of peak glucose yields from those of wild-type GA and initial rate ratios (×10$^3$) of singly-mutated GAs are at the corners, those of doubly-mutated GAs are at the midpoints of the sides, and those of the triply-mutated GA are in the center; values have been averaged for DE10, 18 and 25 maltodextrins. (a): 35° C.; (b) 45° C.; (c) 55° C.

Figure 16:
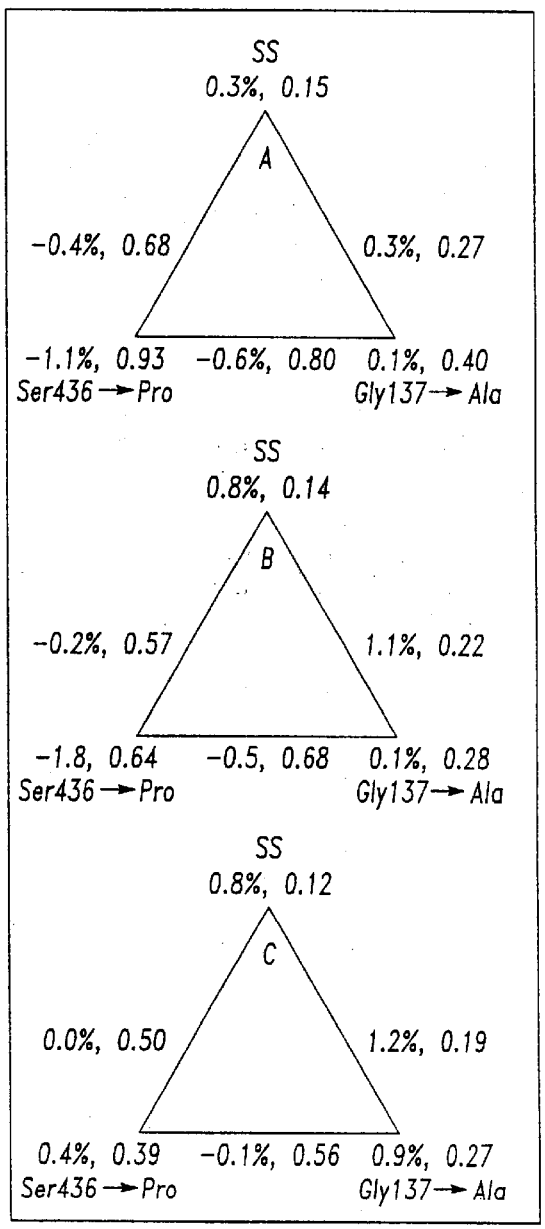

FIG. 16 is a depiction of the cumulative effects of mutations on GA selectivity for combinations of SS, Gly137→AlaAla and Ser436→Pro mutations with notations as in FIG. 15.

Figure 17:
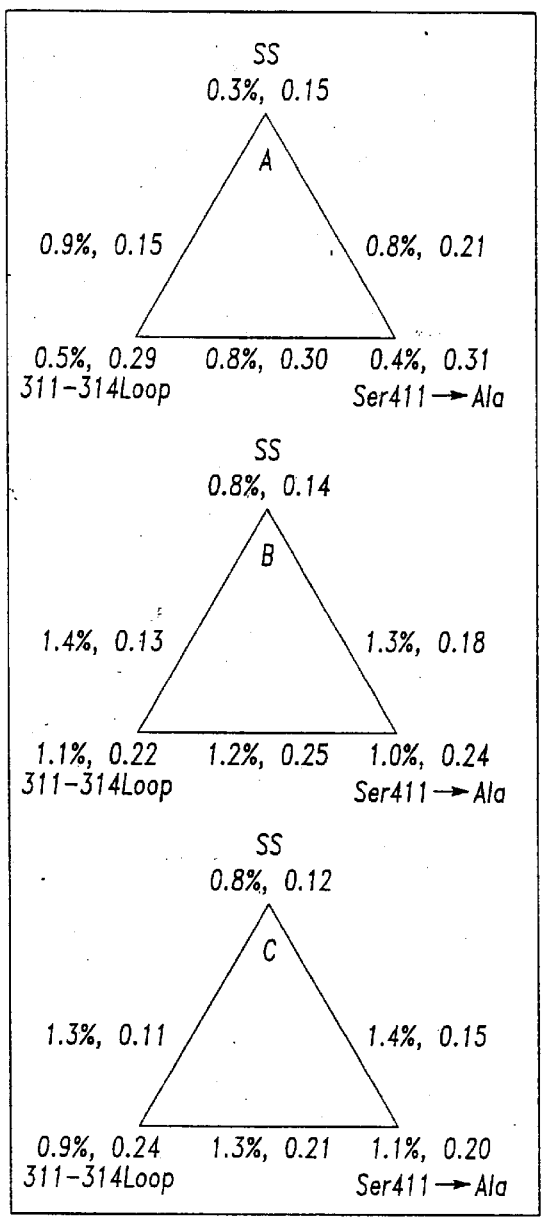

FIG. 17 is a depiction of the cumulative effects of mutations on GA selectivity for combinations of SS, 311-314 Loop and Ser411→Ala mutations with notations as in FIG. 15.

Figure 18:
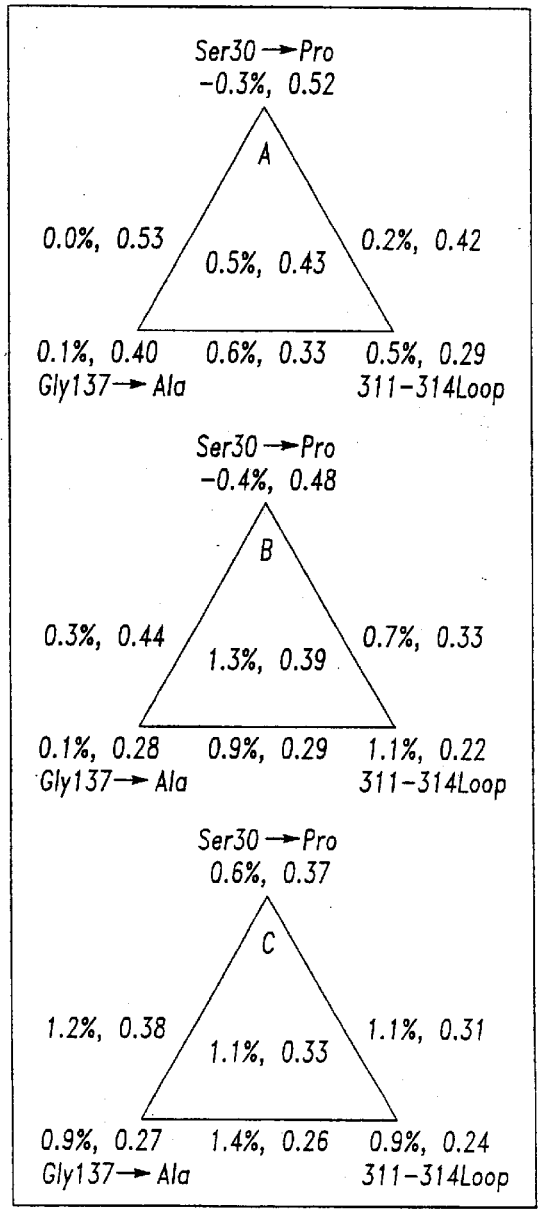

FIG. 18 is a depiction of the cumulative effects of mutations on GA selectivity for combinations of Ser30→Pro, Gly137→Ala and 311-314 Loop mutations, with notations as in FIG. 15.

Figure 19:
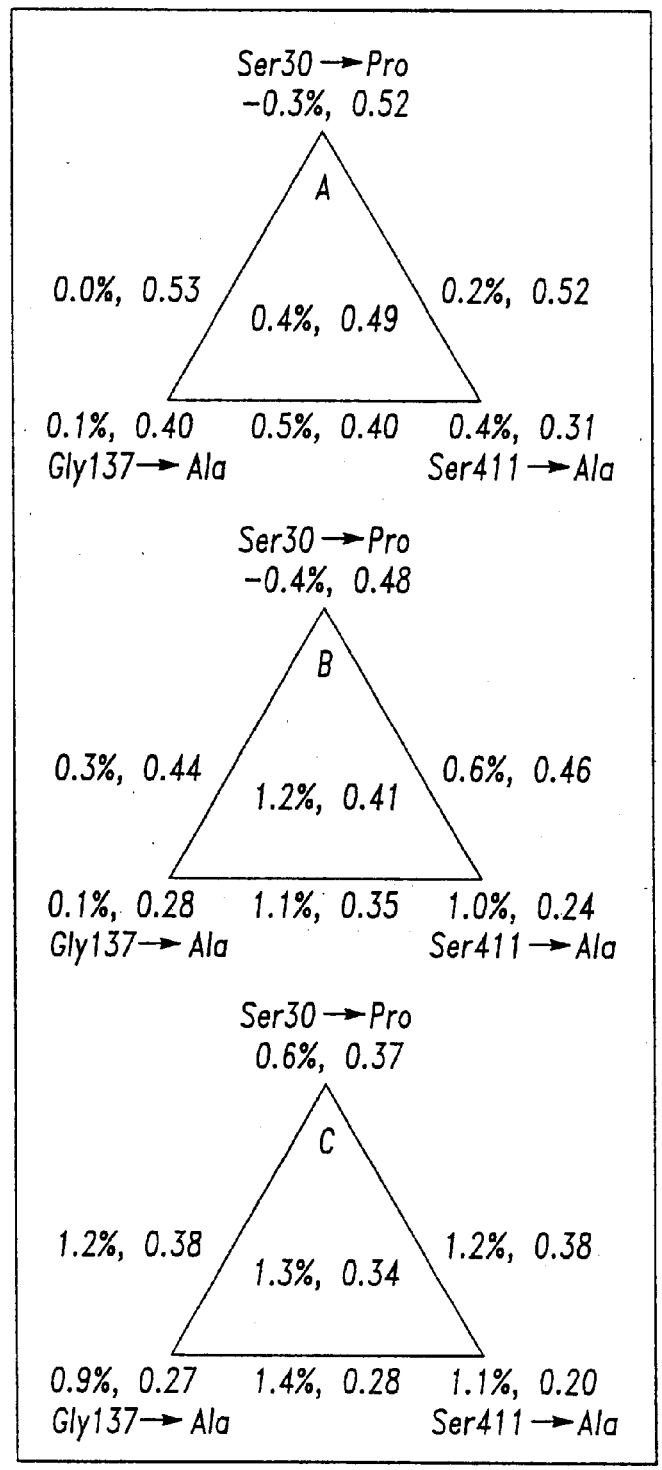

FIG. 19 is a depiction of the cumulative effects of mutations on GA selectivity for combinations of Ser30→Pro, Gly137→Ala and Ser411→Ala mutations with notations as in FIG. 15.

DETAILED DESCRIPTION OF THE PREFERRED EMBODIMENT

The present invention provides mutations for increased thermal stability, increased pH optimum and reduced isomaltose formation in the glucoamylase from fungal species which may provide increased glucose yields compared to wildtype glucoamylase. Predicted structure and known sequences of glucoamylase are conserved among the fungal species [Coutino et al, 1994]. As an exemplar Aspergillus awamori glucoamylase (1,4-α-D-glucan glucohydrolase; EC 3.2.1.3; referred to as GA herein; SEQ ID No:1) is used, but any other fungal species including Aspergillus species glucoamylase can be used. The numbering of the glucoamylase amino acids herein is based on the sequence of the exemplar Aspergillus awamori. Equivalent amino acid residue numbers are determined differently for different fungal species as is known in the art [Coutino et al., 1994].

The present invention provides a fungal glucoamylase with decreased thermal inactivation (increased thermostability) and decreased isomaltose formation provided by engineering the inclusion of a mutation pair Asn20Cys coupled with Ala27Cys which forms a disulfide bond between them (this mutation is abbreviated as Asn20Cys/Ala27Cys or S-S). Additional mutations providing decreased thermal inactivation are set forth in Summary Table 13.

Cumulative thermostability is also provided for GA by including at least two of the mutations in the enzyme as for example including mutations Ser30Pro and Gly137Ala. Another example is to engineer S-S with Asn20Cys/Ala27Cys in the enzyme or to pair Gly137Ala with S-S. Further, combinations of the individual mutations set forth in Table 13, particularly with S-S coupled with Ser30Pro also provide cumulative thermostability. In general two mutation combinations are made but triple mutations can also be constructed. As for example,an engineered GA including the three mutations: Ser30Pro, Gly137Ala, and Asn20Cys/Ala27Cys provides even more thermostability.

By Asn20Cys coupled with Ala27Cys is meant a pair of mutations which is abbreviated as "S-S" or Asn20Cys/Ala27Cys and between which is formed a disulfide bond as described herein in the Examples. In general, this is referred to as a single mutation since both are required to form the disulfide bond.

By cumulative is generally meant the additive (or nearly additive) effects of two or more mutations on the parameter of enzyme activity being measured.

The present invention also provides a fungal glucoamylase with reduced isomaltose formation and increased glucose yield including the Asn20Cys/Ala27Cys mutation (S-S mutation) and at least one mutation selected from Table 14. In an embodiment the Asn20Cys/Ala27Cys mutation and the 311-314Loop (300Loop) are included in GA. In a further preferred embodiment the engineered glucoamylase with reduced isomaltose formation includes Asn20Cys/Ala27Cys and with mutations Ser30Pro and Gly137Ala.

In an embodiment a glucoamylase with the 311–114 loop mutation is constructed to provide reduced isomaltose formation. By the 311-314 Loop mutation is meant an insertional GA mutant with the sequence Tyr311-Tyr312-Asn313-Gly314→Tyr311-Asn-Gly-Asn-Gly-Asn-Ser-Gln-Gly314 (311-314 Loop; SEQ ID No:2).

The present invention provides a fungal glucoamylase including a Ser411Ala mutation whereby increased pH optimum and reduced isomaltose formation is provided by the mutation. In an embodiment the Ser411Ala mutation is combined with at least one mutation from Table 15 whereby cumulative increased pH optimumis provided by the combined mutations. In a further embodiment the Ser411Ala mutation is combined with at least one mutation from Table 14 whereby cumulative reduced isomaltose formation is provided by the mutations.

In a further embodiment an engineered fungal glucoamylase includes a Ser411Ala mutation and the mutation pair Asn20Cys/Ala27Cys forming a disulfide bond between them whereby increased thermal stability, increased pH optimum and reduced isomaltose formation are provided by the mutations.

In a still further embodiment a fungal glucoamylase including a Ser411Ala mutation and a mutation pair Asn20Cys coupled with Ala27Cys forming a disulfide bond between the two members of the pair and a 311-314 Loop mutation whereby increased thermal stability, increased pH optimum and reduced isomaltose formation are provided by the combination of mutations.

The present invention provides a fungal glucoanylase with decreased thermal inactivation (increased thermostability) and decreased isomaltose formation provided by engineering the inclusion of the mutation Ser30Pro combined with two stabilizing mutations Gly137/Ala and Asn20Cys/Ala27Cys, which create a disulfide bond between positions 20 and 27. Additional mutations providing decreased thermal inactivation are set forth in Table 18.

The present invention also provides a fungal glucoamylase including a Ser30Pro/Glu137Ala/311-314 Loop or Ser30Pro/Glu137Ala/Ser411 Ala. Additional mutations providing increased thermostability and increased glucose yield are set forth in Table 16.

Mutations are indicated by the amino acid being replaced followed by the residue number followed by the replacing amino acid. Amino acids are abbreviated either with the three letter code or single letter code. Mutations are generated using site directed mutagenesis as is known in the art. The sequence and residue number are from the Wildtype (WT) or nonmutant enzyme. Biochemical characterization is performed as described herein below and in the Examples. The Examples provide exemplars of the analysis for an individual mutation to determine its characteristics and provide exemplars of analysis for combinations of mutations to determine if the combination provides cumulative effects.

By increased thermostability (or decreased thermal inactivation) is meant that at temperatures between 65° C. and 77.5° C. the mutants are irreversibly inactivated at a decreased rate compared to wildtype.

The present invention provides a method to obtain fungal glucoamylases with decreased thermal inactivation by designing mutations to decrease the rate of irreversible thermal inactivation at temperatures between 65° C. and 77.5° C. compared to wildtype. This is accomplished by designing glucoamylases with decreased thermal inactivation by designing mutations to decrease the enzyme's conformational entropy of unfolding and/or increase stability of α-helices, increase disulfide bonds, hydrogen bonding, electrostatic interactions, hydrophic interactions, Vanderwalls interactions and packing compactness.

Basic mechanisms underlying protein thermostability and factors influencing reversible and irreversible thermal inactivation have been studied extensively [Argos et al., 1979; Klibanov, 1983; Wasserman, 1984; Ahern and Klibanov, 1985]. Factors involved in stabilizing proteins at high temperatures include 1) disulfide bonds, 2) noncovalent bonds such as salt bridges, hydrogen bonding, and hydrophobic interactions, and 3) conformational rigidity [Nosoh and Sekiguchi, 1988]. The causes of irreversible inactivation at high temperatures include 1) aggregation, 2) the formation of incorrect structures, 3) the destruction of disulfide bonds, 4) deamidation (especially of Asn at Asn-Gly sequences), and 5) cleavage of Asp-X peptide linkages. It is apparent that replacement of even one residue can make a large difference in protein thermostability [Matsumura and Aiba, 1985], due to the small increases in free energy (20–30 kJ/mol) usually required to stabilize protein tertiary structures [Nosoh and Sekiguchi, 1988]. Genetic engineering to increase thermostability (or to decrease irreversible thermoinactivation) of enzymes has been successful in several cases [Perry and Wetzel, 1984; Imanaka et al., 1986; Ahearn et al., 1987]. However, the mechanisms that govern thermostability are not fully understood, so that amino acid (AA) replacements that promote thermostability are not accurately predicted [Leatherbarrow and Fersht, 1986; Nosoh and Sekiguchi, 1988; Pakula and Sauer, 1989]. The method of the present invention allows for more accurate prediction.

By increased pH optimum is meant that the enzyme is functional at a higher pH, above that of wildtype.

The present invention also provides a method to design a fungal glucoamylase with increased pH optimum by changing the polarity, charge distribution andhydrogen bonding in the microenvironment of the catalytic base Glu400. For example, mutants S411G and S411A were designed to remove the hydrogen bond between Ser411 and Glu400 (see Example 8).

By increased selectivity is meant that there is decreased isomaltose formation due to decrease in the production of undesirable α-(1,6)-linked byproducts (reversion products) at high glucose concentrations [Lee et al., 1976]. As described above, GA hydrolyzes and synthesizes both α-(1, 4) and α-(1,6) glucosidic bonds. Increasing selectivity indicates that the enzyme synthesizes α1,6 linked products at a lower rate than wildtype as shown by reduced levels of isomaltose formation in condensation reactions with 30% glucose as a substrate compared to wildtype GA. Additionally, improved selectivity may result in increased glucose yields in saccharification reactions using 28% DE 10 maltodextran as a substrate.

The present invention provides a method to obtain a fungal glucoamylase with reduced isomaltose formation by designing mutations to decrease the α- (1,6)-glucosidic linkage affinity of GA. That is mutations are designed in the active site to reduce isomaltose formation due to glucose condensation. The mutations are designed to have decreased ability to synthesize isomaltose while maintaining at least partial wildtype ability to digest α1–4 linked substrates resulting in a lower ratio of isomaltose formation to glucose formation than wildtype. These mutations are made at positions that are not completely conserved based on homology analysis.

Kinetic studies have indicated that there are five to seven glucosyl binding subsites, and the catalytic site is located between subsites 1 and 2 [Hiromi et al., 1973, Hiromi et al., 1983, Meagher et al., 1989, Tanaka et al., 1983]. The solved three-dimensional structure of the catalytic domain of glucoamylase from *Aspergillus awamori* var X100, which has about 95% homology with the corresponding regions of GAs from *Aspergillus awamori* and *Aspergillus niger* [Coutinho & Reilly, 1994], contains thirteen alpha-helices, twelve of which are arranged in pairs forming an alpha/alpha barrel [Aleshin et al., 1992, Aleshin et al., 1994]. The active site is located in the cavity of the barrel center. In addition, homology analysis of thirteen amino acid sequences of glucoamylases showed that five conserved regions define the active site [Coutinho & Reilly, 1994]. The mechanism of GA catalysis involves two carboxyl groups [Hiromi et al., 1966], Glu179 and Glu400 (in *Aspergillus awamori* or *Aspergillus niger*) [Frandsen et al., 1994, Harris et al., 1993, Sierks et al., 1990]. Glu179 protonates the oxygen in the glycosidic linkage, acting as general acid acatalyst, and Glu400 activates water (Wat500) for nucleophilic attack at carbon C-1, acting as a general base catalyst [Frandsen et al., 1994]. The crystal structures of glucoamylase complexed with the pseudotetrasaccharides (acarbose and D-gluco-dihydroacarbose), showed that there are two different binding conformers, pH 4-type and pH 6-type, for pseudotetrasaccharides at pH 4 [Aleshin et al., 1996, Stoffer et al., 1995]. Binding of the first two sugar residues of the pseudotetrasaccharides is the same, but there is an extraordinary variation in binding of the third and fourth sugar residues of the pseudotetrasaccharides [Stoffer et al., 1995].

The substrate specificity of an enzyme is determined by its ability to form a stable complex with a ligand in both the ground state and the transition state. The stability of the enzyme-ligand complex is affected by steric constraints, hydrogen bonding, van der-Waal's and electrostatic forces, and hydrophobic contacts [see generally Fersht, 1985 Enzyme Structure and Mechanism, $2^{nd}$ edition, Freeman, San Francisco]. Site-directed mutagenesis was used to construct mutations at residues 119 and 121 to alter the hydrogen bonding between enzyme and substrate. Atom OG of Ser119 hydrogen bonds to the 3-OH of the fourth sugar residue of pseudo-tetrasaccharides only in the pH 6-type conformer, whereas the amide nitrogen of Gly121 hydrogen bonds to the 6-OH of the third sugar residue in both pH 4-type and pH 6-type conformers. These mutations are designed to change substrate. specificity. (decrease alpha-1,6 condensation reactions) while maintaining wild-type ability to hydrolyze alpha-1,4 linked substrates. Ser119 is not conserved and is replaced by Ala, Pro and Glu in other GAs. Mutant S119E was designed to strengthen the hydrogen bond between the enzyme and the fourth sugar residue of the substrate to stabilize the pH 6-type conformer, and to bring a negative charge near subsite 4 in order to increase electrostatic interactions in active site. Mutant S119G was designed to remove the same hydrogen bond in order to destabilize the pH 6-type conformer. Mutant S119W was designed to remove the same hydrogen bond and to increase the hydrophobic interactions between the enzyme and the pH 6-type conformer. Gly121 is highly conserved in all glucoamylase sequences except in Clostridium sp. G005 GA, which has high α-1,6 activity and in which Gly is replaced by Thr. Since the φ and Ψ angles of Gly121 would allow an alanine in this position without causing a conformation distortion, G121A was designed to introduce a Beta-carbon at position 121 to displace the 6-OH group of the third sugar residue from its hydrogen bonding position. In addition, the double mutant G121A/S411G was designed to investigate additivity of the two substrate specificity mutations. S411G is shown herein to reduce the ratio of initial rates of isomaltose production (from glucose condensation reactions) to that of glucose production (from the hydrolysis of DE 10 maltodextrin).

The following provide further examples of the strategies used for the design of mutations having increased selectivity.
300Loop Mutation According to the amino acid sequence homology study [Countinho and Reilly, 1994], it was found that GAs from Rhizopus and some other fungal families have a longer amino acid sequence and form a larger loop or a cavity in the S4 conserved region compared to *A. niger* or *A. awamori* GAs. Since single mutation events alone are unlikely to bring about substantial increase in the specificity of bond hydrolysis or synthesis, an insertional mutant GA was designed, designated 300Loop or 311-314Loop (SEQ ID NO:2), and the inserted seven amino acids were adapted from Rhizopus GA because Rhizopus GA was the first enzyme to which the subsite theory was successfully applied [Himori et al., 1973]. The 300Loop mutation was designed to decrease the α-(1,6)-glucosidic affinity by introducing a larger loop into the S4 conserved region.
Tyr175Phe Tyr175 is within the third conserved region. The nearest distance between Tyr175 and the fourth residue of inhibitor D-gluco-dihydroacarbose is 4.06 A [Stoffer et al., 1995]. Tyr175 is replaced by Phe or Gln in several other glucoamylases. Changing Tyr175 to Phe was designed to increase the hydrophobic interaction between enzyme and substrate.
Gly121Ala Gly121 is highly conserved in all glucoamylase sequences except in Clostridium sp. G005 GA, which has high α-1,6 activity and in which Gly is replaced by Thr. Since the φ and Ψ of Gly121 would allow an alanine in this position without causing a conformation distortion, G121A was designed to introduce a β-carbon at position 121 to displace the 6-OH group of the third sugar residue from its hydrogen bonding position.
Gly121Ala with S411G (Generally Indicated as G121A/S411G)

The double mutant was designed to investigate additivity (cumulative) of the two substrate specificity mutations. S411G reduces the ratio of initial rates of isomaltose production (from glucose condensation reactions, see Examples) to that of glucose production (from the hydrolysis of maltodextrin 10).

The present invention provides a method of engineering mutations for fungal glucoamylase and then preparing engineered enzymes carrying cumulatively additive mutations. The initial step is to generate individual mutations by site directed mutagenesis and screen the individual mutations as described in the Examples. Those individual mutations which show decreased irreversible thermal inactivation rates or reduced isomaltose formation or increased pH optimum are then selected for combinational analysis. In general mutations are selected which have at least wildtype reaction rates.

Mutations are combined by site-directed mutagenesis to determine if their effects are additive as is discussed herein in the Examples. Site directed mutagenesis to produce enzymes carrying at least two of the isolated selected mutations is performed as is known in the art. These engineered enzymes are then screened for cumulatively additive effects on thermal stabilizing, pH optimum or reduced isomaltose formation. Alternatively the engineered enzymes carrying cumulative mutations are screened for cumulative effects on two or more of the parameters.

For biochemical characterization of the mutants, GA is purified from culture supernatants of 15-L batch fermentations by ultrafiltration, DEAE-Sephadex column chromatography, and column affinity chromatography using the potent inhibitor acarbose attached to a support [Sierks et al., 1989]. Purities of the resulting preparations are tested by standard techniques such as SDS-polyacrylamide gel electrophoresis and isoelectric focusing with narrow-band ampholytes. Protein are measured by absorbance at 280 nm or by Bradford's method [1976]. GA activity is measured by a glucose oxidase/o-dianisidine assay (Sigma).

Selectivity is determined by any method known in the art but preferably by measuring the initial rate of isomaltose formation from 30% (w/v) glucose condensation reactions at pH 4.4 and 55° C. in 0.05M sodium acetate buffer and then by measuring the initial rage of glucose formation in 30% (w/v) DE 10 maltodextran hydrolysis reactions at pH 4.4 and 55° C. 0.05M sodium acetate buffer. From the resulting initial rates, the ratio of isomaltose formation to glucose formation is calculated.

Thermostability is measured as is known in the art but preferably by incubating the enzyme at selected temperatures between 65° C. and 77.5° C. at 2.5° C. intervals followed by activity analysis at 35° C. using 4% maltose as substrate. When first-order decay is observed, as with WT GA, decay rate coefficients are determined. Activation energies for decay are calculated from the rate coefficients at different temperatures.

pH optimum is measured as is known in the art but preferably at 45° C. at 16 pH values, ranging for 2.2 to 7.0 using 0.025 M citrate-phosphate buffer with maltose or maltoheptabse as substrate.

Saccharification is measured as described in the Examples. Briefly, glucoamylase is incubated with DE 10 maltodextran as substrate in 0.05M sodium acetate buffer at pH 4.4 at 55° C. Samples are taken at various times from 0.5 to 288 hours and the production of glucose determined.

The present invention provides vectors comprising an expression control sequence operatively linked to the nucleic acid sequence of the various mutant sequences disclosed herein, combinations of mutations and portions thereof. The present invention further provides host cells, selected from suitable eucaryotic and procaryotic cells, which are transformed with these vectors.

Vectors can be constructed containing the cDNA of the present invention by those skilled in the art and should contain all expression elements necessary to achieve the desired transcription of the sequences. Other beneficial characteristics can also be contained within the vectors such as mechanisms for recovery of the nucleic acids in a different form. Examples are provided herein. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art (calcium phosphate transfection; electroporation; lipofection; protoplast fusion; polybrene transfection; ballistic DNA delivery; lithium acetate or CaCl transformation). The host cell can be any eucaryotic and procaryotic cells, which can be transformed with the vector and which will support the production of the enzyme.

The above discussion provides a factual basis for thermostable and selective mutants of fungal glucoamylase as well as methods of designing the mutations and screening for the cumulative effect of the mutations and vectors containing the mutations. The methods used with and the utility of the present invention can be shown by the following non-limiting examples and accompanying figures.

EXAMPLES

General Methods in Molecular Biology

Standard molecular biology techniques known in the art and not specifically described were generally followed as in Sambrook et al., *Molecular Cloning: A Laboratory Manual*, Cold Springs Harbor Laboratory, New York (1989), and in Ausubel et al., *Current Protocols in Molecular Biology*, John Wiley and Sons, Baltimore, Md. (1989) and Rose, et al. *Methods in Yeast Genetics: A Laboratory Course Manual,* Cold Spring Harbor Laboratory Press, Cold Spring Harbor, N.Y. (1990). Polymerase chain reaction (PCR) was carried out generally as in *PCR Protocols: A Guide To Methods And Applications,* Academic Press, San Diego, Calif. (1990). Oligonucleotides are synthesized as is known in the art. For example, an Applied Biosystems 380B DNA synthesizer can be used.

Materials

*S. cerevisiae* C468 (α leu2-3 leu 2-112 his 3-11 his 3-15 mal⁻) and the plasmid YEpPM18 were gifts from Cetus. Acarbose was a gift from Miles Laboratories. All restriction enzymes were purchased from Promega as well as T4 DNA ligase and pGEM-7Z(+), an *E. coli* phagemid vector, were from Promega. Maltose ($G_2$), maltotriose ($G_3$), maltotetraose. ($G_4$), maltopentaose ($G_5$), maltohexaose ($G_6$), maltoheptaose ($G_7$), glucose oxidase, peroxidase, and α-naphthol were from Sigma. Isomaltose ($iG_2$) was purchased from TCI America. DE 10 Maltodextrin with the average degree of polymerizations (DP) of ten, six, and four, respectively, were from Grain Processing Corporation. High-performance thin-layer chromatographic (HPTLC) plates (LHPK silica gel 60 Å, 20×10 cm) were from Whatman.

Site-directed Mutagenesis

Site-directed mutagenesis was performed according to the Muta-Gene phagemid in vitro mutagenesis kit from Bio-Rad which is based on the method of Kunkel et al [1985]. A 1.7 kb XhoI→BamHI DNA fragment coding for the glucoamylase catalytic domain was cloned into a pBluescript II KS(+) vector from Stratagene. Oligonucleotides used as mutagenic primers are provided with the specific Example. The presence of the individual mutations was confirmed by sequencing and each mutated GA gene fragment was subcloned into YepPM18 [Cole, et al., 1988] and transformed into *S. cerevisiae*.

Enzyme Production and Purification

Wild-type (WT) and mutant enzymes are produced by growing yeast at 30° C. in 5.3 L SD+His media for 72 hours at pH 4.5 in a 5.0 L fermentor. After 48 hours, 100 g of dextrose and 22 g of $(NH_4)_2SO_4$ in 300 ml $H_2O$ is added as a supplement. Following growth, the culture is centrifuged to remove yeast cells, the supernatant is concentrated by ultrafiltration, diafiltered against 0.5 M NaCl/0.1 M NaOAc, pH 4.5 and purified by acarbose-sepharose affinity chromatography. GA is eluted with 1.7 M Tris-Cl, pH 7.6, dialyzed against $H_2O$, further concentrated by ultrafiltration and diafiltered against 0.05 M NaOAc buffer, pH 4.5. The protein concentration is determined according to the Pierce bicinchoninic acid protein assay [Smith et al., 1985] using bovine serum albumin as a standard.

Enzyme Activity Assays

Enzyme activities were determined at 50° C. using 4% maltose in 0.05 M NaOAc buffer pH 4.5 as substrate. One international unit (IU) of enzyme activity was defined as the amount of enzyme required to produce 1 μmol/min glucose at assay conditions. Following mixing enzyme with substrate, six 100 μl samples were removed at seven minute intervals over 42 minutes, the reaction stopped with 40 μl of 4.0 M Tris-Cl, pH 7.0 and the glucose concentration was determined according to the Sigma peroxidase-glucose oxidase/o dianisidine glucose assay kit.

Irreversible Thermal Inactivation

Duplicate aliquots of 40 μg/ml of purified wild-type and mutant enzymes were subjected to inactivation at six or more temperatures between 65° and 80° C. at intervals of 2.5° C. Samples were removed at six different time points, immediately placed on ice and stored at 4° C. for 24 hours. The residual activity of the inactivated samples along with a corresponding sample which had not been subjected to thermal inactivation, was determined as described above but at 35° C.

pH Dependence of Glucoamylase Activity pH dependence of glucoamylase activity was measured at 45° C. at 16 different pH values, ranging from 2.2 to 7.0, using 0.025 M citrate-phosphate buffer [McIlvane, 1921] with maltose. or maltoheptaose as substrate. The ionic strength of the citrate-phosphate buffer was maintained at 0.1 by adding potassium chloride.. The pK values of free enzyme and enzyme-substrate complex were measured at substrate concentrations (i) smaller than 0.2 $K_m$, so that the initial rate (v) was proportional to $k_{cat}/K_m$, and (ii) higher than 10 $K_m$, so that the initial rate (v) was proportional to $k_{cat}$ [Sierks & Svensson, 1994, see also Whitaker (1994) Principle of enzymology for the food sciences, $2^{nd}$ edition, Marcel Dekker, NY]. The pK values of two catalytic groups of free enzyme and enzyme-substrate complex were calculated by fitting the initial rates as a function of pH values to the equation log Y=log $[C/(1+H/K_1+K_2/H]$ by using the software of Enzfitter. Y is the observed value of the parameter of interest (i.e. $k_{cat}/K_m$ or $k_{cat}$) measured at different pH values, C is the pH independent value of Y (i.e. the maximal value of $k_{cat}/K_m$ or $k_{cat}$) H is the concentration of hydrogen ion, $K_1$ and $K_2$ are dissociation constants of catalytic groups of enzyme. When the values of apparent $pK_1$ and $pK_2$ were separated by less than three pH units, the pK values were adjusted by equations $(H^+)_1+(H^+)_2=K_1+4(H^+)_{opt}$ and $(H^+)_{opt}^2=K_1K_2$ [Whitaker, 1994]. The concentration of hydrogen ion at the optimum pH, $(H^+)_{opt}$, was calculated from pHopt which is equal to the average of apparent $pK_1$ and $pK_2$. $(H^+)_1$ and $(H^+)_2$ (apparent $K_1$ and $K_2$) correspond to the concentrations of hydrogen ion when the pH values are equal to apparent $pK_1$ and $pK_2$, respectively.

The Hydrolysis of DE 10 Maltodextrin (Saccharification)

Hydrolysis was performed at 35° C. and/or 55° C. (as indicated in the text) with 28% (w/v), DE 10 maltodextrin as substrate in 0.05 M sodium acetate buffer at pH 4.4 with the addition of 0.02% sodium azide, used to inhibit microbial growth in the reaction mixtures. The enzyme concentration was 2.64 μM for both wild-type and mutant GAs. Samples were taken at various times (from 0.5 to 288 hours) and the reactions were stopped by adding samples to the same volume of 1 M Tris-HCl buffer at pH 7.0, since Tris is a known inhibitor of glucoamylase [Clarke & Svensson, 1984]. The production of glucose was determined by the glucose oxidase method [Rabbo & Terkildsen, 1960]. Initial rates of glucose production were determined by fitting the experimental data to the equation c=At/(1+Bt), where c is the product concentration, t is time, and A (the initial rate) and B are obtained from the nonlinear regression. At 55° C., only the time points before 70 hours were used for the calculations, since the glucose production by that time had already declined for wild-type GA.

Glucose Condensations Reactions

Glucose condensation reactions were performed at 35° C. and 55° C. with 30% (w/v), D-glucose as substrate in 0.05 M acetate buffer at pH 4.4 for 12 days with the addition of 0.02% sodium azide, used to inhibit microbial growth in the reaction mixtures. The enzyme concentration was 2.64 μM for both wild-type and mutant GAs. Samples were taken at various times and the reactions were stopped by adding samples to the same volume of 1 M Tris-HCl buffer at pH 7.0. High Performance Thin Layer Chromatography (HPTLC) and Imaging Densitometry were used to determine the production of isomaltose by a method modified from that described by Robyt et al. [Robyt and Mukerjea, 1994]. One microliter of variously diluted samples and six different concentrations of standard (containing glucose, maltose and isomaltose) were applied to the HPTLC plates. The developing solvent system contained acetonitrile, ethyl acetate, 1-propanol and water in the volume proportions of 85:20:50:40. Only one ascent was used to develop the carbohydrate separation on HPTLC plates. After development, the plates were air-dried, dipped into an EtOH solution containing 0.3% (w/v) alpha-naphthol and 5% (v/v) $H_2SO_4$, air-dried again, and incubated approximately 10 minutes at 120° C. to visualize the carbohydrates. Densities of the isomaltose spots on HPTLC plates were quantified by Imaging Densitometry (Bio-Rad, Model GS-670), using Molecular Analyst software (Bio-Rad). The experimental data were fitted to the equation c=At/(1+Bt), described above for the hydrolysis of DE 10 maltodextrin, to obtain the initial rates of isomaltose production.

Example 1

Stabilization of *Aspergillus Awamori* Glucoamylase by Proline Substitution

The following example is an exemplar of the methods and procedures that are used in the analysis of an individual mutation of a glucoamylase. To investigate the mechanisms governing *Aspergillus awamori* glucoamylase thermal stability, three proline substitution mutations were constructed. These mutations were predicted to increase GA stability by decreasing the enzyme's conformational entropy of unfolding.

*Aspergillus awamori* glucoamylase (α-1,4-D-glucan glucohydrolase, EC 3.2.1.3; GA) is an enzyme which catalyses the release of β-glucose from the non-reducing ends of starch and related oligosaccharides. GA is used in, and defines the rate limiting step of, the commercial conversion of starch to high glucose syrups which may be converted to fructose syrups by glucose isomerase, or used in fermentations to produce ethanol. GA is used industrially at 55°–60° C.; at higher temperatures the enzyme is rapidly and irreversible inactivated. Therefore, a GA variant with increased thermostability would be advantageous industrially to decrease reaction times and/or to increase solids concentrations.

Previous work has shown that the natural stability of oligo 1,6-glucosidase [Suzuki et al., 1987] and pullulanase [Suzuki et al., 1991] can be positively correlated to the mole percent proline present in the protein, and a general rule for protein stability has been proposed [Suzuki, 1989]. This work has been extended to show that bacteriophage T4 lysozyme [Matthews et al., 1987] and *Bacillus cereus* ATCC 7064 oligo 1,6 glucosidase [Watanabe et al, 1994] can be stabilized by engineering proline into selected sites thereby decreasing the protein's conformational entropy of unfolding.

Three sites (Ser30, Asp345 and Glu408→Pro) were selected for proline substitution based on structural and evolutionary considerations. Mutations at these sites were constructed using the cloned *A. awamori* gene [Innis et al, 1985] and the proteins were expressed in *Saccharomyces* cerevisiae [Cole, et al, 1988]. The stability of the mutant proteins was measured by their resistance to irreversible thermal inactivation at various temperatures. As shown herein, the Ser30→Pro mutation increased. However, unexpectedly the Glu408→Pro mutation decreased and the Asp345→Pro mutation did not significantly alter GA stability.

Site-Directed Mutagenesis

Site-directed mutagenesis was performed as described herein above. The following oligonucleotides were used as mutagenic primers: CAGAGTCCGCGCCCG GCACCCAAGCACCGTC (Ser30→Pro) (SEQ ID No:3), AAGTCCAGCGACACAGGTGTGACCTCCAACGAC (Asp345→Pro) (SEQ ID No:4) and CGAGCG-GAAAGCTGCGGGCCATCAGACTTGTC (Glu408→Pro) (SEQ ID No:5).

Selection of Sites for Proline Substitution

Based on the nearly identical catalytic domain of *A. awamori* var X100 GA whose structure is known [Aleshin et al, 1992] three sites for substitution were chosen, which met the following criteria: 1) Ramachandran ($\phi$, $\Psi$) angles were within allowed values for proline [Ramachandran et al., 1963]. For this work the $\phi$ and $\Psi$ angles at the substituted site were restrained-to the broad range $\phi=-90°$ to $-40°$, $\Psi=120°$ to $180°$ or $\phi=-90°$ to $-40°$, $\Psi=-50°$ to $10°$. 2) Residues were highly solvent exposed, since mutation of residues in the core of the enzyme were thought to be more likely to decrease the enzyme's catalytic efficiency. 3) Residues didn't participate in hydrogen bonding with other amino acids. Additionally, based on sequence alignments with GAs from other organisms [Coutinho and Reilley, 1994b] only residues which met the above structural criteria and were not well conserved were selected for mutation. Ser30 could be aligned with proline in GAs from *Hormoconis grisea* var *thermoidea* and *H. resiae* GamP [Coutinho and Reilly, 1994b], which made it particularly attractive for proline substitution.

Results

Specific Activity

None of the proline substitution mutations significantly altered enzyme specific activities of wild-type and mutant GAs at 50° C. and pH 4.5. This suggests that these mutations did not significantly alter the enzyme's structure around the active site or alter its interaction with substrate.

Irreversible Thermal Stability

Figure 1:
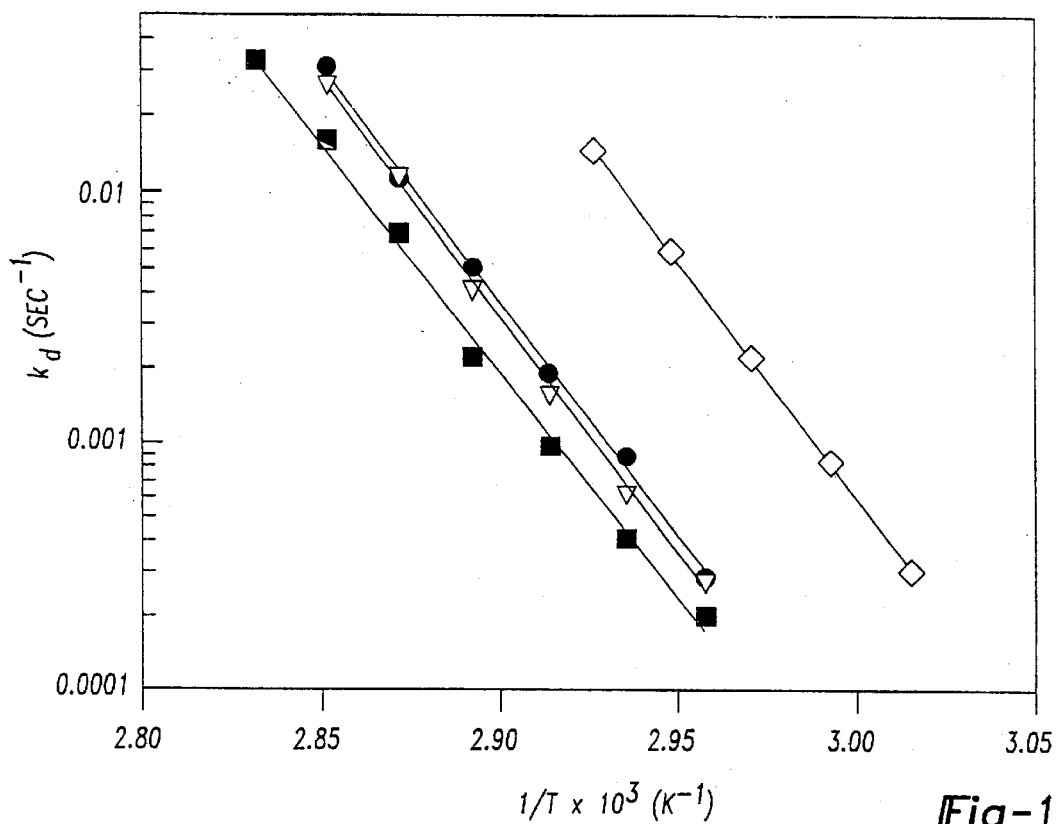
FIG. 1 is a graph showing the relationship between temperature and kd for wild-type (●) and proline substituted mutant GA's: S30P (■), D345P (▽), E408P (◇) in Example 1.

Wild-type and mutant GAs were subjected to thermal inactivation at pH 4.5 as described in the experimental protocols. Semilogarithmic plotting of the percent residual activity against inactivation time yielded inactivation rate coefficients (kd). FIG. 1 shows the relationship between temperature and kd for wild-type and mutant GAs. Based on these data, activation energies for thermal inactivation ($\Delta G^{\ddagger}$) were calculated using transition state theory and melting temperatures (Tm), the temperature at which the enzyme was 50% inactivated after ten minutes were computed (Table 1). As can be seen, the Glu408→Pro mutation greatly decreased, the Asp345→Pro mutation did not significantly alter and the Ser30→Pro mutation increased GA stability.

It should be noted that although Table 1 shows that the Asp345→Pro mutant GA demonstrated slightly increased $\Delta G^{\ddagger}$ and Tm, these changes are generally not significant or that the Asp345→Pro mutant GA is more stable than wild-type since the kds for this mutant enzyme at two well separated temperatures (65° and 75° C.) are essentially indistinguishable from wild-type (FIG. 1).

The proline substitution mutations had different thermostabilities when measured by their resistance to irreversible thermal inactivation. When compared to wild-type GA, Glu408→Pro decreased, Asp345→Pro did not significantly alter and Ser30→Pro increased GA stability (FIG. 1 and Table 1).

Glu408→Pro destabilized GA. As was first suggested by Schimmel and Flory [1968] and has been expanded by others [MacArthur and Thornton, 1991; Hurley et al, 1992] proline not only restricts the $\phi,\Psi$ values for the site at which it exists, but also the $\phi,\Psi$ values of the preceding residue. These reports suggest that the ($\phi,\Psi$) values for the residue preceding proline should be restricted to approximately $\phi=-180°$ to $-55°$ and $\Psi=55°$ to $180°$ or $\Psi=-180°$ to $-55°$ and $\Psi=-30°$ to $-70°$ for all residues in Xaa-Pro except for Xaa-Gly, for which the preceding still applies, but is extended to include $\phi=45°$ to $180°$. In the published *A. awamori* var. X100 catalytic domain structure [Aleshin et al., 1992], Asp408 ($\phi=-65°$, $\Psi=146°$) which aligns with Glu408 in *A. awamori* GA, has $\phi,\Psi$ values within ranges acceptable for praline. However, the preceding residue Gly407 ($\phi=80°$, $\Psi=-5°$) has $\phi,\Psi$ outside acceptable ranges for positions preceding praline. It is not surprising then, that the Glu408Pro destabilized GA. Additionally, X-ray crystallography suggests that position 408, in the closely related *A. awamori* var. X100 GA[2], lies within a β-strand; a site not well suited for proline substitution.

Asp345 ($\phi=-65°$, $\Psi=-26°$) and the preceding Thr344 ($\phi=-116°$, $\Psi=178°$) have $\phi,\Psi$ angle values lay well within allowed values for proline substitution at position 345. However, the Asp345→Pro mutant GA did not demonstrate stability significantly different from wild-type GA. This is particularly unexpected since position 345 lies at the N-terminus of an α-helix[2]; a position previously shown to be particularly favorable-for proline substitution [Watanabe et al, 1994].

Ser30 ($\phi=-49°$, $\Psi=130°$) is preceded by Val29 ($\phi=-127°$, $\Psi=46°$) both of which have acceptable $\phi,\Psi$ angle values except Val29 $\Psi=46°$ which is slightly smaller than ideal for proline substitution at position 30.

In summary, when expressed in *Saccharomyces cerevisiae*, Glu408→Pro greatly decreased, Asp345→Pro, did not significantly alter and Ser30→Pro strongly stabilized the enzyme. The Ser30→Pro mutant GA showed a significantly decreased rate of irreversible thermal inactivation when analyzed between 65° and 77.5° C. without decreased enzyme activity. At 65° C. a 1.7-fold decrease in thermal inactivation rate coefficients was seen and the activation energy for thermal inactivation was increased by 1.6 kJ/mol relative to wild-type GA.

Example 2

Engineered Disulfide Bonds

The following example is an exemplar of the methods and procedures that are used in the analysis of an individual mutation of a glucoamylase. The process of GA thermoinactivation is thought to be dominated by formation of enzymes with incorrect conformation [Munch and Tritsch, 1990]. Previous work supported this hypothesis. Site-directed mutagenesis has been used to eliminate sites of deamidation and peptide hydrolysis Chen et al., 1994 a,b). The corresponding mutations Asn182→Ala and Asp257→Glu had reduced irreversible thermoinactivation rates at pH 4.5 below 70° C. but increased rates above 70° C. Thus GA thermoinactivation is predominantly caused by "scrambled" structures rather than by deamidation and peptide hydrolysis. Furthermore, mutations Gly137→Ala, Gly139→Ala and Gly137/139→Ala/Ala, made to reduce helix flexibility, showed increased thermostability up to 75° C. (Chen et al., 1996) apparently by slowing down the formation of incorrect structures.

To improve protein thermostability by preventing formation of incorrect structures, several strategies have been proposed including introducing covalent linkage such as disulfide bonds (Perry and Wetzel, 1984; Wetzel, 1987; Matsumura et al., 1989, Clarke and Fersht, 1993).

There are a total of nine cysteine residues in *A. awamori* GA, eight of which form disulfide-linked pairs, which are assumed to enhance the folding and stability of GA, residues 210 and 213, 262 and 270, 222 and 449 [Aleshin et al., 1992] and 509 and,604 [Williamson et al., 1992b]. In this Example, additional disulfide bonds are introduced into GA to explore the effect on thermostability and catalytic activity. Two engineered disulfide bond mutants designated A27C/N20C (abbreviated S-S) and A471C/T72C were constructed. The new disulfide bond formed by A27C/N20C connects the C-terminus of helix 1 (Asn20) and a turn where residue Ala27 is located, while A471C/T72C bridges the N-terminus of helix 3 and the end of the 30-residue highly O-glycosylated belt region together. The disulfide bonds are formed spontaneously after fermentation and have different effects on GA thermostability and catalytic activity.

Site-Directed Mutagenesis

Site-directed mutagenesis was performed as described herein above. Oligonucleotide primers used are: 5'-CGT ACT GCC ATC CTG <u>TGT</u> AAC ATC GGG GCG GA-3' (N20C, AAT→TGT) (SEQ ID No:6), 5'-ATC GGG GCG GAC GGT <u>TGT</u> TGG GTG TCG GGC GCG-3' (A27C, GCTTGT) (SEQ ID No:7), 5'-CGA AAT GGA GAT <u>TGC</u> AGT CTC-3' (T72C, ACC→TGC) (SEQ ID No:8), 5'-G AGT ATC GTG TGT ACT GGC GGC ACC-3' (A471C, GCT→TGT) (SEQ ID No:9), with the underlined letters indicating the nucleotide mutations.

SDS-PAGE and Thio-Titration

SDS-PAGE was carried out using 0.75 mm thick 10% polyacrylamide gels following the method of Garfin [1990]. For thio-titration, GA at two mg/ml concentration was denatured by boiling in denaturing solution containing 2% SDS, 0.08 M sodium phosphate (pH 8.0) and 0.5 mg/ml EDTA [Habeeb, 1972] with or without 50 mM DTT [Pollitt and Zaikin, 1983] for ten minutes. The denatured GA (reduced or non-reduced) was concentrated using Centricon 30 concentrators (Amicon, Mass., USA) and the reduced GA was applied to Bio-spin 30 chromatography columns (Bio-Rad, CA, USA) pre-equilibrated with denaturing solution to remove DTT. The resulting solution as well as the non-reduced denatured GA sample were divided into two portions. One portion was used for a protein concentration assay and the other portion was assayed for thio reduction by mixing with four mg/ml DTNB in denaturing solution with a 30:1 volume ratio, followed by incubation at room temperature for 15 minutes, and absorbance measurement at 412 nm with a molar absorptive value of 13,600 $M^{-1}cm^{-1}$ [Habeeb, 1972].

GA Activity Assay

As described herein above, maltose was used as substrate in enzyme kinetics studies, with concentrations ranging from 0.2 $K_m$ to 4 $K_m$ at 35° C. and pH 4.5 as described previously [Chen et al., 1994b]. Kinetics parameters were analyzed by the program ENZFITTER. In residual enzyme activity assays, the conditions are the same as in the enzyme kinetics studies except that only one concentration of maltose (4%) is used as substrate. Specific activity assays were carried out with 4% maltose as substrate at 50° C. and pH 4.5. One unit (IU) was defined as the amount of enzyme required to produce 1 $\mu$mol glucose per minute under the conditions of the assay. To compare the temperature optima of catalytic activities of wild-type and mutant GA, activities were assayed at pH 4.5 with 4% maltose as substrate at different temperatures.

Irreversible Thermoinactivation

As described herein above, purified wild-type or mutant GA proteins were incubated at five different temperatures from 65° C. to 75° C. at 2.5° C. intervals at 40 $\mu$g/ml in 0.05 M NaOAC buffer (pH 4.5). At six different time points, aliquots of the incubating enzyme were removed, quickly chilled on ice, stored at 4° C. for 24 hours, and subjected to residual activity assay. The irreversible thermoinactivation of GA obeyed first-order kinetics [Chen et al., 1994b]. Thermoinactivation rate coefficients, $k_d$ were determined as described previously [Chen et al., 1994b].

Computer Modeling and Three-dimensional View of Mutated Residues

The candidate residues of *A. awamori* GA to form disulfide bond were modeled with the crystal structure of *A. awamori* var. X100 GA [Aleshin et al., 1992] (1gly in the Brookhaven Protein Data Bank) as reference by the SSBOND program (Hazes and Dijkastra, 1988) installed in a DEC 3100 workstation.

Selection of Mutation Site

Residues Asn20, Ala27 and Thr72, Ala471 were chosen to be replaced with cysteine. After the analysis of crystal structure of *A. awamori* var. X100 GA [Aleshin et al., 1992] by the program SSBOND, 132 pairs of residues were found that could potentially be sites for a disulfide bond. Pairs containing glycine were discarded on the assumption that glycine may be required for flexibility at that site. Also, the residues involved in hydrogen bonds and electrostatic interactions were eliminated. Residues 20 paired with 27 as well as 72 paired with 471 were chosen as candidates for disulfide bond formation according to the geometrical analysis. Amino acid sequence alignment among related GAs showed that there is a disulfide bond between position 20 and 27 in *Neurospora crassa* [Coutinho and Reilly, 1994b], which suggested that introducing disulfide bond between position 20 and 27 would not cause unfavored interactions there in *A. awamori* GA. Furthermore, the 20/27 disulfide bond would link the C-terminus of helix 1 and the conserved S1 fragment of GA involved in substrate binding [Coutinho and Reilly, 1994a] to form a loop, near another loop very critical for catalysis containing Trp 120, a residue involved in substrate binding [Sierks et al., 1989]. Therefore, the proposed 20/27 disulfide bond was expected to stabilize GA by keeping the correct conformation for catalysis and substrate binding.

Another further candidate for a disulfide bond pair was between positions 471 and 72. This disulfide bond would link the N-terminus of helix 3 and the end of the 30-residue (440–470) highly O-glycosylated belt region to form a loop. This disulfide bond also would make an additional linkage between the catalytic domain and the O-glycosylated linker. This O-glycosylated linker has been proved to be important for GA thermostability by limiting the conformational space available to the GA unfolded peptide [Semimaru et al., 1995 and Williamson et al., 1992]. This disulfide bond could have a globe effect on the thermostability of GA because of this linkage. The side chain —OH group of Thr72 in *A. awamori* var. X100 GA [Aleshin et al., 1992] is hydrogen bonded to the main chain N atom of Asp73. In *A. awamori* GA, however serine is found at residue 73 in place of Asp. It is possible that the hydrogen bond between residues 72 and 73 does not exist in *A. awamori* GA, and therefore replacing Thr72 with Cys will not disturb this interaction. This hydrogen bond is apparently not critical for GA since Thr72 is replaced by Ala, Lys or Val in other GAs [Coutinho and Reilly, 1994b].

Engineered Disulfide Bonds were Formed Spontaneously

After GA purification, the engineered disulfide bonds were found to be formed spontaneously by the following two approaches.

First, the mutant A471C/T72C has faster mobility than wild-type during SDS-PAGE under non-reducing conditions, suggesting that an additional disulfide bond forms a new loop retarding the migration. The possibility that a truncated enzyme was formed in this case was eliminated by DNA sequencing of the mutant cDNA and MALDI analysis. The MALDI data showed that the mutant GA had the same molecular weight as wild-type GA. Mutant A27C/N20C has the same migration as wild-type GA, which may be because the additional loop caused by the engineered disulfide bond is too small (seven residues) to affect migration.

Second, the new disulfide bonds were demonstrated by thio group titration. Comparing the numbers of free thio groups before and after the treatment of reducing reagent DTT, the total disulfide bonds in mutant and wild-type GA were deduced as reported in Table 2. Wild-type, A27C/N20C, and A417C/T72C GA have in total 8.6, 10.9, and 10.4 free thio groups respectively according to the [SH]/molecule ratio in the presence of reducing reagent DTT (Table 2). In the absence of DTT the numbers are 0.9, 0.9 and 1.3, respectively (Table 2). This suggested that the number of disulfide bonds among wild-type, A27C/N20C and A471C/T72C are 4, 5 and 5, respectively. Therefore, the introduced cysteine residues formed disulfide bonds instead of remaining free thiols.

Enzymatic Activity and Optima Temperature of Catalysis

The enzymatic properties of double mutations A27C/N20C and A471C/T72C were not changed compared with wild-type at 35° C. and 50° C. as shown in Table 3, while single mutations had significant reduced activity. Mutant A27C/N20C and A471C/T72C had specific activities at 50° C. and kinetic parameters at 35° C. very close to wild-type GA (Table 3). The single mutant A27C had slightly increased $K_m$ but the same $k_{cat}$ value as wild-type GA, and thus a reduced $k_{cat}/K_m$ ratio of ~30%. Mutant N20C had the same $K_m$ but both a decreased $k_{cat}$ and $k_{cat}/K_m$ ratio and a decreased specific activity at 50° C. of more than 50%.

Irreversible Thermoinactivation of GA

Figure 2:
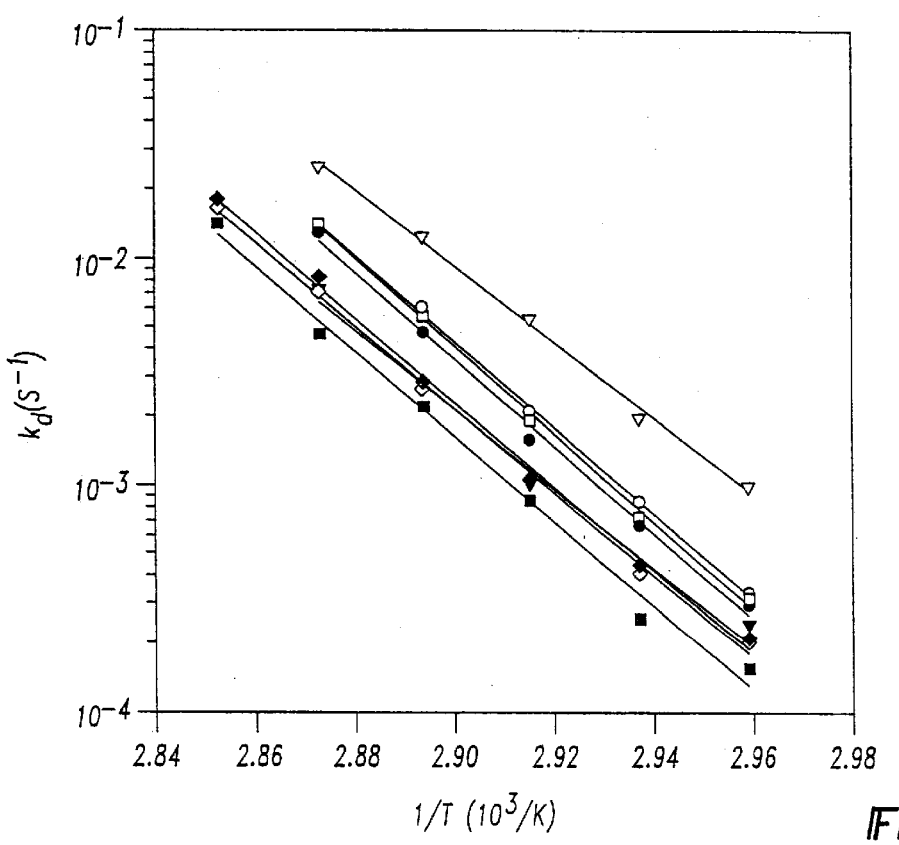
FIG. 2 is a graph showing effect of temperature on first-order thermoinactivation rate coefficients of wild-type (○), A27C (●), N20C (▽), A27C/N20C (▼), A471C/T72C (□), A27C/N20C/G137A (■), A27C/N20C/S436P (◇) AND G137A/S436P (◆) glucoamylases measured in pH 4.5 buffer.

The irreversible thermoinactivation of wild-type and mutant GA was studied at 65° C., 67.5° C., 70° C., 72.5° C. and 77.5° C. with first-order irreversible theremoinactivation coefficients $k_d$ shown in FIG. 2. Mutants A27C, A27C/N20C and A471C/T72C had smaller $k_d$ values than did wild-type GA within the measured temperature range, which means the activity decayed more slowly than wild type, while mutant N20C had greater $k_d$ value than wild-type at all temperatures except 75° C., which means that N20C decayed faster than wild-type.

Table 4 shows the activation enthalpy ($\Delta H_\ddagger$), entropy ($\Delta S_\ddagger$) and free energy of unfolding ($\Delta G_\ddagger$) at 65° C. and 75° C. of wild-type and mutant GAs, calculated according to transition-state theory. The enthalpies of N20C and A27C/N20C decreased by 42 and 24 KJ/mol respectively, while no significant change occurs for A27C and A471C/T72C. Mutants N20C and A27C/N20C had decreased entropy of 115 kJ/mol and 75 kJ/mol respectively, while entropy of mutants A27C and A471C/T72C showed no significant change. Mutant A27C and A471C/T72C had a slightly higher $\Delta G^\ddagger$ than wild-type GA at 65° C. and 75° C. (<0.5 kJ/mol), while the $\Delta G^\ddagger$ of A27C/N20C was higher than that of wild-type by 1.5 and 2.2 kJ/mol at 65° C. and 75° C. respectively. Mutant N20C had a decreased $\Delta G^\ddagger$ by 3.0 and 1.8 kJ/mol at 65° C. and 75° C., respectively, compared with wild-type GA. Therefore, the engineered disulfide bond mutant A27C/N20C significantly increased GA thermostability compared with wild-type GA while the single mutants produced either a slight increase (A27C) or a slight decrease (N20C) in thermostability. The other disulfide bond mutant had the thermostability identical to wild-type GA.

Example 3

Mutation A27C/N20C in Combination with Other Mutations

In previous studies applicants have constructed the thermostable mutants G137A [Chen et al., 1996] and S436P (Li et al., 1996), which have the potential to be combined and improve thermostability additively. In this Example, these mutations are combined with each other and with A27C/N20C (S-S; Example 2) to test their effects (cumulative/additive) on thermostability and GA activity.

Enzymatic Activity and Optima Temperature of Catalysis

The combined mutants A27C/N20C/G137A and A27C/N20C/S436P had increased specific activity while mutant G137A/S436P had similar specific activity to wild-type GA (Table 3). The double mutants A27C/N20C and A471C/T72C as well as the combined mutant A27C/N20C/G137 had changed optimal temperatures for catalysis.

Relative activity assays at temperatures from 60° C. to 74° C. (FIG. 3) showed that wild-type, mutant A27C/N20C and A471C/T72C had the highest activity at 71° C., 72° C. and 72.5° C., respectively. From 60° C. to 67.5° C., mutant and wild-type GA had very similar activities. However, when the temperature was above 70° C., their relative activities differed substantially. Mutants A27C/N20C and A27C/N20C/G137A had higher activity than wild-type consistently from 70° C. to 76° C. with a peak at 72.5° C., while mutant A471C/T72C had activity lower than wild-type from 70° C. to 71° C. and 73° C. to 74° C. but higher at 72° C. which is its optimal temperature. Thus mutant GAs A27C/N20C, A471C/T72C and the combined mutant A27C/N20C/G137A had increased temperature optima above wild-type GA by 1.50° C.

Irreversible Thermoinactivation of GA

The irreversible thermoinactivation of wild-type and mutant GA was studied at 65° C., 67.5° C., 70° C., 72.5° C. and 77.5° C. with first-order irreversible theremoinactivation coefficients $k_d$ shown in FIG. 2. Mutants A27C, A27C/N20C and A471C/T72C, A27C/N20C/G137A, A27C/N20C/S436P and G137A/S436P had smaller $k_d$ values than did wild-type GA within the measured temperature range, which means the activity decayed more slowly than wild type, while mutant N20C had greater $k_d$ value than wild-type at all temperatures except 75° C., which means that N20C decayed faster than wild-type.

Table 4 shows the activation enthalpy ($\Delta H_\ddagger$), entropy ($\Delta S_\ddagger$) and free energy of unfolding ($\Delta G_\ddagger$) at 65° C. and 75° C. of wild-type and mutant GAs, calculated according to transition-state theory.

The helix flexibility mutant G137A showed additive thermostability when combined with either S436P or A27C/N20C. The combination S436P with A27C/N20C did not show additivity.

Example 4

Further Studies with Combined Mutations

To further investigate whether individual stabilizing mutations can cumulatively stabilize *Aspergillus awamori* glucoamylase (GA), mutant enzymes were constructed containing combinations of thermostabilizing mutations. Previous work has shown that the following mutations stabilize GA as demonstrated by decreased irreversible thermal inactivation rates when inactivated in the absence of carbohydrate: Ser30→Pro (S30P; Example 1), Gly137→Ala (G137A), and Asn20→Cys/Ala27→Cys (which creates a disulfide bond between residues 20 and 27 and is therefore noted as S-S for convenience; Example 2). To investigate whether individual stabilizing mutations can cumulatively stabilize GA, additional combined mutant enzymes were prepared utilizing the these three mutations.

Site-directed Mutagenesis

The S-S/S30P/G137A combined mutant was constructed using the S-S/S30P oligonucleotide listed above and a single stranded DNA template derived from a pBluescript II KS(+) vector with a 1.7 kb XhoI→BamHI DNA fragment coding for the GA catalytic domain which already contained mutations conferring the S30P and G137A amino acid substitutions. The presence of the individual mutations was confirmed by sequencing and each mutated GA gene fragment was subcloned into YEpPM18 [Cole et al., 1988] and transformed into S. cerevisiae.

Thiol Analysis 10 nmol of wild-type, S-S/S30P and S-S/S30P/G137A mutant GAs were incubated in 0.2 mM 5,5'-dithiobis(2-nitrobenzoic acid), 6 M GdnHCl, and 50 mM Tris, pH 8 in duplicate [Fierobe et al., 1996]. The thiol concentration was calculated from a standard curve established using 0–30 $\mu$M cysteine.

Irreversible Thermal Inactivation

Wild-type and mutant GAs were subjected to thermal inactivation at six or seven temperatures between 65° and 80° C. at 2.5° C. intervals in duplicate. Following 24 hours at 4° C., the residual activities of the inactivated samples were analyzed at 35° C. along with a corresponding sample which had not been inactivated [Chen et al, 1996].

Saccharification Analysis

Saccharifications were performed in duplicate using stirring heating blocks and tightly sealed vials to prevent evaporation. Eight $\mu$g/ml of wild-type and mutant GAs were assayed using 28% (w/v) Maltrin DE 10 maltodextrin in 0.05 M NaOAc pH 4.5 as substrate. At various times, sample was removed, diluted appropriately in 0.05 M NaOAc pH 4.5 and the reaction stopped by adding 100 $\mu$l of diluted sample to 40 $\mu$l of 4.0 M Tris-Cl, pH 7.0. The glucose concentration was determined by a glucose oxidase/o dianisidine assay [Banks and Greenwood, 1971].

Results

Enzyme Activities

Figure 4:
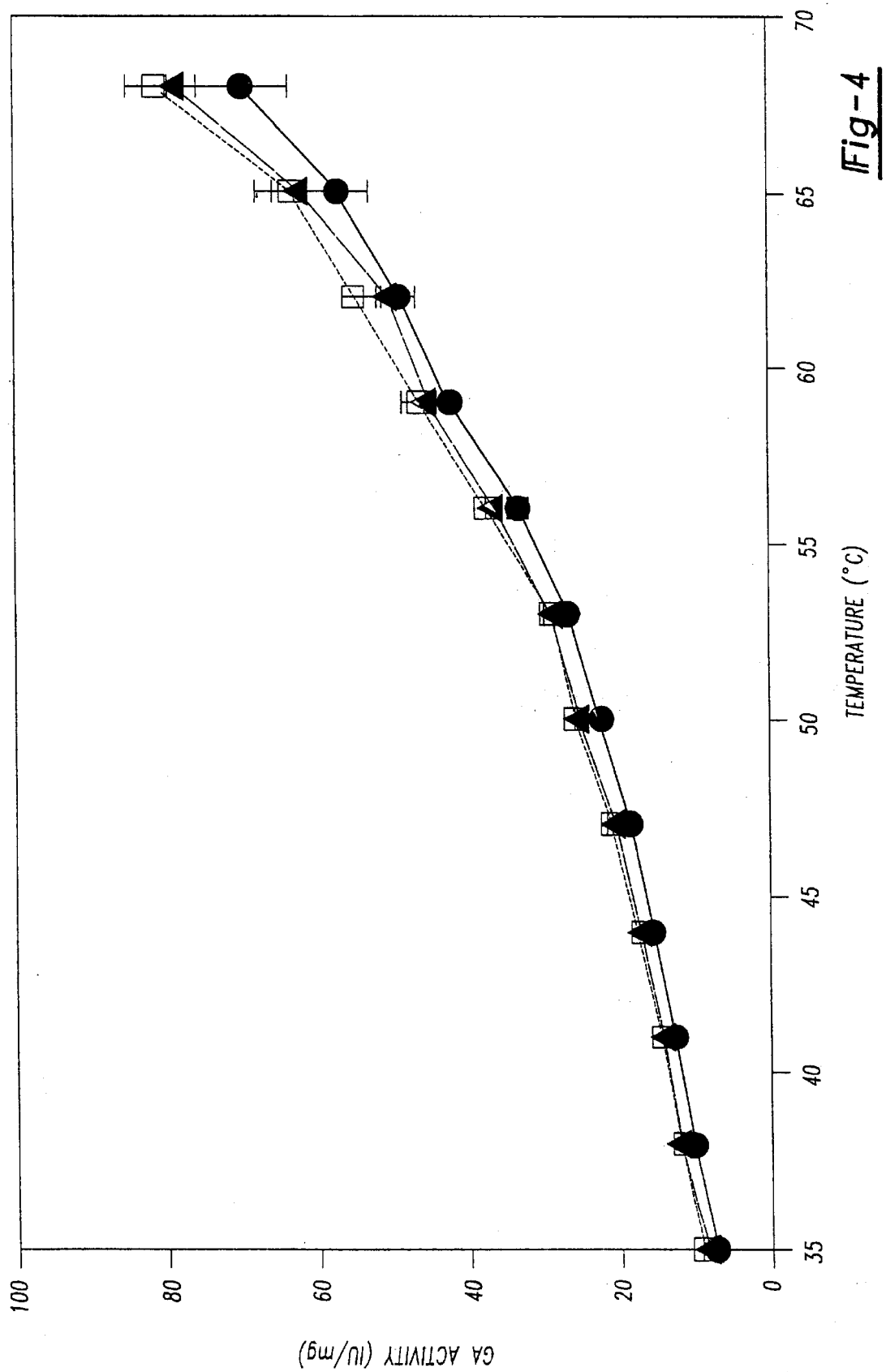
FIG. 4 is a graph showing the effect of temperature on the activity of wildtype and mutant GA. Error bars represent the standard deviation from three assays. Wildtype (●), S30P/G137A (□), S-S/S30P/G137A (▼).

Table 5 shows the specific activities of the wild-type and mutant GAs at 50° C. and pH 4.5 using maltose as substrate. None of the mutant GAs demonstrated reduced enzyme activity and the S30P/G137A and S-S/S30P/G137A mutants were somewhat more active than wild-type at 50° C. To further investigate this observation, the activities of these mutant enzymes were assayed at various temperatures between 35° and 68° C. (FIG. 4). The S30P/G137A and S-S/S30P/G137A mutant GAs were more active than wild-type at all temperatures examined.

Thiol Analysis

The formation of a disulfide bond between positions 20 and 27 in the Asn20→Cys/Ala27→Cys mutant GA has been confirmed (Example 2). Table 6 shows the results of thiol analysis for the combined mutants S-S/S30P and S-S/S30P/G137A. A. awamori GA has one free cysteine at position 320. The combined mutant GAs show slightly higher thiol content per molecule than wild-type which may reflect less than complete disulfide bond formation between positions 20 and 27. However, if the disulfide bond was completely unformed, the [SH]/protein would be expected to rise to approximately three with the addition of two free cysteine residues. Therefore, we conclude that the disulfide bridge is formed at 70–80% the expected theoretical yield for complete formation.

Irreversible Thermal Inactivation

Wild-type and mutant GAs were subjected to thermal inactivation at pH 4.5 between 65° and 80° C. Semilogarithmic plotting of residual activity versus inactivation time yielded inactivation rate coefficients (kd). FIG. 5 shows the effect of temperature on kd for wild-type and mutant GAs. As can be seen, the combined mutants are significantly more stable than the individual mutant enzymes. Additionally, the temperature at which the enzymes were 50% inactivated after 10 minutes (Tm) was calculated by extrapolation from the thermal inactivation plots and transition state theory was used to calculate activation energies for thermal inactivation ($\Delta G^{\ddagger}$). Table 7 shows the changes in $\Delta G^{\ddagger}$ ($\Delta\Delta G^{\ddagger}$) and Tm for the combined mutant GAs relative to wild-type GA. These data clearly demonstrate that combining the individual stabilizing mutations can cumulatively stabilize the enzyme.

Saccharification Analysis

Figure 6A:
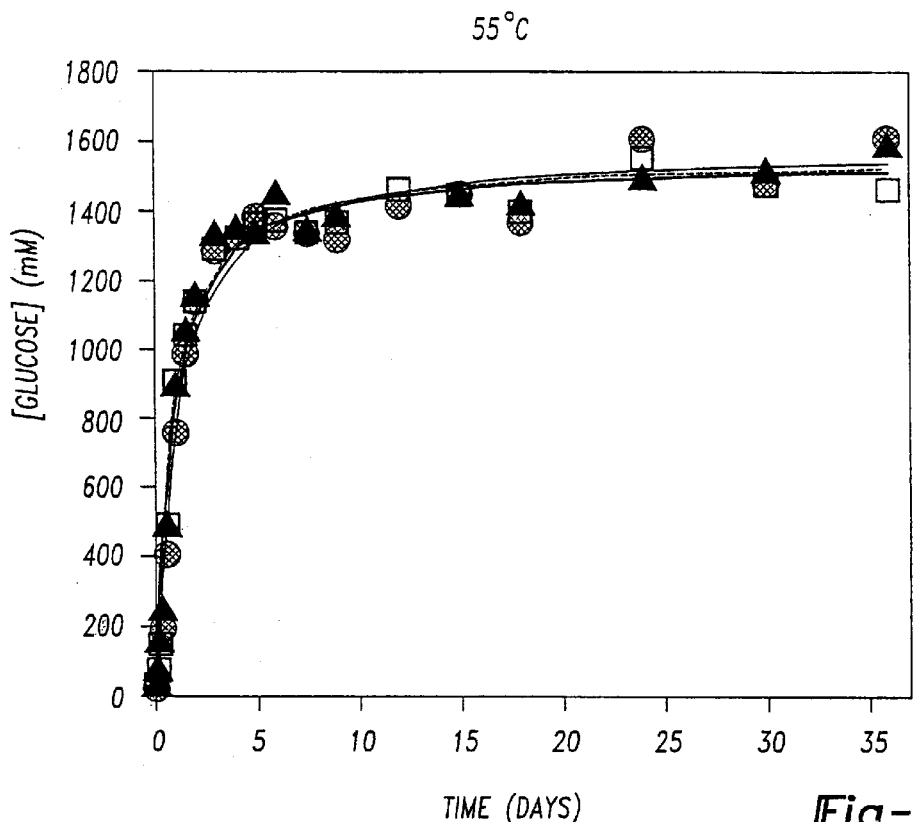
FIGS. 6A–B are graphs showing saccharification of 28% (w/v) Maltrin M100 by wildtype (●), S30P/G137A (□) and S-S/S30P/G137A (▼).
Figure 6B:
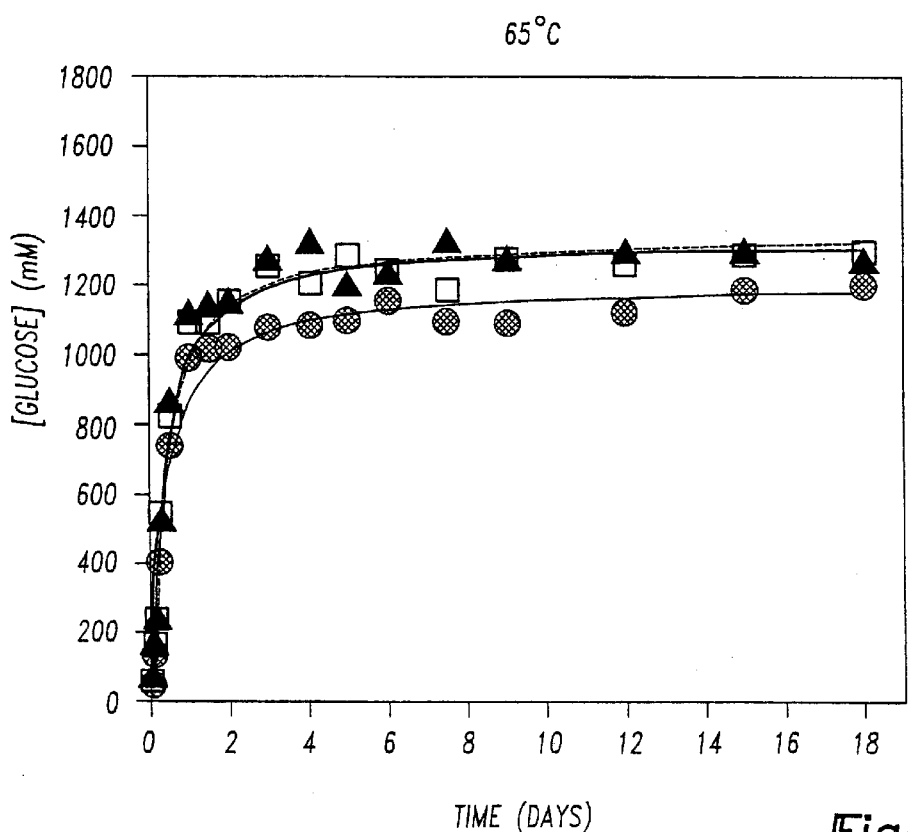

FIG. 6 shows the results of saccharification analysis at 55° and 65° C. for wild-type, S30P/G137A and S-S/S30P/G137A GAs using the industrial DE 10 maltodextrin substrate Maltrin M100 (28% w/v) from Grain Processing Corporation. Complete conversion of 28% w/v DE 10 maltodextrin to glucose would result in a 1.71 M glucose syrup however, previous saccharification analyses in our laboratory have demonstrated that wild-type GA results in approximately 90% theoretical maximum glucose yield at 55° C. (not shown). At 55° C. no significant difference in glucose production was observed between the wild-type and mutant enzymes. However, at 65° C. the mutant GAs produced 8–10% more glucose than wild-type although none of the enzymes tested produced as much glucose as at 55° C. probably due to thermal inactivation at the elevated reaction temperature.

In summary these data show that the S30P/G137A double mutant enzyme was more stable than either single mutant GA when analyzed for resistance to irreversible thermal inactivation between 65° C. and 80° C. The S-S/S30P combined GA mutant was also more stable than either the S30P or the S-S mutant GAs. The S-S/S30P/G137A combined mutant was the most stable GA variant constructed, particularly at temperatures above 70° C. when inactivated in a buffer system lacking mono- or polysaccharides. Saccharification analysis showed that the mutant enzymes performed better at elevated temperatures than wild-type GA. Importantly, none of the combined mutant GAs showed decreased enzyme activity when analyzed at 50° C.

Discussion

Sites of Mutation

As described in Example 2, the mutations Asn20→Cys and Ala27→Cys form a disulfide bond between the C-terminus of $\alpha$-helix one and an extended loop between $\alpha$-helices one and two. S30P and G137A were designed to stabilize the enzyme by reducing its conformational entropy of unfolding and are the most stabilizing in a series of proline substitution (Xaa→Pro) and Gly→Ala mutations respectively. Ser30 is located at the second position of a type II $\beta$-turn on an extended loop between $\alpha$-helices one and two and Gly137 is located in the middle of the fourth $\alpha$-helix.

It is of particular importance to note the positions of the S30P and the disulfide bond forming mutations. The disulfide bond is formed between positions 20 and 27; relatively close to position 30. The fact that both the disulfide bond forming mutations and the S30P stabilize GA suggests that this region of the enzyme is critical for irreversible thermal inactivation and may represent a region of local unfolding important for thermal inactivation. Additionally, previous investigators have suggested that a disulfide bond should not be engineered within four amino acids of a proline in primary sequence [Balaji et al, 1989]. This Example demonstrates that this rule is not absolute since thiol analysis showed that the disulfide bond was formed in the S-S/S30P and S-S/S30P/G137A combined mutants and thermal inactivation studies showed the stabilizing effects of the mutations were cumulative.

Cumulative Stabilization

Previous work by Applicants has shown that combining two stabilizing mutations does not necessarily stabilize GA [Chen et al, 1996]. The present study, however, demonstrates that combining stabilizing mutations, even mutations very close to each other in the protein, can cumulatively stabilize GA as measured by resistance to irreversible thermal inactivation.

Figure 5A:
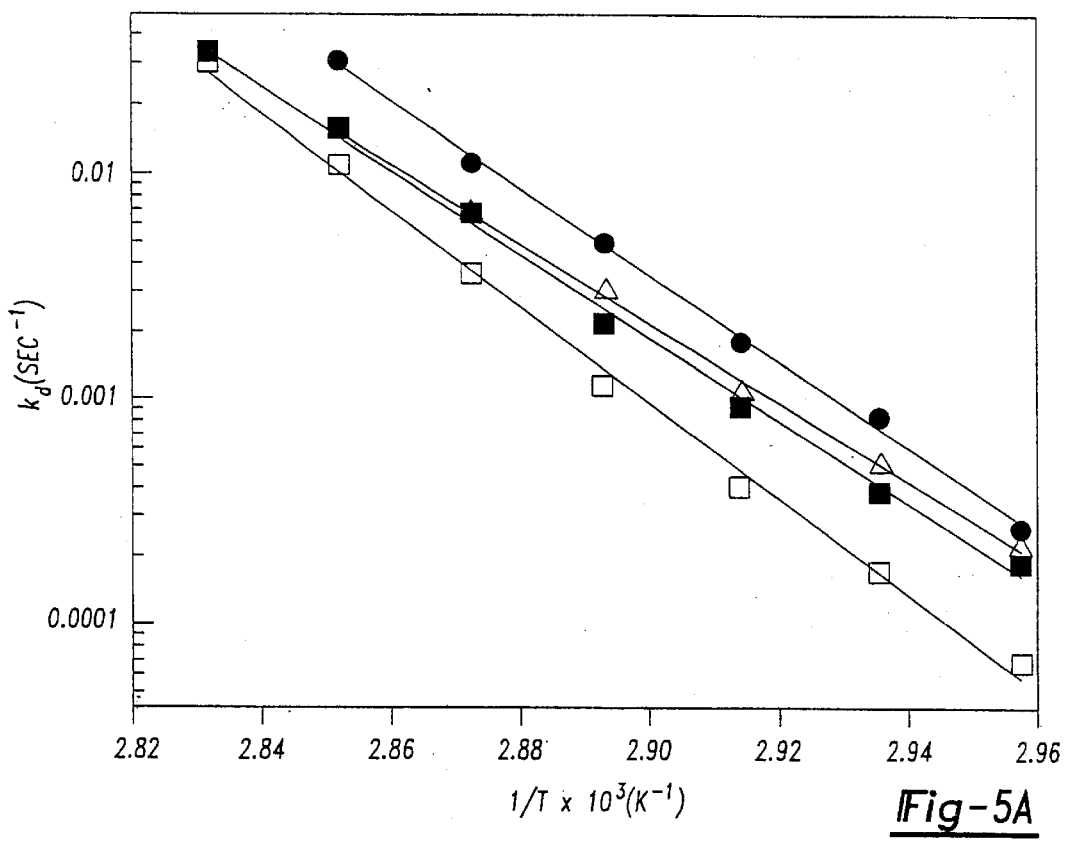
FIGS. 5A–C are graphs showing the effect of temperature on irreversible thermal inactivation rate coefficients of wild-type and mutant GA.

The S30P/G137A mutant showed more than additive stabilization at low temperatures (65–70° C.), but less than additive stabilization at high temperatures (77.5–80° C.) (FIG. 5A and Table 7). At 80° C. the inactivation rate for the S30P/G137A combined mutant was nearly identical to the S30P individual mutant protein. This indicates that both regions are very important for low temperature thermal inactivation, but at high temperatures inactivation became governed by other processes.

Figure 5B:
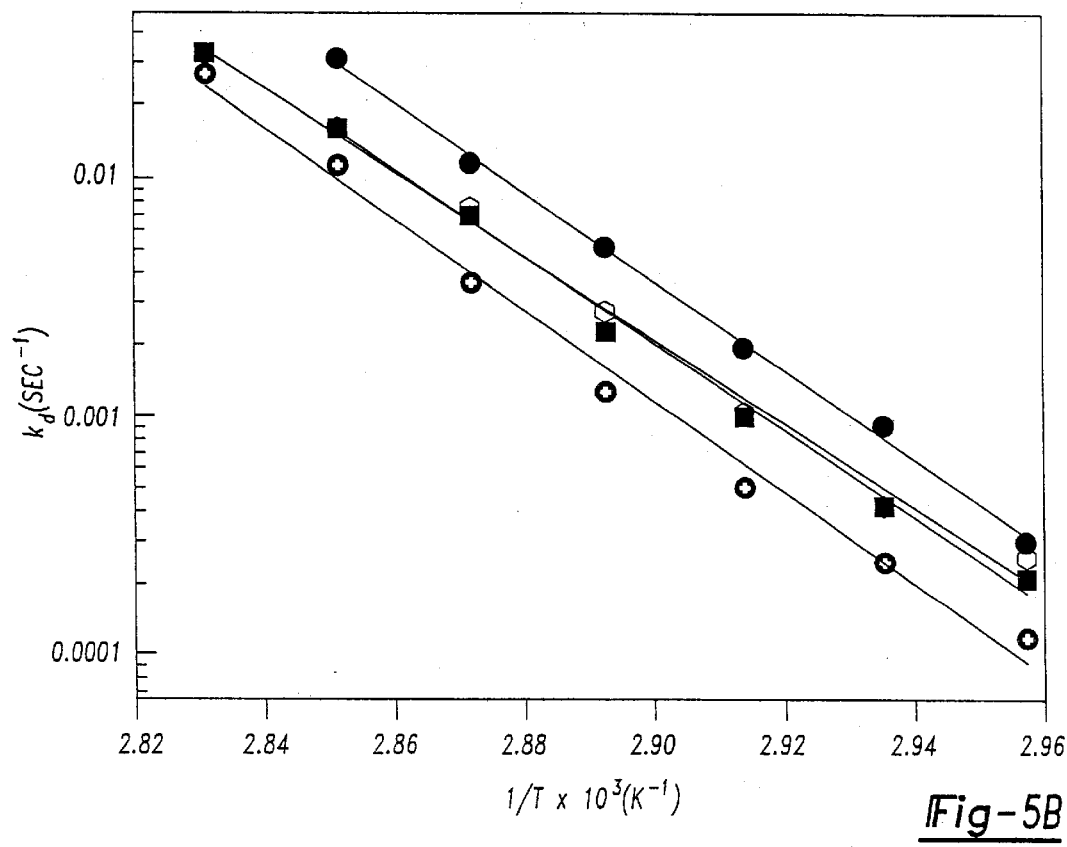

It was somewhat surprising that combining the S30P with the disulfide bond forming mutations resulted in cumulative stabilization. This is not only because the engineered disulfide bond is so close to the engineered proline as is discussed above, but also because both are targeting the same region of the protein (ie: the extended loop between α-helices one and two). It was expected that either the disulfide bond or S30P stabilized this region maximally, and further stabilization at this site would not result in a functionally more stable enzyme. As can be seen in FIG. 5B, this was not the case. Combining the mutations resulted in roughly additive stabilization at all temperatures examined between 65° and 80° C.

Figure 5C:
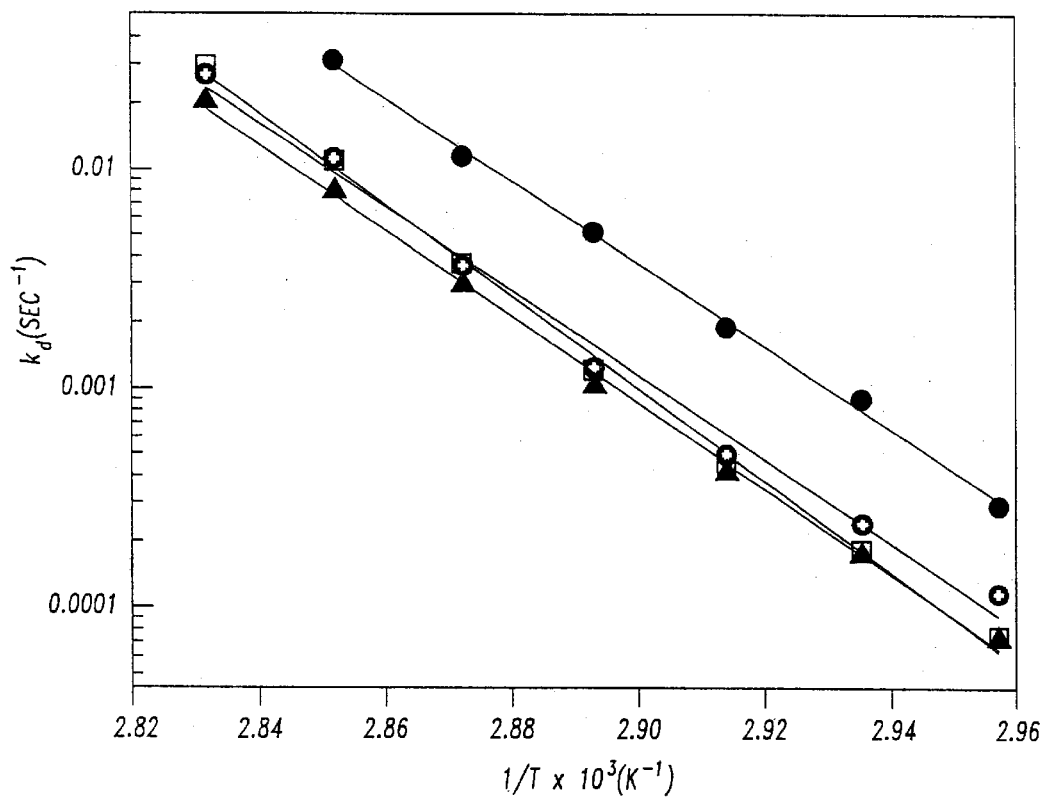

The S-S/S30P/G137A combined mutant was no more stable than S30P/G137A GA at low temperatures (65–70° C.), but was slightly more stable at higher temperatures (75–80° C.) (FIG. 5C and Table 7). Interestingly, the S-S/S30P GA is also more stable than S30P/G137A GA at high temperatures. Therefore, it appears that the introduced disulfide bond is particularly effective at stabilizing GA at high temperatures.

Example 5

Industrial Application

To determine whether the thermal stabilizing mutations: S30P/G137A and S-S/S30P/G137A would enhance GA performance under industrial conditions wild-type and mutant enzymes were subjected to high temperature saccharifications (FIG. 6). Saccharification analysis showed that the mutant enzymes out-performed wild-type at 65° C. but not at 55° C. likely due to their increased stability.

Conclusion

The S30P/G137A double mutant cumulatively stabilized GA as demonstrated by decreased irreversible thermal inactivation rates relative to either individual mutant enzyme when analyzed between 65° C. and 80° C. Similarly, the S-S/S30P combined mutant also demonstrated cumulative stabilization. The S-S/S30P/G137A combined mutant was more stable than either of the "double" mutants, particularly at temperatures above 70° C. The S-S/S30P combined mutant had the same activity as wild-type and the S30P/G137A and S-S/S30P/G137A mutants increased enzyme activity by 10–20% when assayed between 35° and 68° C. The S30P/G137A and S-S/S30P/G137A mutant GAs decreased thermal inactivation rates approximately three fold relative to wild-type when inactivated in the presence of 1.71M glucose at 65° C. Additionally, at 55° C. no difference in glucose yield was observed between these mutant GAs and wild-type for the saccharification of the industrial substrate Maltrin M100, whereas at 65° C. the S30P/G137A and S-S/S30P/G137A GAs produced 8–10% more glucose than wild-type.

Example 6

Mutations with Increased Selectivity

Interactions between substrates and charged residues at subsites 1 and 2 of GA play a very important role in substrate specificity since the catalytic site is located between these sites. Therefore mutations were designed and analyzed to determine residues within these regions where mutations would increase selectivity of the enzyme reaction. In addition, several mutations that were designed to have thermostability were also screened for selectivity, as well as mutations designed to increase the pH optimum.

Site-directed Mutagenesis

Site-directed mutagenesis was performed as described herein above. The following mutagenic oligonucleotide primers were synthesized at the Iowa State University Nucleic Acid Facility: 5'-GGT CTC GGT GAG CCC A<u>GG</u> TTC AAT GTC GAT-3' (Lys108→Arg; SEQ ID No:10), 5'-GGT CTC GGT GAG CCC A<u>TG</u> TTC AAT GTC GAT-3' (Lys108→Met; SEQ ID No:11), 5'-GAG GAC ACG TAC T<u>GG</u> AAC GGC AAC CCG-3' (Tyr312→Trp; SEQ ID No:12), and 5'-TAC CCT GAG GAC ACG TAC <u>AAC GGC AAC GGC AAC TCG CAG</u> GGC AAC CCG TGG TTC CTG TGC-3' (311-314Loop; SEQ ID No:13), the underlined letters indicating the changed or added nucleotides.

Results

Enzyme Kinetics

As shown in table 11, the kinetic parameters $k_{cat}$ and $K_M$ for the hydrolysis of $G_2$ to $G_7$ as well as $iG_2$ in 0.05 M acetate buffer, pH 4.4, at 45° C. are given in Table 8. The 311-314Loop mutant had $k_{cat}$ values 50–80% for all α-(1,4)-linked substrates and only 30% for $iG_2$, $K_M$ values 50–75% for all substrates. The $k_{cat}$ values for Gly137→Ala/Ser30→Pro GA are 10–30% more, generally, than that of wild-type GA for all substrates. The $K_M$ values of Gly137→Ala/Ser30→Pro GA are about half to twofold for all the α-(1,4)-linked substrates and essentially reached the wildtype level for $iG_2$. The $k_{cat}$ values for the GA engineered to carry the triple mutation, S-S/Gly137→Ala/Ser30→Pro, ranged from 80 to 120% generally for all substrates, and the $K_M$ values are 30–80% for all substrates compared to wild-type GA. The $k_{cat}$ values for S-S GA are 85–110% for all substrates, and the S-S GA $K_M$ values are generally 90–110% for all substrates. However, the S-S GA $K_M$ values are 140% for $G_5$ and 190% for $G_6$. Values of $k_{cat}/K_M$ are 75–105%, 60–110%, 60–110%, and 60–120% for the Tyr312→Trp mutation, the combined Ser30→Pro/Gly137→Ala double mutation, the combined S-S/

Ser30→Pro/Gly137→Ala triple mutation, and the S-S engineered GA, respectively. The catalytic efficiencies for the 311-314Loop GA are 85–120% for all the α-(1,4)-linked substrates, and only 50% for iG$_2$, compared to wild-type GA.

Table 8 shows the ratios of the catalytic efficiencies for G$_2$ to iG$_2$ for wild-type and mutant GAs. GAs engineered with the 311-314Loop mutation and Lys108→Arg mutation have the highest (240%) and the lowest (20%) catalytic efficiencies for α-(1,4)- over α-(1,6)-linked substrates, respectively. The GAs engineered with the Tyr312→Trp and S-S mutations show 50% and 20% increases for this ratio, respectively. All other mutants had lower ratios, indicating poorer α-(1,4)-hydrolytic ability relative to α-(1,6)-hydrolytic ability than wild-type GA.

Maltooligosaccharide Hydrolysis

Figure 7:
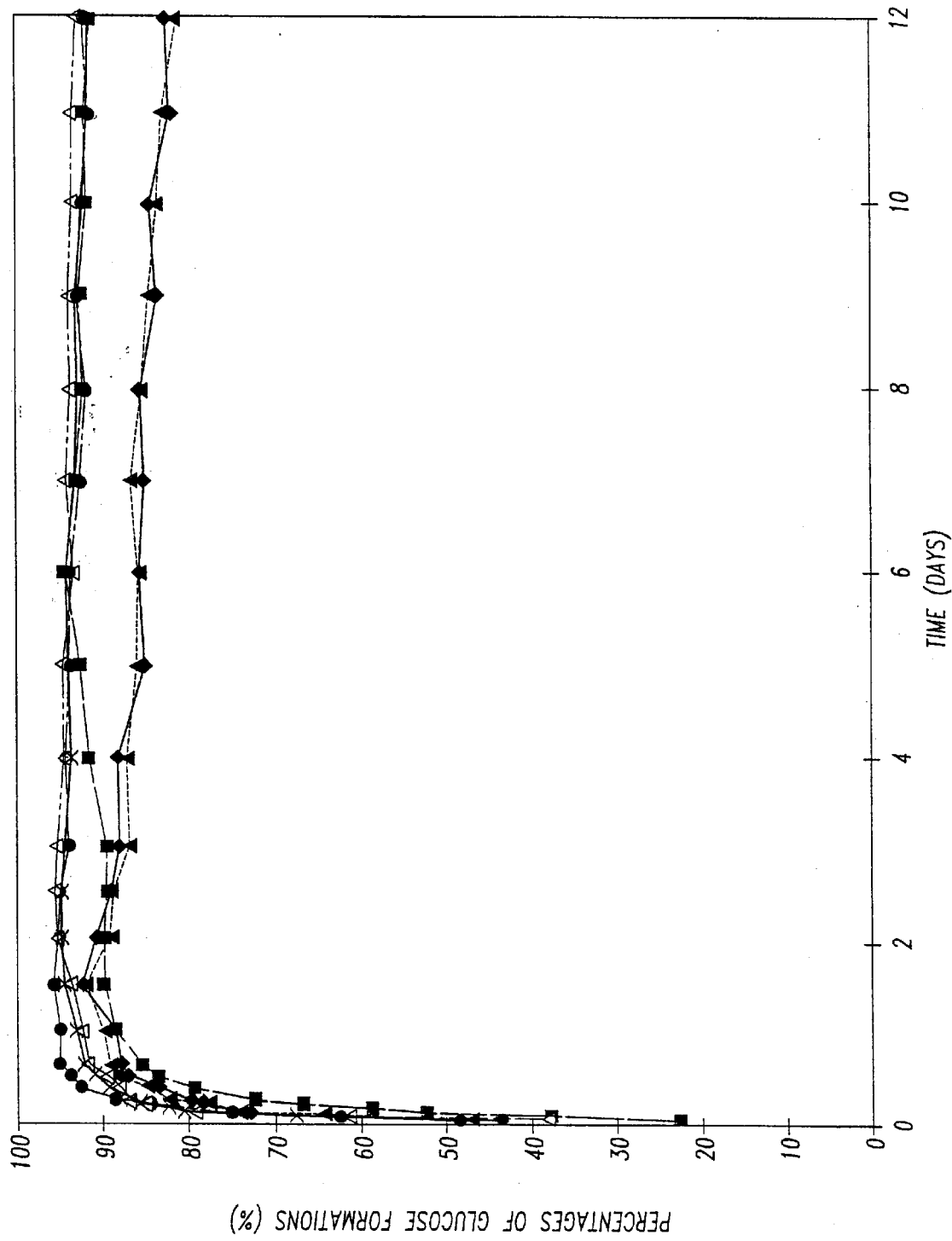
FIG. 7 is a graph showing the 30% DE 10 maltodextrin saccharification of wildtype (◆) and mutant glycoamylases: 300Loop (■), S30P/G137A (▲), S-S (●), S30P/G137A/300Loop (×), S-S/300Loop (_), at 55° C., enzyme concentration was 166.67 μg/mL in each reaction.

GA engineered with the 311-314Loop mutation or with the S-S mutation had the highest average glucose yields (FIG. 7). The 311-314Loop GA had the lowest initial rates for glucose production (64%, 61%, and 82% compared to wild-type GA at 35, 45, and 55° C., respectively) due to a specific activity only 60% that of wild-type GA (data not shown). Glucose concentrations decreased after reaching maximal values because of conversion to oligosaccharides.

Glucose Condensation Reactions

IG$_2$ concentration profiles in 30% (w/v) glucose condensation reactions at 35, 45, and 55° C. were analyzed. GAs engineered with the Lys108Arg mutation had the highest and the 311-314Loop mutation as well as the S-S mutation the lowest equilibrium iG$_2$ concentrations at all three temperatures. Tyr312→Trp, Ser30→Pro/Gly137→Ala, and S-S/Ser30→Pro/Gly137→Ala GAs exhibited essentially the same equilibrium iG$_2$ concentrations as wild-type GA. For all the other engineered thermostable GAs tested, Ser436→Pro, S-S/Ser436→Pro, S-S/Gly137→Ala, and Gly137→Ala/Ser436→Pro, all reached higher equilibrium iG$_2$ concentrations than did wild-type GA. Table 9 shows the initial rates of iG$_2$ formation in 30% (w/v) glucose condensation reactions. S-S and 311-314Loop mutant GAs have the lowest initial rates at all three reaction temperatures tested. Lys108→Arg mutant GA showed the highest initial rates among all the mutant GAs tested at all three reaction temperatures. All the tested thermostable GAs except Ser30→Pro/Gly137→Ala and S-S/Ser30→Pro/Gly137→Ala had much higher initial rates than wild-type GA at 35° C., but they dropped to slightly higher or almost the same rate as wild-type GA at 55° C.

The Specificity for a-(1,6)-linkage Synthesis over a-(1,4)-linkage Hydrolysis

The ratio of the initial rate of iG$_2$ production in a 30% (w/v) glucose condensation reaction to that of glucose formation in 30% DE 10 maltodextrin hydrolysis was calculated to estimate the selectivity for the synthesis of α-(1,6)-linked products over the hydrolysis of α-(1,6)-linked substrates. These iG$_2$/glucose ratios and their relative ratios for wild-type and mutant GAs are given in Table 9. K108R and S-S mutants showed the highest and the lowest relative ratios among wildtype and all the mutant GAs at all reaction temperatures, respectively. Therefore, K108R had more specificity for α-(1,6)-linkages than α-(1,4)-linkages and S-S GA had more affinity for α-(1,4)-linkages than α-(1,6)-linkages. The 311-314Loop GA also showed very low relative ratios at these three temperatures.

Example 7

Additional Selectivity Mutation Analysis

Utilizing the methods as set forth herein above, additional mutations were screened for selectivity as shown in Table 10 and FIGS. 8 and 9.

Enzyme Kinetics

The kinetic parameters are seen in ($k_{cat}$ and $K_m$) for the hydrolysis of α-1,6-linked isomaltose and α-1,4-linked maltooligodextrins (DP2-7) at 45° C. and pH 4.4 are given in Table 10. Mutant Y175F was active. The $k_{cat}$ and $K_m$ values were 83–141% and 106–171%, respectively, that of wild-type for the different substrates tested and catalytic efficiencies were 69–102% that of wildtype. Mutant R241K was also active. Mutant S411G was highly active. The $k_{cat}$ and $K_m$ values were 93–129% and 83–203%, respectively, that of wildtype for the different substrates tested and catalytic efficiencies were 55–122% that of wildtype. Mutant S411A had a similar catalytic efficiency ratio as wildtype. Mutants Y116W, R241K, and S411G had decreased catalytic efficiency ratios compared to that of wildtype GA.

DE 10 Maltodextrin Hydrolysis

Figure 9:
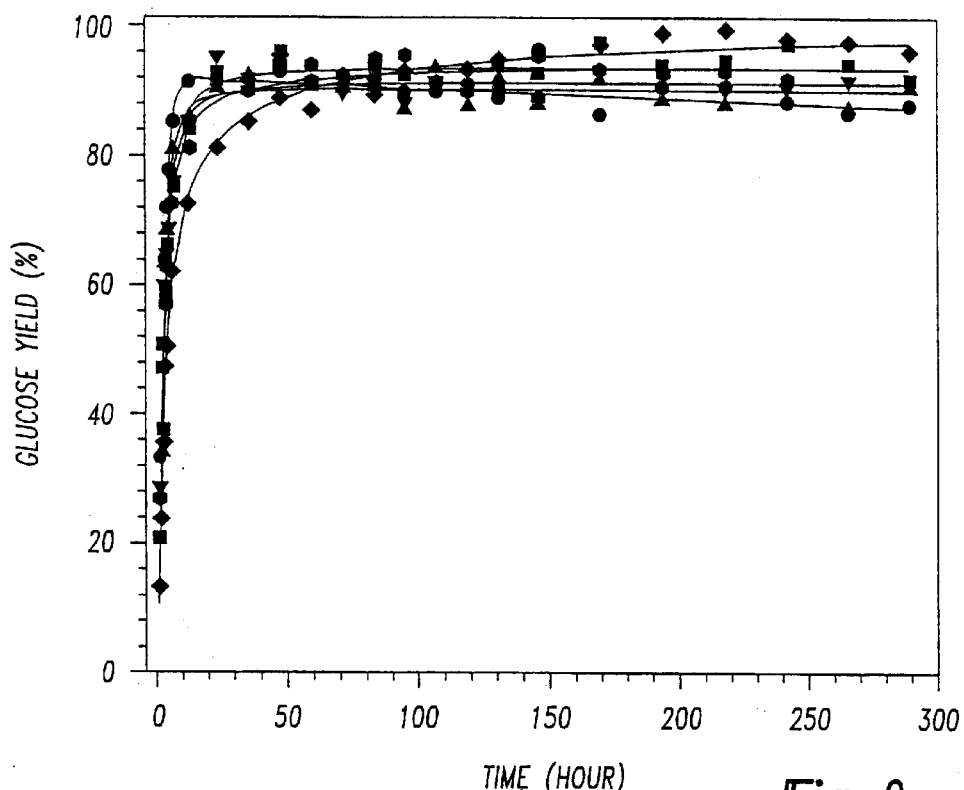
FIG. 9 is a graph showing the production of glucose by wildtype (●) and mutant glucoamylases: Y116W (■), Y175F (▲) R241(▼) S411A (◆), S411G (hexagon), during hydrolysis of DE 10 maltodextrin at 55° C. with 28% (w/v)

At 55° C., the highest glucose yield was about 95% reached by engineered GA with mutant S411A at 216 hours compared to the wildtype yield of about 90% (FIG. 9). All of the GAs, except S411A, reached their highest glucose yields rapidly. The glucose yield of S411A slowly increased for an extended period of time. The initial rates of glucose production at 55° C. were 5 to 8 times higher that those at 35° C.

Glucose Condensation Reaction

Figure 8:
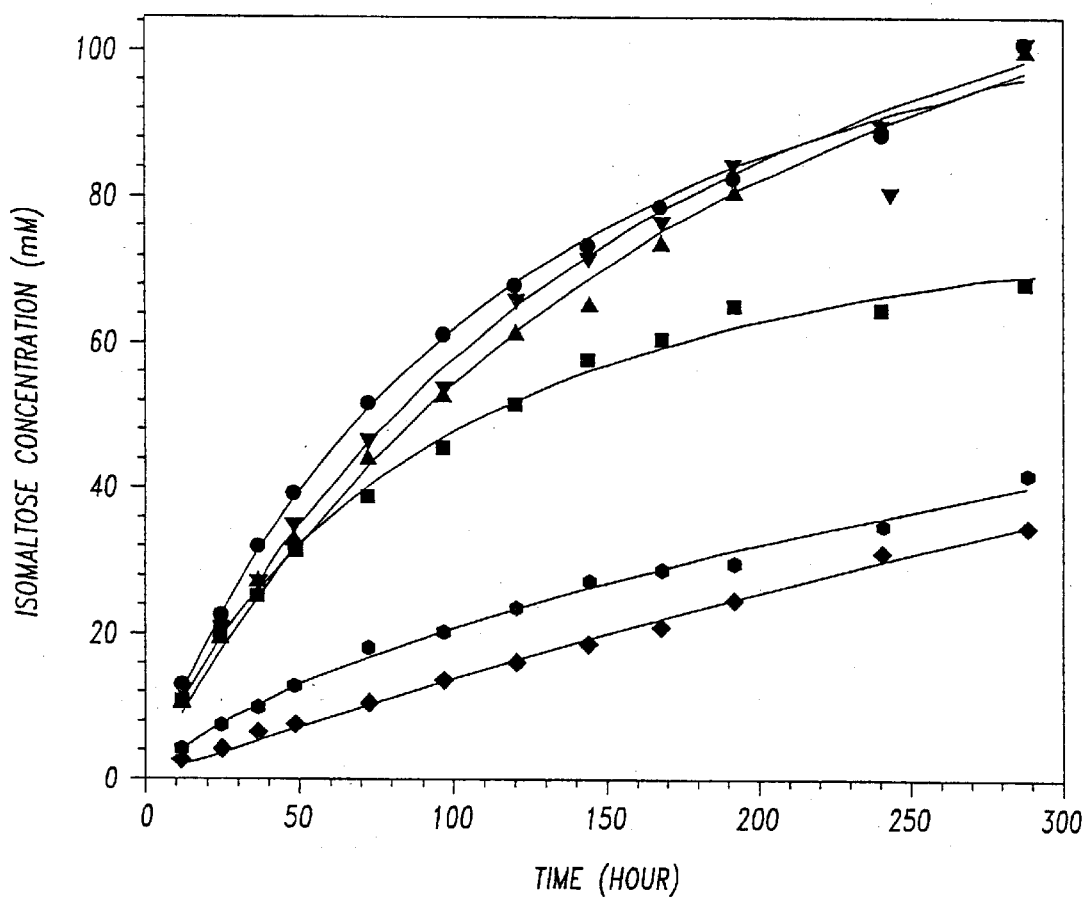
FIG. 8 is a graph showing production of isomaltose by wildtype (●) and mutant glucoamylases: Y116W (■), Y175F (▼), R241K (▼) S411A (◆), S411G (hexagon), during glucose condensation at 55° C. with 30% (w/v) D-glucose in 0.05M sodium acetate buffer at pH4.4 with 0.02% sodium azide for 12 days.

Glucose condensation reactions were used to study the ability of wildtype and mutant GAs to synthesize isomaltose at high glucose concentrations (FIG. 8). The same concentrations of glucoamylases (2.64 μM) were used as in the hydrolysis of DE 10 Maltodextrin.

At 55° C., in spite of the different initial rates of isomaltose production for wildtype, R241K and Y175F, isomaltose production reached almost the same concentration at the last time point for these three mutant GAs (FIG. 8), indicating that the isomaltose production was close to equilibrium status. Isomaltose production for S411A and S411G was much lower than wildtype and almost linear as it was also at 35° C. Unexpectedly, isomaltose production for Y116W had a different (lower) equilibrium status compared to wildtype. The initial rates of isomaltose production at 55° C. were 5 to 7 times greater than those at 35° C. R241K had a decreased initial rate of isomaltose production at 55° C. compared to that of wildtype, and it also had a lower increase (about 5 times) in the initial rate of isomaltose production from 35° C. to 55° C., compared to the wildtype increase (about 7 times). Y116W, Y175F, S411A and S411G had increased initial rates of isomaltose production or about 7, 6, and 5 times, respectively from 35° C. to 55° C.

Selectivity

The ratio of the initial rate of isomaltose production (from glucose condensation reactions) to that of glucose production (from hydrolysis of DE 10 maltodextrin) was calculated to evaluate selectivity for the synthesis of α-1,6-linked products versus the hydrolysis of α-1,4 linked substrates. This ratio represents the ability of a GA to synthesize isomaltose at a normalized level of DE 10 maltodextrin hydrolytic activity.

Mutants Y175F, S411A and S411G had a decreased ratio of the initial rate of isomaltose production to that of glucose production to that of glucose production by 12%, 35% and 56% at 35° C., respectively, and a decreased ratio by 24%, 60% and 62% at 55° C., respectively, compared to wildtype. R241K had a very similar ratio to that of wildtype at both 35° C. and 55° C.

Example 8

Mutations to Provide pH Optimization

Utilizing the methods as set forth herein above, additional mutations, S411G, S411A, S411C, S411H, S411D were screened for increased pH optimum as shown in FIG. 10 and Tables 11 and 12.

Enzyme Kinetics

The kinetic parameters, $k_{cat}$ and $K_m$, for the hydrolysis of α-1,4-linked maltose and maltoheptaose and α-1,6-linked isomaltose at 45° C. and pH 4.4 are given in Table 11. Mutant S411G glucoamylase was highly active compared to wild-type, with an increased $k_{cat}$ and $K_m$ 13–30% and 11–59%, respectively, on the substrates tested. The catalytic efficiencies ($k_{cat}/K_m$) were 71–116% that of wild-type. Mutant S411A maintained 65–74% of wild-type catalytic efficiency with a slightly decreased $k_{cat}$ and a slightly increased $K_m$. Mutant S411C maintained 54–73% of wild-type catalytic efficiency with a decrease in both the $k_{cat}$ and $K_m$ values. Since mutant S411H and S411D had only about 6–12% of wild-type catalytic efficiency resulting from a seriously decreased $k_{cat}$ and an increased $K_m$, the kinetic parameters for the hydrolysis of isomaltose were not determined. Only mutant S411H and S411D had large increases (5.5 to 7.5 kJ/mol) in the transition-state energy, $\Delta(\Delta G)$, for the hydrolysis of maltose and maltoheptaose. The large increases of transition-state energy indicated that the introduction of histidine or aspartic acid into position 411 substantially destabilized the binding between GA and substrate in the transition-state.

pH Dependence of GA Activity

The kinetic parameters, $k_{cat}/K_m$ and $k_{cat}$, of the hydrolysis of maltose by wild-type and mutant glucoamylases at different pH values were calculated from initial rates obtained at low (smaller than 0.2 $K_m$) and high (higher than 10 $K_m$) concentrations of maltose. The effects of pH on the $k_{cat}/K_m$ and $k_{cat}$ of maltose hydrolysis were used to determine the pK values (Table 12) of both the free enzymes and the enzyme-substrate complexes. Although wild-type GA had a higher catalytic efficiency ($k_{cat}/K_m$) than all of the mutant glucoamylases at all of the pH values tested, mutants S411G and S411A had higher $k_{cat}$ values than that of wild-type at some pH values. The uncomplexed and maltose-complexed S411H and S411D showed more narrow bell-shaped curves than that of wild-type.

The effects of pH on the hydrolysis of maltoheptaose by wild-type, S411G and S411A GAs were measured to further investigate the change of pK values and optimum pH of enzyme-substrate complexes using a long-length substrate. Surprisingly, not only S411G, but also S411A were highly active compared to wild-type at the optimum pH. Wild-type GA pK1 values (ionization of the catalytic base) were 2.77, 2.11, and 2.6 for the free enzyme, the maltose-complexed form, and the maltoheptaose-complexed form, respectively. The $pK_2$ values (ionization of the catalytic acid) of wild-type were 5.80, 5.85, and 6.78 for the free enzyme, the maltose-complexed form, and the maltoheptaose-complexed form, respectively [Bakir et al., 1993, Hiromi et al., 1966, Sierks and Svensson, 1994]. Compared to wild-type, the S411G mutation increased the pK1 of both the maltose-complexed form and the maltoheptaose-complexed form by approximately 0.6 units, whereas S411G had no effect on the pK2 of either enzyme-substrate complexes and only had a minor effect on the pK1 and pK2 of the free enzyme. The combined effect of S411G on pK1 and pK2 was an increased optimum pH of both the maltose-complexed form and the maltoheptaose-complexed form by approximately 0.3 units.

The S411G mutation, however, had no effect on the optimum pH of the free enzyme. S411A and S411C had very similar effects on the pH dependence of maltose hydrolysis. S411A and S411C increased the $pK_1$ of the free enzyme and the maltose-complexed forms by 0.3–0.5 and 1.21 units, respectively. Surprisingly, S411A and S411C also increased the $pK_2$ of the maltose-complexed form by approximately 0.5 units. In addition, S411A increased the $pK_1$ and $pK_2$ of the maltoheptaose-complexed form by 1.31 and 0.4 units, respectively. S411H increased the $pK_1$ of the free enzyme and maltose-complexed form by 0.33 and 1.47 units, respectively; however, it decreased the $pK_2$ of the free enzyme and the maltose-complexed form by 0.79 and 1.16 units, respectively. S411D increased the pK1 of the free enzyme and the maltose-complexed form by 0.36 and 1.23 units, respectively. S411D also decreased the $pK_2$ of the maltose-complexed form by 0.32 units. For wild-type, S411G, and S411A GAs, the values of $pK_1$, $pK_2$, and $pH_{opt}$ for the maltoheptaose-complexed forms were higher than those of the corresponding maltose-complexed forms by approximately 0.5, 0.9 and 0.7 units, respectively. For S411G and S411A, the increases in pH optimum (compared to that of wild-type) obtained using the long-length substrate (maltoheptaose) were almost the same as that obtained using the short-length substrate (maltose).

All five mutants at position 411 showed a shift of 0.15 to 0.87 units in the optimum pH of the enzyme-substrate complex compared to wild-type (Table 12), mainly due to increased $pK_1$ values. Compared with other mutants, S411A was the best performing pH mutant. S411A increased the optimum pH by 0.84 units while also maintaining a high level of both catalytic activity ($k_{cat}$) and catalytic efficiency ($k_{cat}/K_m$).

The Hydrolysis of Maltodextrin 10

The hydrolysis of 28% (w/v) maltodextrin was used to study the pH dependence of GA activity at a high concentration of a long-length substrate. Maltodextrin 10 is a mixture of maltodextrin with an average (and major) degree of polymerization of 10. The production of glucose by wild-type and S411A glucoamylases during the hydrolysis of maltodextrin 10 at 11 different pH values was determined, and used to calculate the initial rates of glucose production at different pH values (FIG. 10). The production of glucose increased following a hyperbolic curve. S411A had higher initial rates of glucose production than wild-type when the pH values were above 6.6 (FIG. 10).

Example 9

Additional Selectivity Mutation Analysis

Materials and Methods

Methods for enzyme production and purification, protein concentration determination, 30% (w/v) maltooligosaccharide hydrolysis and 30% (w/v) glucose condensation reactions were described by Fang et al. (1998a). Specific activities were measured as by Fang et al.

Glucose and maltose were obtained from Sigma. Maltrin® M100, M180 and M250 maltodextrins, of DE 10, 18, and 25, respectively, and with average degrees of polymerization of 10, 6, and 4, were donated by Grain Processing Corporation. Other materials were as in Fang et al. (1998a).

Site-directed Mutagenesis

The Gly137→Ala (Chen. et al., 1996), Ser436→Pro (Li et al., 1997), SS, SS/Gly137→Ala, SS/Ser436→Pro, Gly137→Ala/Ser436→Pro (Li et al., 1998), Ser411→Ala (Fang and Ford, 1998), 311-314Loop (Liu et al., 1998), Ser30→Pro, SS/Ser30→Pro, Ser30→Pro/Gly137→Ala and SS/Ser30→Pro/Gly137→Ala (Allen et al., 1998). GAs were constructed as described earlier.

Site-directed mutagenesis to produce nine multiple mutations was performed by Promega Altered Sites II in vitro mutagenesis system.

For the 311-314Loop/Ser411→Ala mutation, an XbaI-HindIII fragment of pGEM-GA containing the wild-type GA cDNA (Fang and Ford, 1998) was inserted into the Promega pALTER-1 vector to make a GA cDNA-containing vector to be used as the double-stranded DNA template (Fang et al., 1998b). The previously made 311-314Loop mutation containing GA cDNA in the pALTER-1 vector was used as a template, using the oligonucleotide primer 5'-GGC GAG CAG CTT GCA GC<u>A</u> CGC GAC CTG AC-3' (Fang et al., 1998a) synthesized in the Iowa State University Nucleic Acid Facility. Nucleotides for the desired GA mutation are in bold, while the one silent mutation designed to decrease the primer hairpin melting temperature is underlined.

For the other eight multiple mutations, the short BamHI-PstI fragments containing the SS, Ser30→Pro, Gly137→Ala or Ser30→Pro/Gly 137→Ala mutations, which were restriction-digested from the phagemid vector pGEM7Z(+), were separately ligated to the long BamHI-PstI fragments containing the 311-314Loop or Ser411→Ala mutations, which were restriction-digested from the phagemid vectors pGEM7Z(=) and pALTER-I, respectively.

The resulting multiple mutations were verified by DNA sequencing, cDNAs containing the multiple mutations were subcloned into the yeast expression vector YEpPM18 and then transformed into *Saccharomyces cerevisiae* C468 as previously described (Chen et al., 1994).

Irreversible Thermoinactivation

Wild-type and mutant GAs (0.475 µM) were incubated for 12 minutes in 0.05 M NaOAc buffer, pH 4.4, at six or seven temperatures between 65 and 80° C. Samples were taken at two minute intervals, quickly chilled on ice, and then stored at 4° C. for 24 hours before being subjected to residual activity assay at 35° C. as in Liu et al. (1998). The first-order inactivation rate coefficients ($k_d$) for mutant and wild-type GAs were obtained from a plot of ln (residual activity) vs. inactivation time. The transition-state free energies ($\Delta G^{\ddagger}$) for thermoinactivation of mutant and wild-type GAs were obtained from a plot of in ($k_d/TI$) vs $1/T$. The function $\Delta\Delta G^{\ddagger}$ is the difference between $\Delta G^{\ddagger}$ values for mutated and wild-type GAs, being positive when the mutated GA is more stable.

Results

Specific Activities

The specific activities of mutated and wild-type GAs at 50° C. and pH 4.5 using 4% maltose as substrate are shown in Table 16. Data were gathered here and taken from earlier work. Two observations may be made: 1) If single mutations yield GAs with specific activities near that of wild-type GA, then multiply-mutated GAs containing those mutations have specific activities higher than those of any of the GAs with the single mutations, specifically 311-314Loop and Ser411→Ala, yield GAs with very low specific activities compared to wild-type GA, then multiply-mutated GAs containing those mutations usually have slightly higher specific activities than does the GA with the single mutation giving the lowest specific activity.

Maltodextrin Hydrolysis

Glucose formation from 30% (w/v) DE 10 maltodextrin hydrolyses at 55° C. with 1.98 µM wild-type and mutated GAs are shown in FIG. 2. Data (not shown) for DE 18 and DE 25 maltodextrin hydrolyses are similar, while hydrolyses at 35 and 45° C. are slower but are also essentially similar. Glucose concentrations decrease after reaching their maximal values because of reverse reactions to form di- and oligosaccharides, especially at higher temperatures.

Peak glucose yields averaged over the three substrates are shown in Table 16 for all three temperatures. Most GAs with multiple mutations give higher peak glucose yields than does wild-type GA, but those containing the Ser436→Pro mutation have lower yields.

Initial glucose formation rates appear in Table 17. Most multiply-mutated GAs except for those containing the Ser411→Ala mutation have rates similar to or higher than those of wild-type GA. There are relatively few significant differences in initial glucose formation rates among DE 10, 18 and 25 maltodextrins. Specific activities and initial rates on DE 25 maltodextrin are positively correlated, with R values ranging from 0.70 to 0.75 depending on the temperature.

Activation energies, obtained by plotting ln (initial rate) versus $1/T$, average 81 kJ/mol for 30% (w/v) maltodextrin hydrolyses from 35 to 55° C. over different substrates and different mutated and wild-type GAs. Again, there are no significant differences between among substrates. Activation energies for wild-type and all multiply-mutated GAs are within the 95% confidence range, meaning that there is a 95% probability that the values are not significantly different, and suggesting that all mutated GAs catalyze the same hydrolysis mechanism as does wild-type GA.

Glucose Condensation Reactions

Figure 3:
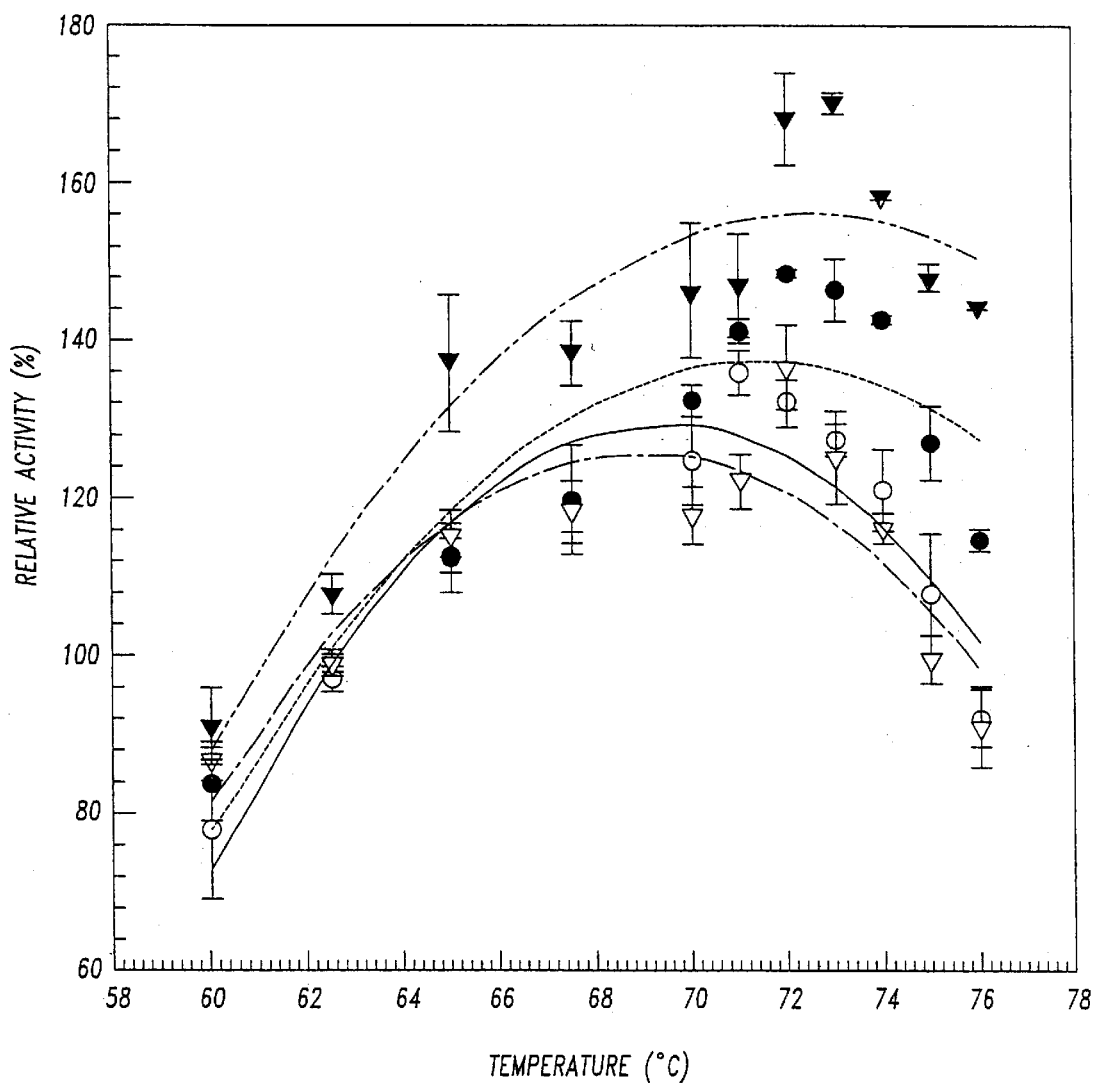
FIG. 3 is a graph showing initial reaction rates of wild-type (○), A27C/N20C (●), A471C/T72C (▽) and A29C/N20C/G137A (▼) glucoamylases with 4% maltose in 0.05 M sodium acetate (pH 4.5) as substrate at temperatures from 60° C. to 76° C.

Formation of $iG_2$ from condensation of 30% (w/v) glucose at 55° C. with 1.98 µM GA is shown in FIG. 3. Reaction profiles at 35 and 45° C. are similar but slower, except that $iG_2$ formation rates with wild-type GA decrease more sharply with decreasing temperature than with other GAs. Initial rates appear in Table 17. Of the GAs with multiple mutations, SS/Ser411→Ala, SS/311-314Loop and 311-314 Loop/Ser411→Ala GAs have the lowest initial rates at all reaction temperatures, while Gly137→Ala/Ser436→Pro and SS/Ser436→Pro GAs have the highest initial rates.

Activation energies, obtained as above, for isomaltose formation of all multiply-mutated GAs, averaging 66 kJ/mol and all within the 95% confidence range, are much lower than that of wild-type GA (90 kJ/mol), meaning that the GAs with multiple mutations may undergo different active-site conformational changes than does wild-type GA while catalyzing the condensation reaction.

Selectivity for α-1,6-linked Product Synthesis Versus α-1, 4-linked Substrate Hydrolysis Ratios of the initial rate of $iG_2$ formation from 30% (w/v) glucose condensation reactions to that of glucose formation from 30% (w/v) DE 10, 18 and 25 maltodextrin hydrolyses were determinated for mutated and wild-type GAs at 35, 45 and 55° C. (Table II). Of the multiply-mutated GAs, SS/314–317 Loop, SS/Ser411→Ala GAs have the lowest ratios while Gly137→Ala/Ser436→Pro and SS/Ser436→Pro GAs have the highest ratios at all reaction temperatures. These ratios are plotted against peak glucose yields in FIG. 4. Yields are slightly higher at 35° C. than at 45 and 55° C., and are slightly higher for DE 25 than for DE 10 and DE 18 maltodextrins. Linear correlations were obtained. Seven of the nine curves had stadard errors by linear regression less than 10% of the values of their corresponding slopes, while the other two (DE 25 maltodextrin at 45 and 55° C.) gave standard errors that were less than 20% of their slopes. This is compelling evidence that variation of glucose yields with different conditions is significant.

Irreversible Thermoinactivation

Table 16 shows the changes of $\Delta G^{\ddagger}$ from that of wild-type GA ($\Delta\Delta G^{\ddagger}$) at 65 and 75° CV, with data taken here and elsewhere. A rough approximation is that $\Delta\Delta G^{\ddagger}$ values of 1 and $-1$ kJ/mol correspond to about 1 and $-1°$ C. changes in operating temperature, respectively, to maintain the same enzyme stability. The Ser30→Pro/Gly137→Ala and SS/Ser30→Pro/Gly137→Ala mutations increase GA thermostability the most, while the 311-314Loop/Ser411→Ala mutations decreases thermostability the most.

Values of $\Delta\Delta G^{\ddagger}$ for GAs with multiple mutations can be approximately determined by adding the $\Delta\Delta G^{\ddagger}$ values of GAs containing their single mutations, as found earlier (Allen et al., 1998; Li et al., 1998). In addition, specific activities at 50° C. and thermostabilities at 65° C. are positively correlated (R=0.85).

Discussion

GA selectivity has been improved by single mutations (Sierks and Svensson, 1994; Svensson et al., 1995, Fang et al., 1998a, b; Liu et al., 1998), loop replacements (Fierobe et al., 1996), and loop insertions (Liu et a., 1998), but there had been no research until this study on the effect of multiple mutations on GA selectivity, except for that of Gly121→Ala/Ser411→Gly GA (Fang et al., 1998b). In this study, GAs were tested with multiple mutations for their selectivities and compared them with all the GAs containing their single mutations to check of the principle of additive mutational effects in proteins also can be applied to GA selectivity.

The strategy of additive mutagenesis has been one of the most powerful and successful tools in stabilizing proteins against irreversible thermoinactivation, such as with $\lambda$ repressor (Hecht et al., 1986), subtilisin (Cunningham and Wells, 1987; Pantoiiano et al., 1989), kanamycin nucleotidyl-transferase (Liao et al., 1986), T4 lysozyme (Matsumura et al., 1989) and GA (Allen et al., 1998); Li et al., 1998); in engineering subtilisin selectivity (Russell and Fersht, 1987); Wells et al., 1987a,b); in improving glutathione reductase coenzyme selectivity (Scrutton et al., 1990); and in enhancing the catalytic efficiency of a weakly active subtilisin variant (Carter et al., 1989). This principle can be expressed as $\Delta\Delta G_{X,Y}=\Delta\Delta G_X+\Delta\Delta G_Y+\Delta G_I$, where $\Delta\Delta G_X$, $\Delta\Delta G_Y$ and $\Delta\Delta G_{X,Y}$ are the free energy changes associated with the measured variables for the single mutations X and Y and the multiple mutation X,Y, respectively (Ackers and Smith, 1985). The coupling energy $\Delta G_I$ (Carter et al., 1984) is the free energy of interaction between sites X and Y. When the side chains at sites X and Y are remote from one another and there are no large structural perturbations or changes in the reaction mechanism or rate-determining step, $G_I$ is negligible and the above equation can be simplified to $\Delta\Delta_{X,Y}=\Delta\Delta G_X+\Delta\Delta G_Y$. The increase of glucose yield for a mutated GA over that of wild-type GA instead of the change in transition-state energy to show the cumulative effect on GA selectivity was used, since the main purpose here was to achieve higher glucose yields by combing mutations.

The cumulative effects on the incremental glucose yield and initial rate ratio of $iG_2$ to glucose formation by various combinations of SS, Ser30→Pro, Gly137→Ala, 311-314Loop, Ser411→Ala and Ser436→Pro mutations are demonstrated in FIGS. 5–9, all at 35, 45 and 55° C. but with results for DE 10, 18 and 25 maltodextrins averaged. In general the multiply-mutated GAs have initial rate ratios between those of the individual mutations of which they are comprised. Increases of glucose yield by multiple mutations are roughly additive, demonstrating the validity of the additivity principle, but are smaller when the incremental glucose yields of both the original mutated GAs are already very high than when they are lower. This means that some limitations occur in increasing glucose yield by mutating GA. For example, byproducts such as maltulose [α-D-glucopyranosyl-(1→4)-D-fructose] produced during maltodextrin production prevent glucose yield from being complete, and decreasing the ability of GA to synthesize $iG_2$ by mutation also limits hydrolysis of α-1,6 bonds found in maltodextrins, resulting in less complete substrate conversion at peak glucose yields.

Before this series of articles, GA selectivities were determined as the ratios of catalytic efficiencies for maltose hydrolysis over $iG_2$ hydrolysis, and these were measured at low substrate concentrations. However, Fang et al. (1998 a,b) and Liu et al. (1998) found that this ratio is not directly related to glucose yield, and instead correlated the latter with the ratio of initial $iG_2$ formation rate to initial glucose formation rate at high substrate concentrations. We have done the same here.

The SS mutation introduced an extra disulfide bond on the catalytic domain surface in the extended loop between the first and second α-helices of GA. This loop, containing a conserved region involved in substrate binding (Coutinho and Reilly, 1997), is near another loop containing residue Trp120, which is critical for catalysis (Sierks et al. 1989) and important in directing conformational changes controlling the putative rate-limiting product release step (Natarajan and Sierks, 1996). The loop appears to be important for both GA thermostability (Li et al., 1998) and selectivity (Liu et al., 1998). The SS mutation may stabilize either or both the loops, thus stabilizing the functional conformation.

The SS mutation had been previously combined with other single mutations to investigate their additive effects on GA thermostability (Allen et al., 1998, Li et al., 1998). Those mutations plus the SS/311-314Loop and SS/Ser411→Ala GA mutations made here show that the SS mutation has a neutral effect on specific activities, except for the SS/Ser436→Pro mutation, when it has a positive effect (Table 16). It increases glucose yields and initial glucose formation rates both by itself and when it is combined with other mutations (Tables 16 and 17, FIGS. 5–7). Its most notable effect is its very strong ability to depress the ratios of initial $iG_2$ formation rate to glucose formation rate, mainly by its depressing effect on the former (Table 17). Although the SS/311-314Loop and SS/Ser411→Ala GAs are more thermosensitive than SS and wild-type GAs, they are both more thermostable than 311-314Loop and Ser411→Ala GAs (Table 16), meaning that adding a mutation that singly confers thermostability to a GA already containing a thermosensitive mutation can make the latter more thermostable.

The Ser30→Pro mutation, having a Pro residue in a Type II β-turn in a highly conserved region of GA, was constructed to increase GA thermostability (Allen et al., 1998). It was combined previously with the SS and Gly137→Ala mutations (Allen et al., 1998) and then here with the 311-314Loop and Ser411→Ala mutations to form various doubly- and triply-mutated GAs. In general it has a neutral to slightly positive effect on GA specific activities (Table 16) and a slightly negative to slightly positive effect on glucose yields (Table 16, FIGS. 15, 18 and 19). At 35 and 45° C. it has a neutral effect on initial glucose formation rates and a positive effect on the ratios of initial $iG_2$ formation rate to glucose formation rate. At 55° C. it increases the former and decreases the latter (Table 16). It increases GA thermostabilities in singly- and multiply-mutated GAs (Table 17).

Even though the SS mutation gives a disulfide bond close to position 30, cumulative mutational effects in Ss/Ser30→Pro GA still occur. Furthermore, despite the suggestion of Balaji et al. (1989) that a disulfide bond should not be inserted in the protein primary structure within four amino acids of a Pro residue, SS/Ser30→Pro GA is more active, stable (Allen et al., 1998) and selective than wild-type GA. Li et al., (1997, 1998), Allen et al. (1998) and Liu et al. (1998) have suggested that the region between the C-terminus of α-helix 1 and the following extended loop between α-helices 1 and 2 is important for reversible thermoinactivation and selectivity. Further investigation might focus on single or deletion mutations in this region, as the loop is very thermo-labile and is exposed to solvent (P. M. Coutinho, personal communication, 1998).

Gly137, located in the middle of α-helix 4, which is a part of the inner ring of the αα-barrel around the active site, was mutated to Ala to increase GA thermostability, presumably by stiffening the helix (Chen et al., 1996). The Gly137→Ala mutation increases specific activity in GAs in which it is a part (Table 16), has a weakly positive to negligible effect on peak glucose yields (Table 16, FIGS. 15, 16, 18 and 19) and initial glucose formation rates (Table 17), sometimes increases and sometimes decreases initial rate ratios (Table 17), and increases thermostabilities (Table 16).

The 311-314Loop mutation was made to mimic the *Rhizopus oryzae* GA sequence, in the hope of decreasing $iG_2$ formation without affecting maltose hydrolysis (Liu et al., 1998). The mutation gave higher glucose yields (Table 16, FIGS. 17 and 18) and lower initial rate ratios (Table,17), but it also gave GAs with much lower specific activities, initial glucose formation rates and thermostabilities (Tables 16 and 17).

The Ser411→Ala mutation is one of a series constructed to increase the optimal pH of GA (Fang and Ford, 1998). It was meant to remove the hydrogen bond between atom OG of Ser411 and atom OE2 OFGlu400, which also hydrogen-bonds to both the catalytic water and to the hydroxyl group of the invariant Tyr48. The mutation strongly decreases specific activities and initial rates of glucose formation in the GAs where it occurs (Tables 16 and 17) due to the destruction of the hydrogen bond. It increases glucose yields (Table 16, FIGS. 17 and 19) and substantially decreases the initial rate ratio only in the GA where it is the only mutation and not in any multiply-mutated GAs in which it is found (Table 17). GAs with this mutation have strongly decreased thermostabilities (Table 16).

The Ser436→Pro mutation was made by Li et al. (1998) to reduce backbond bond rotation and therefore to decrease entropy during protein unfolding. It also fills a packing void and enhances hydrophobic interactions there. The mutation in fact confers added thermostability upon GAs that contain it but at the cost of decreased yields (Table 16, FIG. 16) and increased initial rate ratios (Table 17). The low specific activity found in Ser436→Pro GA is not carried over to other GAs containing the mutation (Table 16), and glucose formation rates are in general increased by it (Table 17).

Figure 14B:
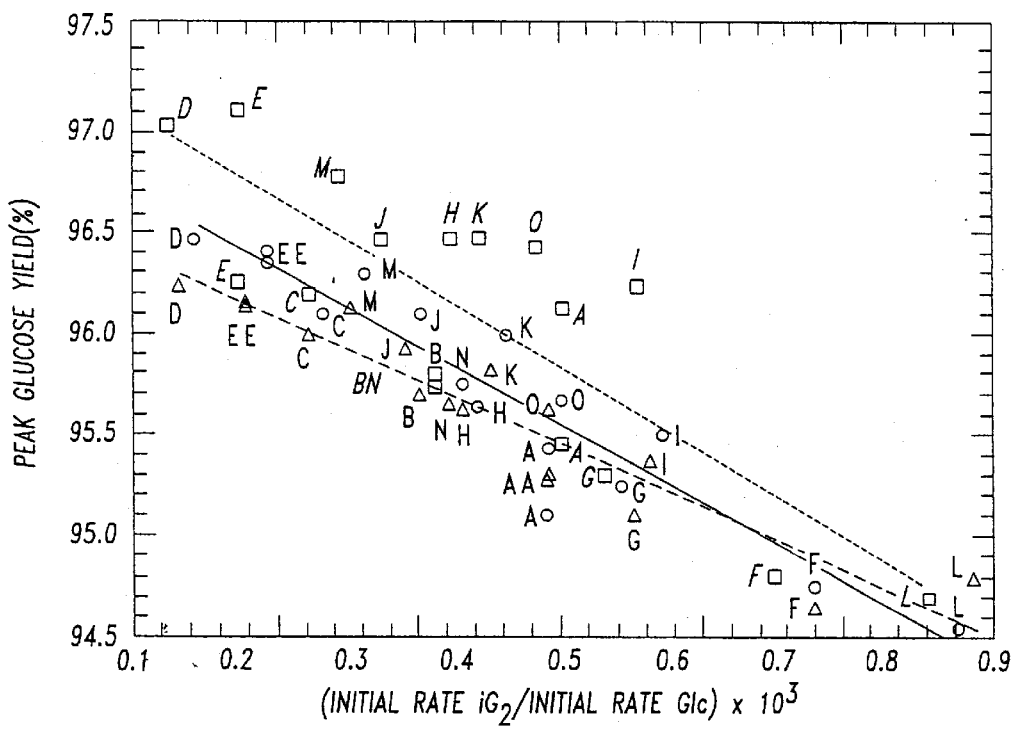
Figure 14C:
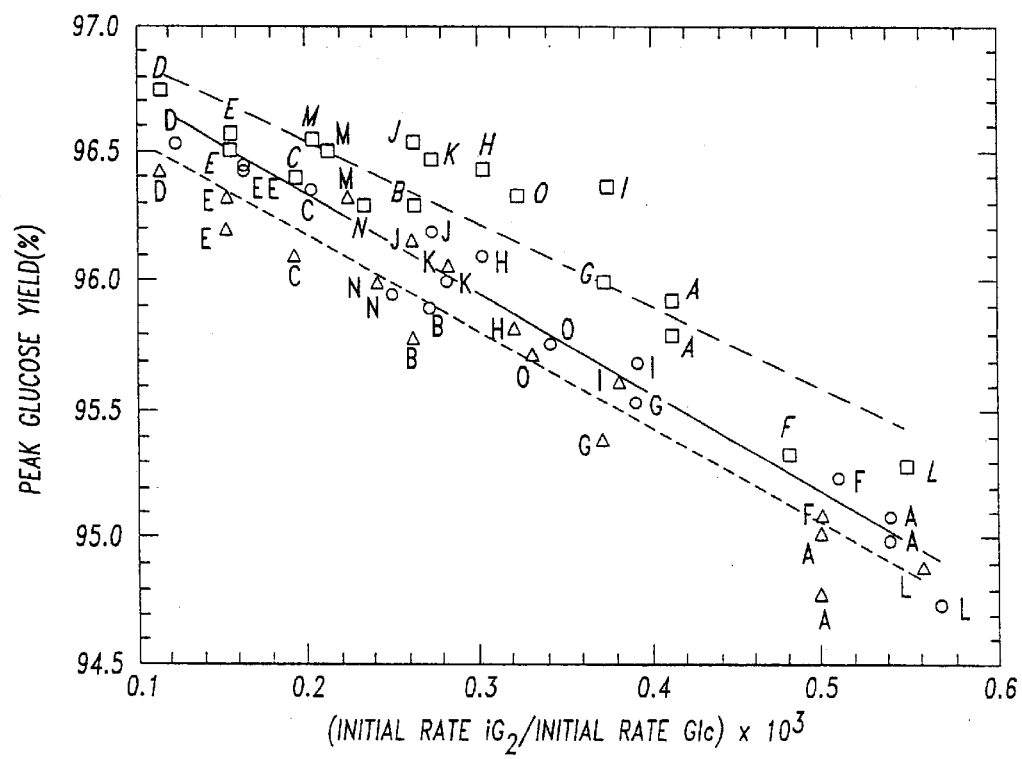

The hypothesis that decreasing the ability of GA to synthesize $iG_2$ would increase glucose yield was proved by Fang et al. (1998a,b) and Liu et al. (1998), generally with single mutations, and is confirmed here with multiple mutations. FIG. 14 shows the inverse relationship between peak glucose yields and initial rate ratios.

There is usually no significant difference among initial rates of glucose formation with substrates of different chain length at high substrate concentrations, even though catalytic efficiencies are higher for longer substrates than for shorter ones at low substrate concentrations (Liu et al., 1998).

Table 16 and FIG. 14 show that glucose yields tend to be slightly lower at higher reaction temperatures for wild-type GA and most mutated GAs, even though increasing reaction temperature results in progressively lower initial rate ratios (Table 17). The former result but not the latter one agrees with the catalytic efficiency ratios calculated by Coutinho (1996) from literature data on *A. awamori/A. niger* GA, in which ratios for $iG_2$ hydrolysis (and therefore $iG_2$ synthesis, assuming a stable equilibrium constant) to those of maltose hydrolysis increased with increasing temperature while those for maltooligosaccharide hydrolysis to those of maltrose hydrolysis decreased.

Of the sixteen GAs in Table 16 giving glucose yields clearly greater than that of wild-type GA, seven are more thermostable at 65° C. than wild-type GA and nine are less stable. Both the GAs with lower glucose yields are more stable than wild-type GA. This confirms the observations of Liu et al. (1998) that there is no general correlation between thermostability and selectivity. However, those GAs containing all mutations that presumably prevent unfolding at higher temperatures (SS, Ser30→Pro,Gly137→Ala, Ser436→Pro) uniformly have increased thermostability and tend to give increased glucose yield.

In summary, changes in selectivity to reduce $iG_2$ formation during glucose condensation and to increase glucose yield has been successfully attained in many of the multiply-mutated GAs studied here. It has also been demonstrated that specific activity, glucose yield, initial rate ratios and thermostability in multiply-mutated GAs can be predicted from the corresponding properties of the GAs containing the single mutations, suggesting that the principle of additive mutational effects in proteins is a powerful tool to improve glucose yield and thermostability. GA selectivity is affected by the reaction temperature, with glucose yields being higher at lower temperatures. There is no correlation between GA thermostability and selectivity.

Example 10

Additional Stability Mutuation Analysis

The yeast expression plasmid YepPM18 (Cole et al., 1988) and *S. cerevisiae* C468 (α leu2-3 leu 2-12 his 3-11 his 3-15 mal⁻) (Innis et al., 1985) were gifts from Cetus. All restriction enzymes were from Promega (Madison, Wis.). Acarbose was a gift from Miles Laboratories and Maltrin M100 DE 10 maltrodextran was a gift from the Grain Processing Corporation.

Site-directed Mutagenesis

Site-directed mutagenesis was performed according to the Muta-Gene phagemid in vitro mutagene is kit from Bio-Rad, which is based on the method of Kunkel et al. (1987). For the proline substitution mutants, a 1.7-kb XhoI-BamHI DNA fragment coding for the GA catalytic domain was cloned into a pBluescript II KS (+) vector from Stratagene. The following oligonucleotides were used as mutagenic primers: CAGAGTCCGCGCCCGGCACCCAAGCAC-CGTC (S30P), AAGTCCAGCGACACA GGTGTGACCTCCAACG-AC (D345P) and CGAGCG-GAAAGCTGCGGGCCATCAGA-CTTGTC (E408P). The underlined nucleotides in the primers indicate mismatches creating. the proline substitution mutations. For the S-S/S30P combined mutant, a 1.7-kb XhoI-BamHI DNA fragment coding for the wild-type GA catalytic domain was closed into a pBluescript II KS (+) vector from Stratagene. The following oligonucleotide was used as a mutagenic primer: CCGCGCCCGGCACCCAA CAACCG-TCCGCCCCGATGTTACACAGCATGGC, the underlined nucleotides represent DNA mismatches that create the S30P, A27C an N20C mutations, respectively. For the S30P/G137A mutant GA, the 1.7-kb Xho-BamHI DNA fragment coding for the previously constructed S30P GA catalytic domain was cloned into a pGEM-7Zf(+) vector from Promega. The following oligonucleotide was used as a mutagenic primer: ACTGCTATGATC GCTTTCGGGCAATGG. The underlined nucleotides indicate DNA mismatches that create the G137A amino acid substitution. The S-S/S30P/G137A combined mutant was constructed using the S-S/S30P oligonucleotide listed above and a DNA template derived from a pBluescript II KS (+) vector with a 1.7-kb XhoI-BamHI DNA fragment coding for the GA catalytic domain, which already contained mutations conferring the S30P and G137A amino acid substitutions. The presence of the individual mutations was confirmed by sequencing, and each mutated GA gene fragment was cloned into YepPM18 (Cole et al., 1988) and transformed into *S. cerevisiae*.

Enzyme Production and Purification

Wild-type, proline substitution mutants and S-S/S30P GAs were produced by growing yeast at 30° C. in 5.3 1 SD+His media [1.7 mg/ml yeast nitrogen base without amino acids or immonium sulfate (Difco), 5 mg/ml ammonium sulfate, 2% glucose, 0.1 mg/ml L-histidine] for 72 hours at pH 4.5 in a 5.0 L fermentor. After 48 hours, 100 g glucose and 22 g $(NH_4)_2SO_4$ in 300 ml $H_2O$ was added as a supplement (Chen et al., 1994a). S30P/G137A and S-S/S30P/G137A mutant GAs were produced by growing yeast in SD+His media at 30° C. for five days in a shaking incubator without pH control or the addition of supplement to the media. Following growth, the cultures were centrifuged to remove yeast cells, the supernatants were concentrated by ultrafiltration, diafiltered against 0.5 M naCl/0.1 M naOAc$_7$ pH 4.5, and GA purified by acarbose-Sepharose affinity chromatography (Chen et al., 1994b). GA was eluted with 1.7 M Tris-HCl, pH 7.6, dialyzed against $H_2O$, further concentrated by ultrafiltration and diafiltered against 0.05 M naOAc buffer, pH 4.5. The protein concentration was determined according to the Pierce bicinchoninic acid protein assay (Smith et al., 1985) using bovine serum albumin as a standard.

Enzyme Assays

Enzyme kinetic assays were done as described by Li et al. (1997) using maltose as a substrate at pH 4.5 and 35° C. Maltose concentrations used ranged from 0.2 to 4 $K_M$, in 0.005 M NaOAc buffer. Kinetic parameters were analyzed by the program ENZFITTER (Elsevier-Biosoft).

Enzyme specific activities were determined at 50° C. using 4% maltose in 0.05 M NaOAc buffer, pH 4.5, as substrate. The international unit (IU) of enzyme activity was defined as the amount of enzyme required to produce 1 $\mu$mol/min glucose at assay conditions. Following mixing of enzyme with substrate, six 100-$\mu$l samples were removed at seven minute intervals over 42 minutes, the reaction was stopped with 40 $\mu$l of 4.0 M Tris-HCl, pH 7.0, and the glucose concentration was determined by a glucose oxidase/o-dianisidine assay (Banks et al., 1971).

Irreversible Thermoinactivation

Duplicate aliquots of 40 $\mu$g/ml purified wild-type and mutant enzymes were subjected to inactivation at six or more temperatures between 65 and 80° C. (except E408P which was inactivated at five temperatures between 58.5 and 68.5° C.) at intervals of 2.5° C. Samples were removed at six different times, immediately placed on ice and stored at 4° C. for 24 hours to eliminate the possibility that the inactivation observed was reversible. The residual activity of the inactivated samples, along with a corresponding sample which had not been subjected to thermoinactivation, was determined as described for enzyme specific activities, but at 35° C.

Saccharification Analysis

Saccharifications were performed in duplicate using stirring heating blocks and tightly sealed vials to prevent evaporation. Wild-type and mutant GAs (8° $\mu$g/ml) were assayed using 28% (w/v) DE 10 maltodextrin in 0.05 M naOAc, pH 4.5, as substrate. At various times, a sample was removed, diluted appropriately in 0.05 M NaOAc, pH 4.5, and the reaction was stopped by adding 100 $\mu$l diluted sample to 40 $\mu$l 4.0 M Tris-HCl, pH 7.0. The glucose concentration was determined by a glucose oxidase/o-dianisidine assay (Banks et al., 1971).

Results

Irreversible Thermostability

Wild-type and mutant GAs were subjected to thermo-inactivation at pH 4.5 between 65 and 80° C. Semilogarithmic plotting of residual activity versus inactivation time was used to determine inactivation rate coefficients ($k_d$) FIG. 20 shows the effect of temperature on $k_d$ for wild-type, S30P, D345P and E408P GAs. As can be seen, the S30P mutation increased GA stability, whereas the D345P did not significantly alter and the E408P greatly decreased GA stability. The combined mutants S30P/G137A, S-S/S30P and S-S/30P/G137A were analyzed in a similar manner, and the results are shown in FIG. 21. Additionally, the temperature at which the enzymes were 50% inactivated after 10 min ($T_m$) was calculated by extrapolation from the thermoinactivation plots, and transition-state theory was used to calculate activation energies for thermal inactivation ($\Delta G^{\ddagger}$) at 65° C. Table I shows the changes in $\Delta G^{\ddagger}$ ($\Delta\Delta G^{\ddagger}$) and $T_m$ ($\Delta T_m$) for the individual and combined mutant GAs relative to wild-type. These data clearly demonstrate that the S30P mutation stabilizes the enzyme, and that combining S30P with S-S and G137A mutations can cumulatively stabilize GA.

Enzyme Activities

Table 19 shows kinetic analysis of the mutants and wild-type at 35° C. Although $K_{cat}/K_M$ values were similar for the mutants and wild-type, $K_{cat}$ values. for the mutants were almost 10% higher than that of the wild-type. Table 20 shows specific activities of the wild-type and mutant GAs at 50° C. and pH 4.5 using maltose as substrate. None of the mutant GAs demonstrated reduced enzyme activity; however, the S30:/G137A and S-S/S30P/G137A mutants were somewhat more active than wild-type at 50° C. To determine if the apparent increased activity was due to differential survival of active enzyme at the assay temperature, the activities of these mutant enzymes were assayed at various temperatures between 35 and 68° C. The S30P/G137A and S-S/S30P/G137A mutant GAs were 10–20% more active than wild-type at all temperatures examined. A possible explanation for this observation will be discussed below.

Saccharification Analysis

FIG. 22A and B show the results of saccharification analysis at 55 and 65° C. for wild-type. S30P/G137A and S-S/S30P/G137A GAs using the industrial DE10 maltodextrin substrate Maltrin M10 (28% w/v) from the Grain Processing Corporation. Complete conversion of 28% w/v DE 10 maltodextrin to glucose would result in a 1.71 M glucose syrup. Industrial saccharifications typically result in 96% maximum conversion to glucose (O'Rourke et al., 1996). However, previous saccharification analyses in our laboratory have demonstrated that recombinant wild-type GA produced by yeast typically results in approximately 90% theoretical maximum glucose yield at 55° C. (Fang et al., 1988a,b; Liu et al., 1998). The difference is apparently due to the lack of secondary enzymes ($\alpha$-amylase and pullulanase) present in the industrial reactions (O'Rourke et al., 1996). At 55° C. no significant difference in glucose production was observed between the wild-type and mutant enzymes (all of which resulted in approximately 90% conversion of DE 10 maltodextrin to glucose), indicating that thermo-inactivation of wild-type was not rate-determining and that specific activity differences between wild-type and the mutants did not affect the final glucose yield over the time course of the reaction. At 65° C., however, the mutant GAs produced 8–10% more glucose than wild-type GA, although none of the enzymes tested produced as much glucose at 55° C. probably due to thermoinactivation of the enzymes at the elevated reaction temperature.

Discussion

Sites of Mutation

FIG. 23 shows the sites of mutation in the catalytic domain of A.awamori var.X100 GA whose structure is known (Aleshin et al., 1992). Based on this structure, threesites were chosen for proline substitution, which met the following criteria: (i) Ramachandran ($\phi,\Psi$) angles (Ramachandran et al., 1963) were within allowed values for proline. For this work, the $\phi$ and $\Psi$ angles at the substituted site were restrained to the broad range $\phi=-90$ to $-40°,\Psi=120$ to $180°$ or $\phi=-90$ to $-40°,\Psi=50$ to $10°$; (ii) Residues were highly solvent-exposed, since mutation of residues in the core of the enzyme were thought to be more likely to decrease the enzyme's catalytic efficiency; (iii) Residues did not participate in hydrogen bonding with other amino acids. Additionally, based on sequence alignments with GAs from other organisms (Coutinho and Reilly, 1994), only residues that met the above structural criteria and were not well conserved were selected for mutation. Ser30 could be aligned with proline in GAs from *Humicola grisea* var. *thermoidea* and *Hormoconis resinae* GamP (Coutinho and Reilly, 1994), which made it particularly attractive for proline substitution. The criteria used to select the sites of mutation for the S-S and G137A mutations have been discussed in detail by Chen et al. (1996) (Q137A), and Li (1996) S-S) and will not be repeated. Briefly, the mutations Asn20→Cys and Ala27→Cys form a disulfide bond between the C-terminus of α-helix 1 and an extended loop between α-helices 1 and 2 (Li, 1996), and G137A was designed to stabilize the enzyme by reducing its conformational entropy of unfolding and is the most stabilizing in a series of Gly→Ala mutations (Chen et al., 1996).

It is of particular importance to note the positions of the S30P and the disulfide bond-forming mutations The disulfide bond is formed between positions 20 and 27, relatively close to position 30. The fact that both the disulfide bond-forming mutations and the S30P stabilize GA suggests that this region of the enzyme is critical for irreversible thermoinactivation and may represent a region of local unfolding important for thermoinactivation. Additionally, previous investigators have suggested that a disulfide bond should not be engineered within four amino acids of a proline in the primary sequence (Balaji et al., 1989). This work demonstrates that this rule is not absolute since thiol analysis showed that the disulfide bond was formed in the S-S/S30P and S-S/S30P/G137A combined mutants and thermoinactivation studies showed the stabilizing effects of the mutations were cumulative.

Enzyme Activity

None of the proline substitution mutations decreased enzyme activity as shown by kinetic analysis at 35° C. and by specific activity measurements at 50° C. This suggests that these mutations did not significantly alter the enzyme's structure around the active site or alter its interaction with substrate. Additionally, neither S-S nor G137A mutant GAs had enzyme activity significantly different from wild-type GA at 50° C. (Li, 1996; Chen et al., 1996). The S30P/G137A and S-S/S30P/G137A combined mutants, however, had slightly increased activity compared with wild-type GA at all temperatures tested between 35 and 68° C. A possible explanation for this may be the existence of active and inactive conformations due to local unfolding and refolding of the molecule at the assay temperature. Introduction of stabilizing mutations may result in a greater population of molecules in an active conformation, thus resulting in higher specific activity for the mutant enzymes.

Stability of the Proline Substitution Mutants

The proline substitution mutants had different thermostabilities when measured by their resistance to irreversible thermoinactivation. When compared with wild-type GA, E408P decreased, D345P did not significantly alter and S30P increased GA stability (FIG. 20 and Table 18).

E408P destabilized Ga. As was first suggested by Schimmel and Flory (1968), and has been expanded by others (MacArthur and Thorton, 1991; Hurley et al., 1992), proline not only restricts the $\phi$; $\Psi$ values for the site at which it exists, but also the $\phi,\Psi$ values of the preceding residue. These reports suggest that the ($\phi,\Psi$) values for the residue preceding proline should be restricted to approximately $\phi=-180$ to $-55°$ and $\Psi=-30$ to $-70°$ for all residues in Xaa-Pro except for Xaa-Gly, for which the preceding still applies, but is extended to include $+=45$ to $180°$. In the published *A.awamori var.* X100 catalytic domain structure (Aleshin et al., 1992), Asp408 ($\phi-65°$, $\Psi=146°$), which aligns with Glu408 in *A.awamori* GA, has $\phi,\Psi$ values within ranges acceptable for proline. However, the preceding residue Gly407 ($\phi=80°,\Psi=-5°$) has $\phi,\Psi$ outside acceptable ranges for positions preceding proline. Therefore, it was not surprising that the E408P mutation destabilized GA. Additionally, X-ray crystallography suggests that position 408 lies within a β-strand in the closely related *A.awamori* var. X100 GA, a site not well suited for proline substitution.

Asp345 ($\phi=-65°$, $\Psi=-26°$) and the preceding Thr344 ($\phi=-116°$, $\Psi=178°$) have $\phi,\Psi$ angle values well within allowed values for proline substitution at position 345. However, the D345P mutant GA did not demonstrate stability significantly different from wild-type GA. This is particularly interesting since position 345 lies at the N-terminus of an α-helix (Aleshin et al., 1992), a position previously shown to be particularly favorable for proline substitution (Watanabe et al., 1994). A possible explanation for this observation is that Asp345 is at the N-terminus of α-helix 11 in the *A.awamori* var. X100 GA structure (Aleshin et al., 1992). Replacing Asp345 with Pro could disrupt the α-helix dipole. Therefore, any entropic stabilization brought about by the proline substitution might be offset by the disruption in the α-helix dipole. An alternative explanation for this observation is that α-helix 11 is not part of the core 12-helix α/α barrel structure, and therefore stabilization of this helix may not be reflected in our functional stability assay. Interestingly, LI (1996) showed that another mutation in this region, Lys352→Arg, which was predicted to increase GA stability but failed to do so in our functional assay, did increase one thermal unfolding transition by 1.5° C. when measured by differential scanning calorimetry. This suggests that the region including α-helix 11 may represent a subdomain that unfolds independently of the rest of the catalytic domain. In other words, it may be possible that slight stabilization or destabilization of α-helix 11 does not result in an enzyme with significantly altered functional stability since this helix is not part of the core α/α barrel.

Ser30 ($\phi=-49°$, $\Psi=130°$) is preceded by Val29 ($\phi=127°$, $\Psi=46°$) both of which have acceptable $\phi,\Psi$ angle values except Val29 $\Psi=46°$ which is slightly smaller than ideal for proline substitution at position 30. Upon characterization, the S30P substitution increased GA thermostability, Position 30 lies on an extended loop between a-helices 1 and 2 in the *A.awamori* var. X100 GA structure (Aleshin et al., 1922), and can be aligned with proline in other GAs as discussed above. When this loop region is examined more closely, position 30 is at the second position of a type II β-turn using the definition of Wilmot and Thornton (1998). This is in agreement with the observations of Watanabe et al., (1994), who have suggested that the second position of β-turns is particularly favorable for proline substitution. These investigators have reported increases in $T_m$ of 0.8–1.4° C. per proline residue for substitutions made at the second position of β-turns in *Bacillus cereus* ATCC 7064 oligo-1,6-glucosidase.

Cumulative Stabilization

Previous work in our laboratory has shown that combining two stabilizing mutations does not necessarily stabilize GA (Chen et al., 196). The present study shows that the three mutations chosen here can be combined to cumulatively stabilize the enzyme even though two of the mutations (S-S and S30) are very close together in the protein. Thus, cumulative thermostabilization must be assessed on a case by case basis.

S30P combined with G137A showed more than additive stabilization at low temperatures (65–70° C.) but less than additive stabilization at high temperatures (77.5–80° C.) (FIG. 21A). At 80° C. the inactivation rate for the S30P/G137A combined mutant was nearly identical to that of the S30P individual mutant protein. This indicates that both regions are very important for low temperature thermoinactivation, but at high temperatures inactivation became governed by other processes.

It was somewhat surprising that combining the S30P with the disulfide bond-forming mutations resulted in cumulative stabilization. This is not only because the engineered disulfide bond is so close to the engineered proline as discussed above, but also because both are targeting the same region of the protein (i.e. the extended loop between α-helices 1 and 2). If either the disulfide bond or S30P stabilized this region maximally, further stabilization at this site would not result in roughly additive stabilization at all temperatures examined between 65 and 80° C. This raises the possibility that further. stabilization may result from the addition.of more stabilizing mutations in this region.

The S-S/S30P/G137A combined mutant was no more stable than S30P/G137A GA at low temperatures (65–70° C.), but it was slightly more stable at higher temperatures (75–80° C.) (FIG. 2C). Interestingly, the S-S/S30P GA was also more stable than S30P/G137A GA at high temperatures. Therefore, it appears that the introduced disulfide bond is particularly effective at stabilizing GA at high temperatures. The cause for this observation remains unclear. However, given the position of the bond, it may serve to anchor the extended loop to the first α-helix, thereby preventing it from unfolding even at high temperatures.

INDUSTRIAL APPLICATION

Carbohydrates are known to stabilize proteins (Shein, 1990; Butler and Falke, 1996), including GA (Taylor et al., 1978; Sinitsyn et al., 1978; Przybyt and Sugier, 1988). To determine whether the most stabilizing mutations, S30P/G137A and S-S/S30P/G137A, would enhance GA performance under conditions more closely resembling those which the enzyme would encounter industrially, the enzymes were subjected to high temperature saccharifications (FIG. 3). The mutant enzymes outperformed wild-type GA at 65° C., but not at 55° C., due to their increased stability.

CONCLUSIONS

It has been demonstrated that significant and cumulative stablization of *A.awamori* GA by proline substitution mutagenesis and by combining individual stabilizing mutations. It is significant that the most stabilizing mutations in GA identified to date all decrease the enzyme's conformation entropy of unfolding. Additional stabilization may be achieved by introducing other mutations that decrease unfolding entropy. In addition, it has been shown that a disulfide bond can be successfully engineered within four amino acids of proline. This may have significance for those wishing to engineer disulfide bonds in other enzymes.

The most important conclusion of this work is the significant stabilization of GA without activity loss, as seen both in irreversible thermoinactivation assays and during the saccharification of an oligosaccharide substrate. Based on irreversible thermoinativation analysis, it is estimated that the S30P/G137A and S-S/S30P/G137A mutant Gas could be used industrially at temperatures 3–4° C. higher than wild-type GA. This can greatly increase the rate of saccharification reactions (or decrease amounts of enzyme required to give the same reaction rate as at 60° C.), decrease microbial contamination of reaction vessels and decrease the viscosity of reaction syrups. Conversely, the mutant GA can be used at the same temperature as wild-type but for much longer reaction times,-which significantly decreases the amount of enzyme required to carry out starch saccharification.

Throughout this application, various publications are referenced by author and year and patents listed by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Changes in $\Delta G^{\ddagger}$ and Tm for the mutant GAs relative to wild-type.

| GA form | $\Delta\Delta G^{\ddagger}$ (kJ/mol.) | $\Delta$Tm (° C.) |
|---|---|---|
| Ser30→Pro | 1.6 | 1.7 |
| Asp345→Pro | 0.5 | 0.4 |
| Glu408→Pro | −7.2 | −6.7 |

TABLE 2

Summary of DTNB-titratable sulfhydryl groups in wild-type and mutant GA with or without DTT reducing

| | [SH]/molecule | | |
|---|---|---|---|
| Enzymes | DTT+ | DTT− | No. of disulfide bonds* |
| WT | 8.6 | 0.9 | 4 |
| A27C/N20C | 10.9 | 0.9 | 5 |
| A471C/T72C | 10.4 | 1.3 | 5 |

*No. of disulfide bonds = ([SH]/molecule (DTT+) − [SH]/molecule (DTT−))/2

TABLE 3

Catalytic properties of wild type and mutant GAs.

| GA form | Specific Activity (IU/mg GA) | $K_m$ (mM)$_m$ | $k_{cat}$ (s$^{-1}$)$_{cat}$ | $k_{cat}/K_m$ (s$^{-1}$ mM$^{-1}$) |
|---|---|---|---|---|
| WT[a] | 20.6 ± 0.2[b] | 0.72 ± 0.03 | 8.67 ± 0.17 | 12.0 |
| A27C | 14.9 ± 1.1 | 0.86 ± 0.11 | 8.02 ± 0.45 | 9.3 |
| N20C | 8.1 ± 0.5 | 0.70 ± 0.05 | 3.97 ± 0.12 | 5.7 |
| A27C/N20C | 18.3 ± 0.7 | 0.90 ± 0.08 | 9.61 ± 0.40 | 10.7 |
| A471C/T72C | 22.7 ± 1.5 | 0.87 ± 0.07 | 10.17 ± 0.40 | 11.6 |
| A27C/N20C/S436 | 22.5 ± 1.8 | N/D[c] | N/D | N/D |
| A27C/N20C/G137A | 24.2 ± 0.8 | N/D | N/D | N/D |
| G137A/S436P | 25.0 ± 0.9 | N/D | N/D | N/D |

[a]Produced in shaking flasks
[b]standard error
[c]not determined

TABLE 4

Activation parameters for irreversible thermoinactivation of wild-type (WT) and mutant GAs at pH 4.5.

| GA form | $\Delta H^{\ddagger}$ (kJ/mol) | $\Delta S^{\ddagger}$ (J/mol · K) | $\Delta G^{\ddagger}$ (65° C.) (kJ/mol) | $\Delta G^{\ddagger}$ (75° C.) (kJ/mol) |
|---|---|---|---|---|
| WT[a] | 366 ± 1[b] | 769 ± 4 | 105.7 | 98.0 |
| A27C | 370 ± 15 | 780 ± 44 | 106.3 | 98.5 |
| N20C | 324 ± 11 | 654 ± 33 | 102.7 | 96.2 |
| A27C/N20C | 342 ± 16 | 694 ± 46 | 107.2 | 100.2 |
| A471C/T72C | 365 ± 9 | 768 ± 26 | 106.0 | 98.3 |
| A27C/N20C/S436P | 352 ± 6 | 724 ± 18 | 107.9 | 100.7 |
| A27C/N20C/G137A | 362 ± 1 | 751 ± 2 | 108.4 | 100.9 |
| G137A/S436P | 362 ± 20 | 752 ± 57 | 107.7 | 100.2 |
| S436P[c] | 351 ± 8 | 723 ± 24 | 106.2 | 99.0 |
| G137A[d] | 330 ± 6 | 661 ± 17 | 106.5 | 99.9 |

[a]produced by shaking flask
[b]standard error
[c]Li et al., 1996
[d]Chen et al., 1996

TABLE 5

Specific activities of wild-type and mutant GAs

| GA form | Specific activity[a] (IU/mg) |
|---|---|
| Wild-type | 21.1 ± 0.1 |
| S30P/Gly137A | 24.0 ± 1.2 |
| S-S/S30P | 21.2 ± 0.5 |
| S-S/S30P/G137A | 24.5 ± 0.2 |

[a]Standard deviation resulting from three or more assays

TABLE 6

Thiol analysis of wild-type and mutant GAs

| GA form | [Protein] ($\mu$M) | [SH] ($\mu$M)[a] | [SH]/[Protein][a] |
|---|---|---|---|
| Wild-type | 10 | 8 | 0.8 |
| S-S/S30P | 10 | 11 | 1.1 |
| S-S/S30P/G137A | 10 | 13 | 1.3 |

[a]Average of duplicate analysis

TABLE 7

Changes in free energies for thermal inactivation ($\Delta\Delta G^{\ddagger}$) and temperatures at which the enzyme is 50% inactivated after 10 minutes ($\Delta$Tm) relative to wild-type GA

| GA form | $\Delta\Delta G^{\ddagger a}$ (kJ/mol) | $\Delta$Tm (° C.) |
|---|---|---|
| S30P[b] | 1.6 | 1.7 |
| G137A[c] | 0.8 | 1.2 |
| S-S[d] | 1.2 | 1.4 |
| S30P/G137A | 4.5 | 3.5 |
| S-S/S30P | 3.5 | 3.2 |
| S-S/S30P/G137A | 4.4 | 3.9 |

[a]Calculated at 65° C.
[b]From Allen et. al.[8]
[c]From Chen et. al.[6]
[d]From Li et. al.[7]

TABLE 8

Kinetic parameters of wild-type and mutant GAs for hydrolysis of maltooligosaccharides DP 2-7 ($G_2$–$G_7$) at 45° C. in 0.05 M acetate pH 4.4

| Glycoamylase | $G_2$ | $G_3$ | $G_4$ | $G_5$ | $G_6$ | $G_7$ |
|---|---|---|---|---|---|---|
| Wild-type | | | | | | |
| $\kappa_{cat}(s^{-1})$ | 18.6 ± 0.4[a] | 50.8 ± 0.6 | 67.5 ± 1.9 | 61.5 ± 0.33 | 65.9 ± 1.2 | 81.5 ± 1.8 |
| $\kappa_M$(mM) | 1.09 ± 0.08 | 0.353 ± 0.013 | 0.239 ± 0.017 | 0.094 ± 0.002 | 0.098 ± 0.007 | 0.136 ± 0.009 |
| $\kappa_{cat}/\kappa_M(s^{-1}mM^{-1})$ | 17.1 ± 0.9 | 144 ± 4 | 282 ± 13 | 653 ± 10 | 671 ± 36 | 599 ± 27 |
| Lys108Arg | | | | | | |
| $\kappa_{cat}(s^{-1})$ | 17.3 ± 0.5 | 32.6 ± 0.9 | 46.6 ± 1.6 | 51.7 ± 1.4 | 55.2 ± 1.4 | 86.2 ± 3.1 |
| $\kappa_M$(mM) | 1.52 ± 0.11 | 0.570 ± 0.038 | 0.383 ± 0.029 | 0.307 ± 0.019 | 0.276 ± 0.016 | 0.481 ± 0.031 |
| $\kappa_{cat}/\kappa_M(s^{-1}mM^{-1})$ | 11.4 ± 0.6 | 57.2 ± 2.5 | 122 ± 5 | 168 ± 6 | 200 ± 8 | 179 ± 6 |
| $\Delta(\Delta G)$[b] (kJ mol$^{-1}$) | 0.92 | 2.10 | 1.91 | 3.08 | 2.75 | 2.74 |
| Tyr312Trp | | | | | | |
| $\kappa_{cat}(s^{-1})$ | 17.2 ± 0.3 | 36.8 ± 0.9 | 50.7 ± 0.9 | 50.7 ± 0.8 | 56.0 ± 0.8 | 63.3 ± 0.6 |
| $\kappa_M$(mM) | 0.940 ± 0.059 | 0.343 ± 0.028 | 0.193 ± 0.010 | 0.100 ± 0.006 | 0.108 ± 0.005 | 0.103 ± 0.003 |
| $\kappa_{cat}/\kappa_M(s^{-1}mM^{-1})$ | 18.3 ± 0.90 | 107 ± 6 | 262 ± 9 | 508 ± 22 | 519 ± 20 | 617 ± 1 |
| $\Delta(\Delta G)$ (kJ mol$^{-1}$) | −0.16 | 0.67 | 0.17 | 0.57 | 0.58 | −0.07 |
| 300Loop | | | | | | |
| $\kappa_{cat}(s^{-1})$ | 14.7 ± 0.3 | 25.9 ± 0.6 | 34.1 ± 0.8 | 43.0 ± 0.6 | 41.4 ± 0.8 | 41.9 ± 0.7 |
| $\kappa_M$(mM) | 0.738 ± 0.055 | 0.234 ± 0.019 | 0.114 ± 0.008 | 0.072 ± 0.004 | 0.064 ± 0.005 | 0.083 ± 0.005 |
| $\kappa_{cat}/\kappa_M(s^{-1}mM^{-1})$ | 20.0 ± 1.2 | 111 ± 7 | 300 ± 17 | 598 ± 28 | 642 ± 47 | 506 ± 25 |
| $\Delta(\Delta G)$ (kJ mol$^{-1}$) | −0.35 | 0.60 | −0.14 | 0.20 | 0.10 | 0.38 |
| Ser30Pro/Gly137Ala | | | | | | |
| $\kappa_{cat}(s^{-1})$ | 25.0 ± 1.1 | 50.2 ± 3.0 | 77.9 ± 2.2 | 77.7 ± 1.6 | 77.0 ± 2.2 | 80.3 ± 2.2 |
| $\kappa_M$(mM) | 1.62 ± 0.11 | 0.596 ± 0.010 | 0.261 ± 0.020 | 0.175 ± 0.011 | 0.204 ± 0.017 | 0.151 ± 0.013 |
| $\kappa_{cat}/\kappa_M(s^{-1}mM^{-1})$ | 15.5 ± 1.2 | 84.2 ± 3.1 | 299 ± 16 | 444 ± 21 | 377 ± 23 | 533 ± 37 |
| $\Delta(\Delta G)$ (kJ mol$^{-1}$) | 0.27 | 1.42 | −0.15 | 1.02 | 1.52 | 0.31 |
| SS/Ser30Pro/Gly137Ala | | | | | | |
| $\kappa_{cat}(s^{-1})$ | 23.0 ± 0.9 | 42.1 ± 1.0 | 72.0 ± 2.1 | 72.2 ± 1.0 | 79.5 ± 1.7 | 81.5 ± 1.4 |
| $\kappa_M$(mM) | 1.66 ± 0.07 | 0.470 ± 0.032 | 0.236 ± 0.019 | 0.172 ± 0.007 | 0.157 ± 0.011 | 0.198 ± 0.010 |
| $\kappa_{cat}/\kappa_M(s^{-1}mM^{-1})$ | 13.9 ± 0.9 | 89.6 ± 4.2 | 305 ± 17 | 420 ± 13 | 505 ± 26 | 410 ± 15 |
| $\Delta(\Delta G)$ (kJ mol$^{-1}$) | 0.55 | 1.26 | −0.21 | 1.16 | 0.75 | 1.00 |
| SS | | | | | | |
| $\kappa_{cat}(s^{-1})$ | 20.7 ± 0.6 | 40.8 ± 0.9 | 72.1 ± 1.3 | 76.5 ± 0.8 | 76.4 ± 2.1 | 71.8 ± 0.6 |
| $\kappa_M$(mM) | 1.16 ± 0.10 | 0.394 ± 0.025 | 0.217 ± 0.011 | 0.132 ± 0.005 | 0.184 ± 0.015 | 0.114 ± 0.003 |
| $\kappa_{cat}/\kappa_M(s^{-1}mM^{-1})$ | 17.8 ± 1.1 | 104 ± 5 | 331 ± 12 | 579 ± 16 | 414 ± 26 | 632 ± 15 |
| $\Delta(\Delta G)$ (kJ mol$^{-1}$) | −0.10 | 0.88 | −0.42 | 0.32 | 1.28 | −0.14 |

[a]Standard error
[b]Change of transition-state energy $\Delta(\Delta G) = -RT\ln[(\kappa_{cat}/\kappa_M)_{mut}/(\kappa_{cat}/\kappa_M)_{wt}]$

TABLE 9

Initial rates of glucose and isomaltose productions in the hydrolysis of 30% (w/v) maltodextrin M100 and 30% (w/v) glucose condensations, respectively, and their relative ratios for wild-type and mutant glucoamylases at 35° C., 45° C., and 55° C.

| | Initial rates | | Ratios | |
|---|---|---|---|---|
| Enzymes | Glucose[a] (G1) ($\mu$g/mL · h) × $10^{-3}$ | Isomaltose[b] (iG$_2$) ($\mu$g/mL · h) × $10^3$ | Ratios (iG$_2$/G1) × $10^6$ | Relative ratios |
| 35° C. | | | | |
| Wild-type | 21.5 ± 0.6[c] | 289 ± 5 | 13.5 | 1.00 |
| Lys108Arg | 22.0 ± 0.4 | 969 ± 12 | 44.1 | 3.27 |
| Tyr312Trp | 17.9 ± 0.5 | 294 ± 4 | 16.4 | 1.21 |
| 311–314Loop | 13.8 ± 0.4 | 128 ± 3 | 9.3 | 0.69 |
| Ser30Pro/Gly137Ala | 27.7 ± 0.4 | 298 ± 6 | 10.8 | 0.80 |
| S-S/Ser30Pro/Gly137Ala | 30.1 ± 0.5 | 245 ± 6 | 8.2 | 0.60 |
| S-S | 31.8 ± 0.6 | 135 ± 3 | 4.2 | 0.31 |
| Ser436Pro | 29.9 ± 0.6 | 903 ± 12 | 30.2 | 2.23 |
| S-S/Ser436Pro | 31.7 ± 0.5 | 824 ± 12 | 26.0 | 1.92 |
| S-S/Gly137Ala | 35.2 ± 0.6 | 982 ± 15 | 27.9 | 2.07 |
| Gly137Ala/Ser436Pro | 36.6 ± 0.7 | 776 ± 10 | 21.2 | 1.57 |
| 45° C. | | | | |
| Wild-type | 66.2 ± 2.2 | 3880 ± 60 | 58.7 | 1.00 |
| Lys108Arg | 50.2 ± 2.0 | 6420 ± 110 | 128 | 2.18 |
| Tyr312Trp | 52.6 ± 2.1 | 3360 ± 60 | 63.9 | 1.09 |

TABLE 9-continued

Initial rates of glucose and isomaltose productions in the hydrolysis of 30% (w/v) maltodextrin M100 and 30% (w/v) glucose condensations, respectively, and their relative ratios for wild-type and mutant glucoamylases at 35° C., 45° C., and 55° C.

|  | Initial rates | | Ratios | |
|---|---|---|---|---|
| Enzymes | Glucose[a] (G1) ($\mu$g/mL · h) × $10^{-3}$ | Isomaltose[b] (iG$_2$) ($\mu$g/mL · h) × $10^3$ | Ratios (iG$_2$/G1) × $10^6$ | Relative ratios |
| 311–314Loop | 40.4 ± 1.8 | 1430 ± 40 | 35.3 | 0.60 |
| Ser30Pro/ Gly137Ala | 76.3 ± 2.7 | 3690 ± 70 | 48.4 | 0.83 |
| S-S/Ser30Pro/ Gly137Ala | 84.3 ± 3.0 | 3520 ± 60 | 41.7 | 0.71 |
| S-S | 86.3 ± 3.3 | 963 ± 28 | 11.2 | 0.19 |
| 55° C. | | | | |
| Wild-type | 156 ± 3 | 4890 ± 80 | 31.3 | 1.00 |
| Lys108Arg | 101 ± 1 | 8200 ± 120 | 81.0 | 2.59 |
| Tyr312Trp | 110 ± 2 | 4440 ± 70 | 40.5 | 1.29 |
| 311–314Loop | 128 ± 2 | 1890 ± 50 | 14.8 | 0.47 |
| Ser30Pro/ Gly137Ala | 157 ± 3 | 7200 ± 110 | 45.8 | 1.47 |
| S-S/Ser30Pro/ Gly137Ala | 167 ± 3 | 5690 ± 100 | 34.1 | 1.09 |
| S-S | 164 ± 3 | 1230 ± 40 | 7.5 | 0.24 |
| Ser436Pro | 218 ± 3 | 4710 ± 80 | 21.6 | 0.69 |
| S-S/Ser436Pro | ND[d] | 5130 ± 100 | ND | ND |
| SS/Gly137Ala | 225 ± 3 | 5720 ± 100 | 25.4 | 0.61 |
| Gly137Ala/ Ser436Pro | 208 ± 3 | ND | ND | ND |

[a]Samples were taken from 30% (w/v) M100 hydrolysis reactions in 0.05 M NaOAc buffer, pH 4.4; glucose concentrations were determined by glucose oxidase method.
[b]Samples were taken from 30% (w/v) glucose condensation reactions in 0.05 M NaOAc buffer, pH 4.4; isomaltose concentrations were determined by HPTLC.
[c]Standard error
[d]Not determined

TABLE 10

Kinetic parameters of wild-type and mutant glucoamylase for hydrolysis of isomaltose and maltooligodextrins of DP 2-7

| Enzyme | Substrate | | | | | | | $\kappa_{cat}/K_m$ (G2) $\kappa_{cat}/K_m$ (iG2) |
|---|---|---|---|---|---|---|---|---|
|  | Isomaltose (iG2) | Maltose (G2) | Maltotriose (G3) | Maltotetraose (G4) | Maltopentoase (G5) | Maltohexaose (G6) | Maltoheptaose (G7) | |
| Wild-type | | | | | | | | 656 |
| $\kappa_{cat}(S^{-1})$ | 0.72 ± 0.01[b] | 20.4 ± 0.2 | 48.2 ± 0.7 | 64.5 ± 2.9 | 71.8 ± 1.9 | 73.7 ± 2.1 | 72.3 ± 0.9 | |
| $\kappa_m$(mM) | 23.5 ± 0.6 | 1.01 ± 0.03 | 0.25 ± 0.014 | 0.111 ± 0.017 | 0.110 ± 0.010 | 0.107 ± 0.010 | 0.083 ± 0.004 | |
| $\kappa_{cat}/\kappa_m(S^{-1}mM^{-1})$ | 0.031 ± 0.001 | 20.3 ± 0.55 | 196 ± 9 | 582 ± 65 | 654 ± 43 | 685 ± 47 | 870 ± 35 | |
| Y48F49W | | | | | | | | ND |
| $\kappa_{cat}(S^{-1})$ | | 0.236 ± 0.016 | | | | | 1.99 ± 0.08 | |
| $\kappa_m$(mM) | ND[d] | 9.9 ± 1.8 | ND | ND | ND | ND | 4.9 ± 0.3 | |
| $\kappa_{cat}/\kappa_m(S^{-1}mM^{-1})$ | | 0.024 ± 0.003 | | | | | 0.408 ± 0.010 | |
| $\Delta(\Delta G)^c$(KJ mol$^{-1}$) | | 17.8 | | | | | 20.3 | |
| Y116W | | | | | | | | 498 |
| $\kappa_{cat}(S^{-1})$ | 0.69 ± 0.02 | 11.7 ± 0.2 | 19.4 ± 0.3 | 50.9 ± 1.9 | 50.0 ± 1.7 | 53.1 ± 1.9 | 56.0 ± 1.1 | |
| $\kappa_m$(mM) | 28.8 ± 2.5 | 0.98 ± 0.06 | 0.20 ± 0.01 | 0.20 ± 0.02 | 0.132 ± 0.014 | 0.143 ± 0.017 | 0.118 ± 0.008 | |
| $\kappa_{cat}/\kappa_m(S^{-1}mM^{-1})$ | 0.024 ± 0.001 | 12.0 ± 0.60 | 98 ± 6 | 256 ± 17 | 378 ± 30 | 372 ± 32 | 475 ± 25 | |
| $\Delta(\Delta G)$ (KJ mol$^{-1}$) | 0.67 | 1.39 | 1.84 | 2.17 | 1.45 | 1.62 | 1.60 | |
| Y175F | | | | | | | | 752 |
| $\kappa_{cat}(S^{-1})$ | 1.02 ± 0.05 | 21.2 ± 0.2 | 40.0 ± 0.6 | 80.1 ± 1.8 | 79.6 ± 1.9 | 76.5 ± 1.5 | 72.1 ± 0.8 | |
| $\kappa_m$(mM) | 40.1 ± 4.3 | 1.13 ± 0.04 | 0.29 ± 0.02 | 0.187 ± 0.012 | 0.120 ± 0.010 | 0.113 ± 0.008 | 0.095 ± 0.004 | |
| $\kappa_{cat}/\kappa_m(S^{-1}mM^{-1})$ | 0.025 ± 0.002 | 18.8 ± 0.5 | 136 ± 6 | 429 ± 19 | 666 ± 42 | 677 ± 37 | 761 ± 27 | |
| $\Delta(\Delta G)$ (KJ mol$^{-1}$) | 0.55 | 0.20 | 0.97 | 0.81 | −0.05 | 0.03 | 0.35 | |
| R241K | | | | | | | | 261 |
| $\kappa_{cat}(S^{-1})$ | 1.34 ± 0.08[b] | 20.1 ± 0.3 | 46.8 ± 1.0 | 73.5 ± 7.2 | 70.7 ± 2.1 | 75.8 ± 2.7 | 80.6 ± 1.6 | |
| $\kappa_m$(mM) | 39.3 ± 5.8- | 2.27 ± 0.11 | 0.62 ± 0.04 | 0.45 ± 0.09 | 0.19 ± 0.02 | 0.20 ± 0.02 | 0.20 ± 0.01 | |
| $\kappa_{cat}/\kappa_m(S^{-1}mM^{-1})$ | 0.034 ± 0.003 | 8.9 ± 0.3 | 76 ± 3 | 164 ± 18 | 368 ± 21 | 373 ± 25 | 411 ± 16 | |

TABLE 10-continued

Kinetic parameters of wild-type and mutant glucoamylase for hydrolysis of isomaltose and maltooligodextrins of DP 2-7

| Enzyme | Substrate | | | | | | | $\kappa_{cat}/K_m$ (G2) |
|---|---|---|---|---|---|---|---|---|
| | Isomaltose (iG2) | Maltose (G2) | Maltotriose (G3) | Maltotetraose (G4) | Maltopentaose (G5) | Maltohexaose (G6) | Maltoheptaose (G7) | $\kappa_{cat}/K_m$ (iG2) |
| $\Delta(\Delta G)^c$(KJ mol$^{-1}$) | −0.28 | 2.19 | 2.51 | 3.36 | 1.52 | 1.61 | 1.98 | |
| S411A | | | | | | | | 681 |
| $\kappa_{cat}$(S$^{-1}$) | 0.63 ± 0.02 | 18.9 ± 0.3 | 44.6 ± 0.1 | 58.5 ± 1.6 | 53.1 ± 1.2 | 54.7 ± 1.7 | 59.4 ± 0.6 | |
| $K_m$(mM) | 27.9 ± 2.9 | 1.26 ± 0.06 | 0.47 ± 0.04 | 0.182 ± 0.014 | 0.120 ± 0.009 | 0.115 ± 0.012 | 0.104 ± 0.004 | |
| $\kappa_{cat}/K_m$(S$^{-1}$mM$^{-1}$) | 0.022 ± 0.002 | 15.0 ± 0.5 | 94.1 ± 5.4 | 322 ± 18 | 443 ± 27 | 476 ± 41 | 570 ± 17 | |
| $\Delta(\Delta G)$(KJ mol$^{-1}$) | 0.84 | 0.80 | 1.94 | 1.56 | 1.15 | 0.96 | 1.12 | |
| S411G | | | | | | | | 402 |
| $\kappa_{cat}$(S$^{-1}$) | 0.93 ± 0.06 | 23.0 ± 0.4 | 55.1 ± 1.6 | 59.7 ± 1.8 | 75.1 ± 2.1 | 75.9 ± 4.3 | 84.0 ± 2.5 | |
| $K_m$(mM) | 26.2 ± 2.7 | 1.59 ± 0.08 | 0.50 ± 0.04 | 0.092 ± 0.010 | 0.094 ± 0.010 | 0.125 ± 0.024 | 0.132 ± 0.012 | |
| $\kappa_{cat}/K_m$(S$^{-1}$mM$^{-1}$) | 0.036 ± 0.004 | 14.5 ± 0.6 | 108 ± 6 | 649 ± 55 | 795 ± 61 | 609 ± 87 | 634 ± 41 | |
| $\Delta(\Delta G)$(KJ mol$^{-1}$) | −0.39 | 0.89 | 1.56 | −0.29 | −0.52 | 0.31 | 0.84 | |

[a]Determined at 45° C. in 0.05 M sodium acetate buffer, pH 4.4.
[b]Standard error.
[c]Changes of transition-state energy $\Delta(\Delta G) = -RT \ln[(\kappa_{cat}/K_m)_{mut}/(\kappa_{cat}/K_m)_{wt}]$.
[d]Not determined.

TABLE 11

Kinetic parameters of wild-type and mutant glucoamylases for hydrolysis of isomaltose, maltose and maltoheptaose

| Substrate | Wild-type | Mutant | | | | |
|---|---|---|---|---|---|---|
| | | S411G | S411A | S411C | S411H | S411D |
| Isomaltose (iG2) | | | | | | |
| $\kappa_{cat}$(S$^{-1}$) | 0.72 ± 0.01[b] | 0.93 ± 0.06 | 0.63 ± 0.02 | 0.22 ± 0.01 | ND[d] | ND[d] |
| $K_m$(mM) | 23.5 ± 0.6 | 26.2 ± 2.7 | 27.9 ± 2.9 | 12.3 ± 0.9 | | |
| $\kappa_{cat}/K_m$(S$^{-1}$mM$^{-1}$) | 0.031 ± 0.001 | 0.036 ± 0.004 | 0.022 ± 0.002 | 0.018 ± 0.001 | | |
| $\Delta(\Delta G)^c$(KJ mol$^{-1}$) | — | −0.39 | 0.84 | 1.4 | | |
| Maltose (G2) | | | | | | |
| $\kappa_{cat}$(S$^{-1}$) | 20.4 ± 0.2 | 23.0 ± 0.4 | 18.9 ± 0.3 | 7.78 ± 0.07 | 5.31 ± 0.15 | 4.36 ± 0.05 |
| $K_m$(mM) | 1.01 ± 0.03 | 1.59 ± 0.08 | 1.26 ± 0.06 | 0.53 ± 0.02 | 3.67 ± 0.25 | 3.58 ± 0.11 |
| $\kappa_{cat}/K_m$(S$^{-1}$mM$^{-1}$) | 20.3 ± 0.6 | 14.5 ± 0.6 | 15.0 ± 0.5 | 14.8 ± 0.6 | 1.45 ± 0.06 | 1.22 ± 0.03 |
| $\Delta(\Delta G)^c$(KJ mol$^{-1}$) | — | 0.89 | 0.80 | 0.83 | 6.98 | 7.43 |
| Maltoheptaose (G7) | | | | | | |
| $\kappa_{cat}/K_m$(S$^{-1}$) | 72.3 ± 0.9 | 84.0 ± 2.5 | 59.4 ± 0.6 | 33.0 ± 0.5 | 32.4 ± 0.9 | 15.8 ± 0.3 |
| $K_m$(mM) | 0.083 ± 0.004 | 0.132 ± 0.012 | 0.104 ± 0.004 | 0.070 ± 0.005 | 0.336 ± 0.024 | 0.148 ± 0.009 |
| $\kappa_{cat}/K_m$(S$^{-1}$mM$^{-1}$) | 870 ± 35 | 634 ± 41 | 570 ± 17 | 474 ± 25 | 97 ± 5 | 107 ± 5 |
| $\Delta(\Delta G)^c$(KJ mol$^{-1}$) | — | 0.84 | 1.12 | 1.60 | 5.81 | 5.54 |

[a]Determined at 45° C. in 0.05 M sodium acetate buffer, pH 4.4.
[b]Standard error.
[c]Changes of transition-state energy $\Delta(\Delta G) = -RT \ln[(\kappa_{cat}/K_m)_{mut}/(\kappa_{cat}/K_m)_{wt}]$.
[d]Not determined.

TABLE 12 pK values and optimum pH of wild-type and mutant glucoamylases for hydrolysis of maltose and maltoheptaose at 45° C.

| | Free enzyme (uncomplexed) | | | Enzyme-substrate complex (maltose-complexed) | | | Enzyme-substrate complex (maltoheptaose-complexed) | | |
|---|---|---|---|---|---|---|---|---|---|
| | pK$_1$ | pK$_2$ | pH$_{opt}$ | pK$_1$ | pK$_2$ | pH$_{opt}$ | pK$_1$ | pK$_2$ | pH$_{opt}$ |
| Wild-type | 2.77 | 5.80 | 4.29 | 2.11 | 5.85 | 3.98 | 2.60 | 6.78 | 4.69 |
| S411G | 3.01 | 5.57 | 4.29 | 2.68 | 5.81 | 4.24 | 3.22 | 6.73 | 4.98 |
| S411A | 3.11 | 5.86 | 4.49 | 3.32 | 6.32 | 4.82 | 3.91 | 7.18 | 5.54 |
| S411C | 3.26 | 5.86 | 4.56 | 3.32 | 6.38 | 4.85 | ND[a] | ND | ND |
| S411H | 3.10 | 5.01 | 4.05 | 3.58 | 4.69 | 4.13 | ND | ND | ND |
| S411D | 3.13 | 5.72 | 4.42 | 3.34 | 5.53 | 4.44 | ND | ND | ND |

[a]Not determined.

TABLE 13

Increases in free energies for thermal inactivation (ΔΔG‡) relative to wild-type GA calculated at 65° C.

| GA form | ΔΔG‡ (kJ/mol) |
|---|---|
| S436P | 0.5 |
| S30P | 1.6 |
| G137A | 0.8 |
| S-S | 1.2 |
| S-S/S436P | 2.2 |
| G137A/S436P | 2.0 |
| S30P/G137A | 4.5 |
| S-S/S30P | 3.5 |
| S-S/G137A | 2.7 |
| S-S/S30P/G137A | 4.4 |

[a]ΔΔG‡ greater than zero indiactes increased thermostability

TABLE 14

Decrease in the relative ratio of initial rate of isomaltose formation from 30% (w/v) glucose condensation reactions to that of glucose formation in 30% (w/v) maltodextrin M100 hydrolysis reactions.

| GA form | Relative ratios[a] |
|---|---|
| Wild-type | 1.00 |
| S-S | 0.24 |
| S30P | 0.77 |
| G137A | 0.54 |
| Y17SF | 0.76 |
| 300Loop | 0.47 |
| S411A | 0.40 |
| S411G | 0.38 |
| S436P | 0.70 |
| S-S/G137A | 0.81 |
| G121A/S411G | 0.44 |

All the above reactions were carried out in 0.05 M sodium acetate buffer, pH 4.4, at 55° C.
[a]Ratios lower than 1.00 indicate increased specificity for α-(1,4) over α-(1,6)-linked substrates.

TABLE 15

Increase in the optimum pH of the enzyme-substrate complex of mutant glucoamylases for hydrolysis of maltose at 45° C. compared to that of wild-type.

| GA form | pH$_{opt}$ Increase[a] |
|---|---|
| S411G | 0.26 |
| S411A | 0.84 |
| S411C | 0.86 |
| S411H | 0.15 |
| S411D | 0.46 |

[a]The pH optimum of the enzyme-substrate complex of wildtype glucoamylase for hydrolysis of maltose at 45° C. was pH 3.98.

TABLE 16

Specific activities, glucose yields and relative thermostabilities of wild-type and mutant GAs

| GA form | Specific activity[a] (IU/mg GA) | Glucose yield (%)[b] 35° C. | 45° C. | 55° C. | ΔΔG‡(kJ/mol) 65° C. | 75° C. |
|---|---|---|---|---|---|---|
| Wild-type | 20.6[c] ± 0.2[d] | 96.6[c] | 95.3[c] | 95.3[c] | — | — |
| SS | 18.3[f] ± 0.7 | 96.9[c] | 96.1[c] | 96.1[c] | 1.5[f] | ND[g] |
| Ser30→Pro. | 20.3[h] ± 0.9 | 96.3[c] | 94.9[c] | 95.9[c] | 1.6[h] | ND |
| Gly137→Ala | 22.0[i] ± 0.8 | 96.7[e] | 95.4[e] | 96.2[e] | 0.8[i] | 1.9[i] |
| 311–314 Loop | 11.9 ± 0.5 | 97.1[e] | 96.4[e] | 96.2[e] | −2.2 | −2.5 |
| Ser411→Ala | 12.4 ± 0.5 | 97.0 | 96.3 | 96.4 | −2.7 | −1.8 |
| Ser436→Pro | 15.9[c] ± 1.0 | 95.5[c] | 93.5[c] | 95.7[c] | 0.5[c] | 1.0[c] |
| SS/Ser30→Pro | 21.2[h] ± 0.5 | 96.8 | 95.9 | 96.3 | 3.5[h] | ND |
| SS/Gly137→Ala | 24.2[f] ± 0.8 | 96.9 | 96.4 | 96.5 | 2.7[f] | ND |
| SS/311→314 Loop | 12.8 ± 0.6 | 97.5 | 96.7 | 96.5 | −1.3 | −0.5 |
| SS/Ser411→Ala | 14.9 ± 0.7 | 97.4 | 96.6 | 96.7 | −1.3 | −0.2 |
| SS/Ser436→Pro | 22.5[f] ± 1.8 | 96.2 | 95.1 | 95.3 | 2.2[f] | ND |
| Ser30→Pro/Gly137→Ala | 24.0[h] ± 1.2 | 96.6 | 95.6 | 96.6 | 4.5[h] | ND |
| Ser30→Pro/311–314 Loop | 13.5 ± 0.9 | 96.8 | 96.0. | 96.4 | −0.9 | ND |
| Ser30→Pro/Ser411→Ala | 15.3 ± 1.1 | 96.8 | 95.9 | 96.5 | −1.1 | ND |
| Gly137→Ala/311-314 Loop | 13.7 ± 0.8 | 97.2 | 96.2 | 96.7 | −1.8 | −1.0 |
| Gly137→Ala/Ser411→Ala | 15.1 ± 0.6 | 97.1 | 96.4 | 96.7 | −2.0 | −0.5 |
| Gly137→Ala/Ser436→Pro | 25.0[f] ± 0.9 | 96.0 | 94.8 | 95.2 | 2.2[f] | ND |
| 311–314 Loop/Ser411→Ala | 11.7 ± 0.3 | 97.4 | 96.5 | 96.6 | −3.3 | −3.9 |
| SS/Ser30→Pro/Gly137→Ala | 24.5[h] ± 0.2 | 97.1 | 96.0 | 96.4 | 4.4[h] | ND |
| Ser30→Pro/Gly137→Ala/311–314 Loop | 13.3 ± 0.5 | 97.1 | 96.6 | 96.4 | 1.5 | ND |
| Ser30→Pro/Gly137→Ala/Ser411→Ala | 15.0 ± 0.9 | 97.0 | 96.5 | 96.6 | 1.7 | ND |

[a]50° C., pH 4.5, 4% maltose substrate
[b]pH 4.4, 30% (w/v) maltodextrin substrate (values averaged over DE 10, DE 18 and DE 25 maltodextrins)
[c]Li et al. (1997)
[d]Standard error
[e]Liu et al. (1998)
[f]Li et al. (1998)
[g]Not determined
[h]Allen et al. (1998)
[i]Chen et al. (1996)

TABLE 17

Initial rates of glucose and iG₂ formation in the hydrolysis of 30% (w/v) maltodextrins and condensation of 30% (w/v) glucose, respectively, and their relative ratios for wild-type and mutant GAs at pH 4.4 and 35, 45 and 55° C.

| GA form | Initial rates (mol/mol GA · s) Glucose DE 10 | DE 18 | DE 25 | $iG_2 \times 10^3$ | $\dfrac{\text{Initial rate } iG_2 \times 10^3}{\text{Initial rate glucose}}$ DE 10 | DE 18 | DE 25 |
|---|---|---|---|---|---|---|---|
| 35° C. | | | | | | | |
| Wildtype[a] | 32.8 ± 1.4[b] | 36.3 ± 1.6 | 38.6 ± 2.1 | 15.2 ± 0.5 | 0.46 | 0.42 | 0.39 |
| SS[a] | 48.1 ± 2.2 | 47.9 ± 2.4 | 46.8 ± 2.9 | 7.07 ± 0.33 | 0.15 | 0.15 | 0.15 |
| Ser30 → Pro[a] | 39.7 ± 1.8 | 46.1 ± 2.6 | 46.3 ± 3.4 | 22.9 ± 0.8 | 0.58 | 0.50 | 0.49 |
| Gly137 → Ala[a] | 44.9 ± 2.3 | 48.6 ± 2.7 | 49.2 ± 3.3 | 19.1 ± 0.7 | 0.43 | 0.39 | 0.39 |
| 311–314 Loop[a] | 20.9 ± 1.1 | 23.9 ± 1.3 | 24.6 ± 1.7 | 6.71 ± 0.24 | 0.32 | 0.28 | 0.27 |
| Ser411 → Ala | 9.14[c] ± 0.64 | 9.28 ± 0.77 | 9.33 ± 0.69 | 2.92[c] ± 0.28 | 0.32[c] | 0.31 | 0.31 |
| Ser436 → Pro[a] | 45.1 ± 2.6 | 53.3 ± 3.3 | 55.5 ± 4.2 | 47.5 ± 1.8 | 1.05 | 0.89 | 0.86 |
| SS/Ser30 → Pro | 42.6 ± 2.6 | 44.3 ± 2.7 | 44.9 ± 2.9 | 15.9 ± 0.6 | 0.37 | 0.36 | 0.35 |
| SS/Gly137 → Ala | 46.5 ± 2.5 | 46.8 ± 2.4 | 47.2 ± 2.7 | 12.6 ± 0.4 | 0.27 | 0.27 | 0.27 |
| SS/311–314 Loop | 35.4 ± 1.7 | 37.7 ± 1.9 | 40.1 ± 2.2 | 5.83 ± 0.34 | 0.16 | 0.15 | 0.15 |
| SS/Ser411 → Ala | 23.3 ± 1.2 | 24.1 ± 1.4 | 24.5 ± 1.3 | 5.13 ± 0.31 | 0.22 | 0.21 | 0.21 |
| SS/Ser436 → Pro | 43.3 ± 2.3 | 45.5 ± 2.9 | 44.9 ± 2.6 | 30.2 ± 1.3 | 0.70 | 0.66 | 0.67 |
| Ser30 → Pro/Gly137 → Ala | 41.6 ± 2.7 | 40.8 ± 2.4 | 42.2 ± 2.5 | 22.2 ± 1.1 | 0.53 | 0.54 | 0.53 |
| Ser30 → Pro/311–314 Loop | 33.1 ± 1.4 | 34.9 ± 1.5 | 37.7 ± 1.9 | 14.8 ± 0.5 | 0.45 | 0.42 | 0.39 |
| Ser30 → Pro/Ser411 → Ala | 23.1 ± 1.3 | 25.6 ± 1.7 | 24.9 ± 1.6 | 12.7 ± 0.4 | 0.55 | 0.50 | 0.51 |
| Gly137 → Ala/311–314 Loop | 33.6 ± 1.7 | 36.9 ± 1.9 | 38.8 ± 2.2 | 12.2 ± 0.4 | 0.36 | 0.33 | 0.31 |
| Gly137 → Ala/Ser411 → Ala | 26.7 ± 1.5 | 27.5 ± 1.6 | 29.3 ± 1.9 | 11.1 ± 0.4 | 0.42 | 0.40 | 0.38 |
| Gly137 → Ala/Ser436 → Pro | 44.4 ± 3.1 | 45.1 ± 3.3 | 46.2 ± 3.5 | 36.3 ± 1.7 | 0.82 | 0.80 | 0.79 |
| 311–314 Loop/Ser411 → Ala | 15.9 ± 0.9 | 16.4 ± 1.1 | 17.3 ± 1.3 | 4.88 ± 0.33 | 0.31 | 0.30 | 0.28 |
| SS/Ser30 → Pro/Gly137 → Ala | 43.9 ± 2.8 | 43.7 ± 2.9 | 44.1 ± 2.6 | 17.5 ± 0.9 | 0.40 | 0.40 | 0.40 |
| Ser30 → Pro/Gly137 → Ala/311–314 Loop | 31.3 ± 1.6 | 33.7 ± 1.9 | 35.9 ± 2.1 | 14.5 ± 0.6 | 0.46 | 0.43 | 0.40 |
| Ser30 → Pro/Gly137 → Ala/Ser411 Ala | 24.6 ± 1.3 | 25.2 ± 1.5 | 25.5 ± 1.4 | 12.3 ± 0.7 | 0.50 | 0.49 | 0.48 |
| 45° C. | | | | | | | |
| Gly137 → Ala/Ser411 → Ala | 67.9 ± 4.6 | 70.1 ± 5.3 | 72.3 ± 5.1 | 24.4 ± 1.6 | 0.36 | 0.35 | 0.34 |
| Gly137 → Ala/Ser436 → Pro | 120 ± 8 | 118 ± 9 | 123 ± 10 | 81.6 ± 6.7 | 0.68 | 0.69 | 0.66 |
| 311–314 Loop/Ser411 → Ala | 42.4 ± 2.9 | 44.6 ± 3.3 | 46.2 ± 3.6 | 11.1 ± 0.7 | 0.26 | 0.25 | 0.24 |
| SS/Ser30 → Pro/Gly137 → Ala | 117 ± 7 | 120 ± 8 | 126 ± 10 | 38.5 ± 1.9 | 0.33 | 0.32 | 0.31 |
| Ser30 → Pro/Gly137 → Ala/311–314 Loop | 85.3 ± 5.3 | 87.7 ± 5.6 | 89.2 ± 5.7 | 34.1 ± 2.3 | 0.40 | 0.39 | 0.38 |
| Ser30 → Pro/Gly137 → Ala/Ser411 → Ala | 70.1 ± 4.4 | 72.2 ± 4.6 | 73.6 ± 4.9 | 29.5 ± 1.7 | 0.42 | 0.41 | 0.40 |
| 55° C. | | | | | | | |
| Wild-type[a] | 240 ± 15 | 258 ± 17 | 313 ± 23 | 129 ± 7 | 0.54 | 0.50 | 0.41 |
| SS[a] | 268 ± 17 | 311 ± 20 | 322 ± 22 | 32.4 ± 2.7 | 0.13 | 0.11 | 0.11 |
| Ser30 → Pro[a] | 284 ± 20 | 334 ± 23 | 346 ± 24 | 119 ± 6 | 0.42 | 0.36 | 0.34 |
| Gly137 → Ala[a] | 288 ± 21 | 333 ± 23 | 325 ± 23 | 83.4 ± 5.4 | 0.29 | 0.25 | 0.26 |
| 311–314 Loop[a] | 191 ± 14 | 205 ± 16 | 221 ± 15 | 49.5 ± 2.7 | 0.26 | 0.24 | 0.22 |
| Ser411 → Ala | 72.5[c] ± 4.2 | 77.3 ± 5.1 | 77.6 ± 4.9 | 15.5[c] ± 0.6 | 0.21[c] | 0.20 | 0.20 |
| Ser436 → Pro[a] | 301 ± 22 | 322 ± 25 | 330 ± 23 | 124 ± 8 | 0.41 | 0.39 | 0.38 |
| SS/Ser30 → Pro | 286 ± 19 | 291 ± 20 | 298 ± 22 | 76.6 ± 4.5 | 0.27 | 0.26 | 0.26 |
| SS/Gly137 → Ala | 306 ± 24 | 311 ± 23 | 315 ± 24 | 60.4 ± 3.6 | 0.20 | 0.19 | 0.19 |
| Wild-type[a] | 101 ± 5 | 102 ± 5 | 98.7 ± 5.3 | 39.6 ± 2.9 | 0.39 | 0.39 | 0.40 |
| SS[a] | 129 ± 6 | 125 ± 5 | 110 ± 6 | 16.4 ± 1.0 | 0.13 | 0.13 | 0.15 |
| Ser30 → Pro[a] | 98.8 ± 5.4 | 107 ± 5 | 119 ± 6 | 51.0 ± 2.2 | 0.52 | 0.48 | 0.43 |
| Gly137 → Ala[a] | 102 ± 6 | 110 ± 5 | 112 ± 7 | 30.7 ± 1.8 | 0.30 | 0.28 | 0.27 |
| 311–314 Loop[a] | 61.2 ± 3.8 | 68.4 ± 3.4 | 70.3 ± 5.1 | 14.6 ± 1.1 | 0.24 | 0.21 | 0.21 |
| Ser411 → Ala | 26.2 ± 1.7 | 28.1 ± 1.9 | 29.3 ± 2.2 | 6.62 ± 0.43 | 0.25 | 0.24 | 0.23 |
| Ser436 → Pro[a] | 87.9 ± 5.3 | 125 ± 7 | 113 ± 7 | 68.3 ± 3.6 | 0.78 | 0.55 | 0.60 |
| SS/Ser30 → Pro | 114 ± 7 | 117 ± 7 | 115 ± 8 | 35.6 ± 1.0 | 0.31 | 0.30 | 0.31 |
| SS/Gly137 → Ala | 124 ± 9 | 126 ± 8 | 127 ± 9 | 28.3 ± 1.2 | 0.23 | 0.22 | 0.22 |
| SS/311–314 Loop | 96.4 ± 6.2 | 101 ± 7 | 108 ± 7 | 13.3 ± 0.9 | 0.14 | 0.13 | 0.12 |
| SS/Ser411 → Ala | 62.5 ± 4.9 | 64.1 ± 5.2 | 66.6 ± 5.5 | 11.6 ± 0.6 | 0.19 | 0.18 | 0.17 |
| SS/Ser436 → Pro | 116 ± 7 | 117 ± 8 | 122 ± 9 | 67.5 ± 4.1 | 0.58 | 0.58 | 0.55 |
| Ser30 → Pro/Gly137 → Ala | 112 ± 8 | 110 ± 7 | 117 ± 8 | 49.8 ± 3.3 | 0.44 | 0.45 | 0.43 |
| Ser30 → Pro/311–314 Loop | 90.3 ± 6.0 | 94.1 ± 6.2 | 96.8 ± 6.5 | 30.9 ± 2.1 | 0.34 | 0.33 | 0.32 |
| Ser30 → Pro/Ser411 → Ala | 60.9 ± 3.9 | 62.6 ± 4.4 | 64.3 ± 4.7 | 28.9 ± 1.9 | 0.47 | 0.46 | 0.45 |
| Gly137 → Ala/311–314 Loop | 92.6 ± 6.6 | 96.1 ± 7.3 | 102 ± 8 | 27.8 ± 1.7 | 0.30 | 0.29 | 0.27 |
| SS/311–314 Loop | 224 ± 14 | 236 ± 16 | 238 ± 15 | 26.9 ± 1.8 | 0.12 | 0.11 | 0.11 |
| SS/Ser411 → Ala | 159 ± 11 | 164 ± 11 | 166 ± 12 | 24.7 ± 1.3 | 0.16 | 0.15 | 0.15 |
| SS/Ser436 → Pro | 292 ± 19 | 297 ± 20 | 306 ± 23 | 148 ± 10 | 0.51 | 0.50 | 0.48 |
| Ser30 → Pro/Gly137 → Ala | 283 ± 22 | 291 ± 25 | 298 ± 27 | 109 ± 6 | 0.39 | 0.37 | 0.37 |
| Ser30 → Pro/311–314 Loop | 232 ± 15 | 222 ± 13 | 236 ± 16 | 70.3 ± 4.9 | 0.30 | 0.32 | 0.30 |
| Ser30 → Pro/Ser411 → Ala | 159 ± 11 | 166 ± 12 | 170 ± 14 | 62.4 ± 4.2 | 0.39 | 0.38 | 0.37 |
| Gly137 → Ala/311–314 Loop | 221 ± 15 | 226 ± 15 | 233 ± 17 | 59.7 ± 4.0 | 0.27 | 0.26 | 0.26 |
| Gly137 → Ala/Ser411 → Ala | 180 ± 12 | 181 ± 11 | 188 ± 13 | 50.1 ± 3.3 | 0.28 | 0.28 | 0.27 |
| Gly137 → Ala/Ser436 → Pro | 305 ± 24 | 312 ± 26 | 320 ± 25 | 175 ± 12 | 0.57 | 0.56 | 0.55 |
| 311–314 Loop/Ser411 → Ala | 115 ± 8 | 111 ± 7 | 122 ± 9 | 24.3 ± 1.6 | 0.21 | 0.22 | 0.20 |
| SS/Ser30 → Pro/Gly137 → Ala | 297 ± 23 | 306 ± 23 | 314 ± 26 | 73.5 ± 4.1 | 0.25 | 0.24 | 0.23 |

TABLE 17-continued

Initial rates of glucose and iG$_2$ formation in the hydrolysis of 30% (w/v) maltodextrins and condensation of 30% (w/v) glucose, respectively, and their relative ratios for wild-type and mutant GAs at pH 4.4 and 35, 45 and 55° C.

| GA form | Initial rates (mol/mol GA · s) Glucose DE 10 | DE 18 | DE 25 | iG$_2$ × 10$^3$ | $\frac{\text{Initial rate iG}_2 \times 10^3}{\text{Initial rate glucose}}$ DE 10 | DE 18 | DE 25 |
|---|---|---|---|---|---|---|---|
| Ser30 → Pro/Gly137 → Ala/311–314 Loop | 217 ± 15 | 223 ± 17 | 231 ± 19 | 73.5 ± 4.9 | 0.34 | 0.33 | 0.32 |
| Ser30 → Pro/Gly137 → Ala/Ser411 → Ala | 180 ± 12 | 185 ± 14 | 187 ± 14 | 62.3 ± 4.1 | 0.35 | 0.34 | 0.33 |

[a]Liu et al. (1998)
[b]Standard error
[c]Fang et al. (1998a)

TABLE 18

Changes in activation energies for thermoinactivation ($\Delta\Delta G^\ddagger$) at 65° C. and temperatures at which the enzyme is 50% inactivated after 10 minutes ($\Delta T_m$) relative to wild-type GA.

| GA form | $\Delta\Delta G^\ddagger$ (kJ.mol) | $\Delta T_m$ |
|---|---|---|
| S30P | 1.6 | 1.7 |
| D345P | 0.5 | 0.4 |
| E408P | −7.2 | −6.7 |
| S30P/G137A | 4.5 | 3.5 |
| S-S/S30P | 3.5 | 3.2 |
| S-S/S30P/G137A | 4.4 | 3.9 |

TABLE 19

Kinetic patameters for wild-type and mutant Gas at pH 4.5 and 35° C. using maltose as substrate.

| GA form | $K_m$ (mM) | $K_{cat}$ (s$^{-1}$) | $K_{cat}$/KM (s$^{-1}$ mM$^{-1}$) |
|---|---|---|---|
| Wild-type | 1.09 ± 0.1 | 8.91 ± 0.2 | 8.21 ± 0.5 |
| S30P | 1.49 ± 0.1 | 10.24 ± 0.3 | 6.89 ± 0.4 |
| D345P | 1.27 ± 0.1 | 11.19 ± 0.4 | 8.78 ± 0.6 |
| E408P | 1.29 ± 0.1 | 12.00 ± 0.4 | 9.28 ± 0.6 |
| S30P/G137A | 1.55 ± 0.1 | 11.18 ± 0.3 | 7.23 ± 0.4 |
| S-S/S30P | 1.31 ± 0.1 | 9.95 ± 0.3 | 7.58 ± 0.4 |
| S-S/S30P/G137A | 1.29 ± 0.1 | 10.57 ± 0.2 | 8.19 ± 0.3 |

TABLE 20

Specific activities of wild-type and mutant Gas at pH 4.5 and 50° C. using maltose as substrate.

| GA form | Specific Activity (IU/mg) |
|---|---|
| Wild-type | 21.1 ± 0.1 |
| S30P | 20.3 ± 0.9 |
| D345P | 21.2 ± 0.5 |
| E408P | 21.7 ± 0.5 |
| S30P/G137A | 24.0 ± 1.2 |
| S-S/S30P | 21.2 ± 0.5 |
| S-S/S30P/G137A | 24.5 ± 0.2 |

REFERENCES

Ahearn and Klibanov. The Mechanism of Irreversible Enzyme Inactivation at 100° C. *Science*, 228, 1280 (1985).

Ahearn, et al. Control of Oligomeric Enzyme Thermostability by Protein Engineering. *Proc. Nat. Acad. Sci. U. S. A.*, 84, 675 (1987).

Aleshin, et al., 1992. Crystal structure of glucoamylase from *Aspergillus awamori* var. X100 to 2.2-A resolution. *J. Biol. Chem.* 267:19291–19298.

Aleshin, et al., 1994. Refined structure for the complex of acarbose with glucoamylase from *Aspergillus awamori* var. X100 to 2.4-A resolution. *J. Biol. Chem.* 269:15631–15639.

Aleshin et al., 1994, *J. Mol. Biol*, 238:575–591

Aleshin, et al., 1996. Crystallographic complexes of glucoamylase with maltooligosaccharide analogs: relationship of stereochemical distortions at the nonreducing end to the catalytic mechanism. *Biochemistry.* 35: 8319–8328.

Argos, et al. Thermal Stabilityand Protein Structure. *Biochemistry,* 18, 5698 (1979).

Bakir et al (1993) Protein Eng. 6:939–946

Balaji, et al 1989. Modification of protein stability by introduction of disulfide bridges and prolines; Geometric criteria for mutation sites. *Biochem. Biophys. Res. Commun.* 160:109–114.

Banks, W. and Greenwood, C. J. 1971. The specific estimation of glucose using glucose oxidase. Starke. 23:222–228.

Boel, et al. Glucoamylases G1 and G2 from *Aspergillus niger* Are Synthesized from Two Different but Closely Related mRNAs. *EMBO J.,* 3, 1097 (1984).

Bradford. A Rapid and Sensitive Method for the Quantitation of Microgram Quantities of Protein Utilizing the Principle of Protein—Dye Binding. *Anal. Biochem.,* 72, 248(1976).

Chen, et al (1996). Effect of replacing helical glycine residues with alanine on reversible and irreversible stability and production of *Aspergillus awamori* glucoamylase. *Protein Eng* 9:499–505.

Chen, et al (1995) *Protein Eng.,* 8, 575–582.

Chen, et al (1994a)s. Increased thermostability of Asn182→Ala mutant *Aspergillus awamori* glucoamylase. *Biotechnology and Bioengineering.* 43:101–105.

Chen, et al (1994b) Biochem. J., 301, 275–281.

Clarke a nd Svensson. Identification of an Essential Tryptophanyl Residue in the Primary Structure of Glucoamylase G2 from *Aspergillus niger. Carlsberg Res. Comm.,* 49, 559 (1984).

Clarke and Fersht, (1993) *Biochemistry,* 32, 4322–4329.

Cole, et al. Stable Expression of *Aspergillus awamoi* Glucoamylase in Distiller's Yeast. *Biol Technol.,* 6, 417 (1988).

Coutinho and Reilly, (1994a) *Protein Eng.,* 7, 393–400.

Coutinho and Reilly, 1994b. Structural similarities in glucoamylases by hydrophobic cluster analysis. *Protein Eng.* 7:749–760.

Fierobe et al., 1996. Mutational modulation of substrate bond-type specificity and thermostability of glucoamylase from *Aspergillus awamori* by replacement with short. homologue active site sequences and thiol/disulfide engineering; *Biochemistry.* 35:8696–8704.

Frandson et al., 1994. Biochemistry 33:13808–13816.
Garfin, (1990) In: Guide to protein purification. M. P. Deutscher, Ed. *Methods in Enzymology.* vol. 1.82. Academic Press, San Diego, Calif. pp. 425–441.
Gunnarsson, et al. Structural Studies on the O-Glycosidically Linked Carbohydrate Chains of Glucoamylase G1 from *Aspergillus niger. Eur. L. Biochem.,* 145, 463 (1984). Habeeb, (1972). Methods in *Enzymology.* vol. 25. Academic Press, San Diego, Calif. pp. 457–464.
Harris et al., 1993. Refined structure for the complex of 1-deoxynojirimycin with glucoamylase from *Aspergillus awamori* var. X100 to 2.4-A resolution. *Biochemistry.* 32:1618–1626.
Hiromi et al., 1983, Mol. Cell. Biochem, 51:79–95
Hiromi et al. (1966) *J. Biochem* 59:469–475
Hurley, et al., 1992. Flexible-geometry conformational energy maps for the amino acid residue preceding a proline. *Biopolymers.* 32:1443–1446.
Imanaka, et al. A New Way of Enhancing the Thermostability of Proteases. *Nature,* 324, 695 (1986).
Innis, et al. Expression, Glycosylation, and Secretion of an *Aspergillus Glucoamylase* by *Saccharomyces cerevisiae. Science,* 228, 21–26 (1985).
Itoh, et al. Nucleotide Sequence of the Glucoamylase Gene GLU1 from *Saccharomycopsis fibuligera. J. Bacteriol.,* 169, 4171 (1987).
Klibanov. Stabilization of Enzymes Against Thermal Inactivation. *Adv. Appl. Microbiol.,* 29, 1 (1983).
Knowles, et al. Cellulase Families and.Their Genes. *Trends Biotechnol.,* 5, 255 (1987).
Kunkel. Rapid and Efficient Site-Specific Mutagenesis Without Phenotype Selection. *Proc. Nat. Acad. Sci. U. S. A.,* 82, 448 (1985).
Kunkel, et al 1987. Rapid and efficient site-specific mutagenesis without phenotypic selection. *Methods Enzymol.* 154:367–382.
Lee, et al. Pilot Plant Production of Glucose with Glucoamylase Immobilized to Porous Silica. *Biotechnol. Bioeng.,* 16, 1507 (1976).
Leatherbarrow and Fersht. Protein Engineering. *Protein Eng.,* 1, 7 (1986).
Matthews, et al., 1987. Enhanced protein thermostability fromsite-directed mutations that decrease the entropy of unfolding. *Proc. Natl. Acad. Sci. U. S. A.* 84:6663–6667.
MacArthur and Thornton, 1991. Influence of proline residues on protein conformation. *J. Mol. Biol.* 218:397–412.
Masumura, et al (1989) *Nature,* 342, 291–293.
Matsumura and Aiba. Screening for Thermostable Mutant of Kanamycin Nucleotidyltransferase by the Use of a Transformation System for a Thermophile, *Bacillus stearothermophilus. J. Biol. Chem.,* 260, 15298 (1985).
Matsumura, et al. A Cumulative Effect of Intragenic Amino Acid Replacements on the Thermostability of a Protein. *Nature,* 323, 356 (1986).
Matsuura, et al. Structure and Possible Catalytic Residues of Taka-Amylase A. *J. Biochem.,* 95, 697 (1984).
McIlvane (1921) Biochem. J. 49:183–6.
Meagher et al., 1989, Biotechnol Bioeng. 34:681–688
Munch and Tritsch. Irreversible Thermoinactivation of Glucoamylase from *Aspergillus niger* and Thermostabilization by Chemical Modification of Carboxyl Groups. *Biochim. Biophys. Acta,* 1041, 111 (1990).
Nikolov, et al. Kinetics, Equilibria, and Modeling of the Formation of Oligosaccharides from D-Glucose by *Aspergillus niger* Glucoamylases I and II. *Biotechnol. Bioeng.,* 34, 694 (1989).
Nosoh and Sekiguchi. Protein Engineering for Thermostability. *Biocatal.,* 1, 257 (1988).
Nunberg, et.al. Molecular Cloning and Characterization of the Glucoamylase Gene of *Aspergillus awamori. Mol. Cell. Biol.,* 4, 2306 (1984).
Pakula and Sauer. Genetic Analysis of Protein Stability and Function. *Ann. Rev. Genet.,* 23, 289 (1989).
Perry and Wetzel. Disulfide Bond Engineered into T4 Lysozyme: Stabilization of the Protein Toward Thermal Inactivation. *Science,* 226, 555 (1984).
Pollitt and Zalkin, (1983). *J. Bacteriology,* 153, 27–32.
Rabbo and Terkildsen (1960). Scandinav. J. & Lab. Investigation 12:402–407
Ramachandran, et al., 1963. Stereochemistry of polypeptide chain configurations. *J. Mol. Biol.* 7:95–99.
Robyt & Mukerjea (1994) Carbohydr. Res. 251:187–202
Savel'ev and Firsov. Carboxyl Groups at the Active Site of Glucoamylase from *Aspergillus awamori. Biochemistry (U. S. S. R.),* 47, 1365 (1982).
Savel'ev, et al. Study of the Active Center of Glucoamylase from *Aspergillus awamori. Biochemistry (U. S. S. R.),* 47, 330 (1982).
Semimaru, et al (1995) *Appl. Environ. Microbiol.,* 61, 2885–2990.
Sierks & Svensson (1994) Protein Eng. 7:1479–1480
Sierks, et al. Site-Directed Mutagenesis at the Active Site Trp120 of *Aspergillus awamori* Glucoamylase. *Protein Eng.,* 2, 621 (1989).
Sierks, et al. Catalytic Mechanism of Fungal Glucoamylase as Defined by Mutagenesis of Asp176, Glu179, and Glu180 in the Enzyme from *Aspergillus awamori.* Protein Eng., 3, 193 (1990).
Smith, et al., 1985. Measurement of protein using bicinchoninoc acid. *Anal Biochem.* 150:76–85.
Stoffer, et al., 1995. Refined structure for the complex of D-gluco-dihydroacarbose with glucoamylase from *Aspergillus awamori* var. X100 to 2.2 A resolution: dual conformations for the extended inhibitorshbound to the active site of glucoamylase. *FEBS Letters.* 358:57–61.
Suzuki, et al., 1987. A strong correlation between the increase in the number of proline residues and the rise in thermostability of five Bacillus oligo-1,6-glucosidases. *Appl. Microbiol. Biotechnol.* 26:546–551.
Suzuki, et al., 1991. A hyperthermostable pullulanase produced by an extreme thermophile, Bacillus flavocaldarius KP 1228, and evidence for the proline theory of increasing protein thermostability. *Appl. Microbiol. Biothnol.* 34:707–714..
Suzuki, 1989; A general principle of increasing protein thermostability. *Proc. Jpn. Acad.* Ser B. 65:146–148.
Suzuki, et al. Site-Directed Mutagenesis Reveals Functional Contribution of Thr218, Lys220, and Asp304 in Chymosin. *Protein Eng.,* 4, 69 (1990).
Svensson, Regional Distant Sequence Homology Between Amylases, α-Glucosidases and Transglycosylases. *FEBS Lett.,* 230, 72 (1988).
Svensson, et al. Characterization of Two Forms of Glucoamylase from *Aspergillus niger. Carlsberg Res. Commun.,* 47, 55 (1982).
Svensson, et al. The Complete Amino Acid Sequence of the Glycoprotein, Glucoamylase G1, from *Aspergillus niger. Carlsberg Res. Commun.,* 48, 529–544 (1983).
Svensson, et al. Sequence Homology Between Putative Raw-Starch Binding Domairis from Different Starch-Degrading Enzymes. *Biochem. J. Lett.,* 264, 309 (1989).
Svensson, et al. Identification of Carboxylic Acid Residues in Glucoamylase G2 from *Aspergillus niger* That Participate in Catalysis and Substrate Binding. *Eur. J. Biochem.,* 188, 29 (1990).

Tanaka et al., 1983, J. Biochem., 93:1037–1043

Watanabe, et al., 1994. Multiple proline substitutions cumulatively thermostabilize *Bacillus cereus* ATCC7064 oligo-1,6-glucosidase. *Eur. J. Biochem.* 226:277–283.

Wasserman. Thermostable Enzyme Production. *Food Technol.*, 38, 78 (1984).

Wetzel, R. (1987) *Trends Biochem. Sci.*, 12, 478–482.

Williamson, et al (1992) *Biochem. J.*, 282, 423–428.

Ackers, G. K. and Smith, F. R. (1985) *Annu. Rev. Biochem.*, 54, 597–629.

Aleshin, A., Golubev, A., Firsov, L. M. and Honzatko, R. B. (1992) *J. Biol. Chem.*, 267, 19291–19298.

Aleshin, A. E. Firsov,. L. M. and Honzatko, R. B. (1994) *J. Biol. Chem.*, 269, 15631–15639.

Allen, M., Coutinho, P. M. and Ford, C. (1998) *Protein Eng.*, accepted for publication.

Balaji, V. N., Mobasser, A. and Rao, S. N. (1989) *Biochem. Biophys. Res. Commun.*, 160, 109–114.

Carter, P. J., Winter, G., Wilkinson, A. J. and Fersht, A. R. (1984) *Cell*, 38, 835–840.

Carter, P., Nilsson, B., Burnier, J. P., Burdick, D. and Wells, J. A. (1989) *Proteins: Struct. Funct. Genet.*, 6, 240–248.

Chen, H.-M., Ford, C. and Reilly, P. J. (1994) *Biochem. J.*, 30, 275–281.

Chen, H.-M., Li, Y., Panda, T., Buehler, F. U., Ford, C. and Reilly, P. J. (1996) *Protein Eng.*, 9, 499–505.

Corn Annual (1998) Corn Refiners Association, Inc., Washington, D.C

Coutinho, P. M. (1996) Ph.D. Dissertation, Iowa State University, Ames, Iowa.

Coutinho, P. M. and Reilly, P. J. (1994a) *Protein Eng.*, 7, 393–400.

Coutinho, P. M. and Reilly, P. J. (1994b) *Protein Eng.*, 7, 749–760.

Coutinho, P. M. and Reilly, P. J. (1997) *Proteins: Struct. Funct Genet.*, 29, 334–347.

Cunningham, B. C. and Wells, J. A. (1987) *Protein Eng.*, 1, 319–325.

Fang, T.-Y. and Ford, C. (1998) *Protein Eng.*, 11, 383–388.

Fang, T.-Y., Coutinho, P. M., Reilly, P. J. and Ford, C. (1998a) *Protein Eng.*, 11, 119–126.

Fang, T.-Y., Honzatko, R. B., Reilly, P. J. and Ford, C. (1998b) *Protein Eng.*, 11, 127–133.

Fierobe, H.-P., Stoffer, B. B., Frandsen, T. P. and Svensson, B. (1996) *Biochemistry*, 35, 8696–8704.

Frandsen, T. P., Christensen, T., Stoffer, B. Lehmbeck, J., Dupont, C., Honzatko, R. B. and Svensson, B. (1995) *Biochemitry*, 34, 10162–10169.

Frandsen, T. P., Stoffer, B., Palcic, M. M., Hof, S. and Svensson, B. (1996) *J. Mol. Biol.*, 263, 79–89.

Hecht, M. H., Sturtevant, J. M. and Sauer, R. t. (1986) *Proteins: Struct. Funct. Genet.*, 1, 43–46.

Hehre, E. J., Okada, G. and Genghof, D. S. (1969) *Arch. Biochem. Biophys.*, 135, 74–89.

Hiromi, K., Takahashi, K., Hamauzu, Z. and Ono, S. (1966a) *J. Biochem.*, 59, 469–475.

Hiromi, K., Kawai, M. and Ono, S. (1966b) *J. Biochem.*, 59, 476–480.

Li, Y., Reilly, P. J. and Ford, C. (1997) *Protein Eng.*, 10, 1199–1204.

Li, Y., Coutinho, P. M. and Ford, C. (1998) *Protein Eng.*, accepted for publication.

Liao, H., McKenzie, T. and Hageman, R. (1986) *Proc. Natl. Acad Sci. U.S.A.*, 83, 576–580.

Liu, H.-L., Coutinho, P. M., Ford, C. and Reilly, P. J. (1998) *Protein Eng.*, 11, 389–398.

Matsumura, M., Signor, G. and Matthews, B. W. (1989) *Nature*, 342, 291–294.

Meagher, M. M. and Reilly, P. J. (1989) *Biotechnol. Bioeng.*, 34, 689–693.

Natarajan, S. and Sierks, M. R. (1996) *Biochemistry*, 35, 15269–15279.

Nikolov, Z. L. and Reilly, P. J. (1991) *Biocatalysts for Industry*, Dordick, J. S., ed., Plenum, New York, pp. 37–62.

Nikolov, Z. L., Meagher, M. M. and Reilly, P. J. (1989) *Biotechnol. Bioeng.*, 34, 694–704.

Pantoiiano, M. w., Whitlow, M., Wood, J. F., Dodd, S.w., Hardman, K. D., Rollence, M. L. and Bryan, P. N. (1989) *Biochemistry*, 28, 7205–7213.

Pazur, J. H. and Okada, S. (1967) *Carbohydr. Res.*, 4, 371–379.

Pazur, J. H., Cepure, a., Okada, S. and Forsberg, L. S. (1977) *Carbohydr. Res.*, 58, 193–202.

Russell, A. J. and Fersht, A. R. (1987) *Nature*, 328, 496–500.

Scrutton, N. S., Berry, A. and Perham, R. N. (1990) *Nature*, 343, 38–43.

Sierks, M. R. and Svensson, B. (1994) *Protein Eng.*, 7, 1479–1484.

Sierks, M. R., Ford, C., Reilly, P. J. and Svensson, B. (1989) *Protein Eng.*, 2, 621–625.

Stoffer, B. B., Dupont, C., Frandsen, T. P., Lehmbeck, J. and Svensson, B. (1997) *Protein Eng.*, 10, 81–87.

Svensson, B., Frandsen, T. P., Matsui, I., Juge, N., Fierobe, H.-P., Stoffer, B. and Rodenburg, K. W. (1995) *Carbohydrate Bioengineering*, Petersen, S. B., Svensson, B. and Pedersen, S., eds., Elsevier, Amsterdam, pp. 125–145.

Teague, W. M. and Brumm, P. J. (1992) *Starch Hydrolysis Products: Woldwide Technology, Production, and Applications*, Schenck, F. W. and Hebeda, R. e., eds., VCH, New York, pp. 45–77.

Watanabe, T., Kawamura, S., Sasaki, S. and Matsuda, K. (1969a) *Stärke*, 21, 18–21.

Watanabe, T., Kawamura, S., Sasaki, S. and Matsuda, K. (1969b) Stärke, 21, 44–47.

Wells, J. a., Cunningham, B. C., Graycar, T. P. and Estell, D. a. (1987a) *Proc. Natl. Acad. Sci. U.S.A.*, 84, 1219–1223.

Ackers, G. K. and Smith, F. R. (1985) *Annu. Rev. Biochem.*, 54, 597–629.

Aleshin, A., Golubev, A., Firsov, L. M. and Honzatko, R. B. (1992) *J. Biol. Chem.*, 267, 19291–19298.

Aleshin, A. E., Firsov, L. M. and Honzatko, R. B. (1994) *J. Biol. Chem.*, 269, 15631–15639.

Allen, M., Coutinho, P. M. and Ford, C. (1998) *Protein Eng.*, accepted for publication.

Balaji, V. N., Mobasser, A. and Rao, S. N. (1989) *Biochem. Biophys. Res. Commun.*, 160, 109–114.

Carter, P. J., Winter, G., Wilkinson, A. J. and Fersht, A. R. (1984) *Cell*, 38, 835–840.

Carter, P., Nilsson, B., Burnier, J. P., Burdick, D. and Wells, J. A. (1989) *Proteins: Struct. Funct. Genet.*, 6, 240–248.

Chen, H.-M., Ford, C. and Reilly, P. J. (1994) *Biochem. J.*, 30, 275–281.

Chen, H.-M., Li, Y., Panda, T., Buehler, F. U., Ford, C. and Reilly, P. J. (1996) *Protein Eng.*, 9, 499–505.

Corn Annual (1998) Corn Refiners Association, Inc., Washington, D.C.

Coutinho, P. M. (1996).Ph.D. Dissertation, Iowa State. University, Ames, Iowa.

Coutinho, P. M. and Reilly, P. J. (1994a) *Protein Eng.*, 7, 393–400.

Coutinho, P. M. and Reilly, P. J. (1994b) *Protein Eng.*, 7, 749–760.

Coutinho, P. M. and Reilly, P. J. (1997) *Proteins: Struct. Funct Genet.*, 29, 334–347.

Cunningham, B. C. and Wells, J. A. (1987) *Protein Eng.*, 1, 319–325.
Fang, T.-Y. and Ford, C. (1998) *Protein Eng.*, 11, 383–388.
Fang, T.-Y., Coutinho, P. M., Reilly, P. J. and Ford, C. (1998a) *Protein Eng.*, 11, 119–126.
Fang, T.-Y., Honzatko, R. B., Reilly, P. J. and Ford, C. (1998b) *Protein Eng.*, 11, 127–133.
Fierobe, H.-P., Stoffer, B. B., Frandsen, T. P. and Svensson, B. (1996) *Biochemistry*, 35, 8696–8704.
Frandsen, T. P., Christensen, T., Stoffer, B. Lehmbeck, J., Dupont, C., Honzatko, R. B. and Svensson, B. (1995) *Biochemitry*, 34, 10162–10169.
Frandsen, T. P., Stoffer, B., Palcic, M. M., Hof, S. and Svensson, B. (1996) *J. Mol. Biol.*, 263, 79–89.
Hecht, M. H., Sturtevant, J. M. and Sauer, R. t. (1986) *Proteins: Struct. Funct. Genet.*, 1, 43–46.
Hehre, E. J., Okada, G. and Genghof, D. S. (1969) *Arch. Biochem. Biophys.*, 135, 74–89.
Hiromi, K., Takahashi, K., Hamauzu, Z. and Ono, S. (1966a) *J. Biochem.*, 59, 469–475.
Hiromi, K., Kawai, M. and Ono, S. (1966b) *J. Biochem.*, 59, 476–480.
Li, Y., Reilly, P. J. and Ford, C. (1997) *Protein Eng.*, 10, 1199–1204.
Li, Y., Coutinho, P. M. and Ford, C. (1998) *Protein Eng.*, accepted for publication.
Liao, H., McKenzie, T. and Hageman, R. (1986) *Proc. Natl. Acad Sci. U.S.A.*, 83, 576–580.
Liu, H.-L., Coutinho, P. M., Ford, C. and Reilly, P. J. (1998) *Protein Eng.*, 11, 389–398.
Matsumura, M., Signor, G. and Matthews, B. W. (1989) *Nature*, 342, 291–294.
Meagher, M. M. and Reilly, P. J. (1989) *Biotechnol. Bioeng.*, 34, 689–693.
Natarajan, S. and Sierks, M. R. (1996) *Biochemistry*, 35, 15269–15279.
Nikolov, Z. L. and Reilly, P. J. (1991) *Biocatalysts for Industry*, Dordick, J. S., ed., Plenum, New York, pp. 37–62.
Nikolov, Z. L., Meagher, M. M. and Reilly, P. J. (1989) *Biotechnol. Bioeng.*, 34, 694–704.
Pantoiiano, M. w., Whitlow, M., Wood, J. F., Dodd, S. w., Hardman, K. D., Rollence, M. L. and Bryan, P. N. (1989) *Biochemistry*, 28, 7205–7213.
Pazur, J. H. and Okada, S. (1967) *Carbohydr. Res.*, 4, 371–379.
Pazur, J. H., Cepure, a., Okada, S. and Forsberg, L. S. (1977) *Carbohydr. Res.*, 58, 193–202.
Russell, A. J. and Fersht, A. R. (1987) *Nature*, 328, 496–500.
Scrutton, N. S., Berry, A. and Perham, R. N. (1990) *Nature*, 343, 38–43.
Sierks, M. R. and Svensson, B. (1994) *Protein Eng.*, 7, 1479–1484.
Sierks, M. R., Ford, C., Reilly, P. J. and Svensson, B. (1989) *Protein Eng.*, 2, 621–625.
Stoffer, B. B., Dupont, C., Frandsen, T. P., Lehmbeck, J. and Svensson, B. (1997), *Protein Eng.*, 10, 81–87.
Svensson, B., Frandsen, T. P., Matsui, I., Juge, N., Fierobe, H.-P., Stoffer, B. and Rodenburg, K. W. (1995) *Carbohydrate Bioengineering*, Petersen, S. B., Svensson, B. and Pedersen, S., eds., Elsevier, Amsterdam, pp. 125–145.
Teague, W. M. and Brumm, P. J. (1992) Starch Hydrolysis Products: *Woldwide Technology Production, and Applications*, Schenck, F. W. and Hebeda, R. e., eds., VCH, New York, pp. 45–77.
Watanabe, T., Kawamura, S., Sasaki, S. and Matsuda, K. (1969a) Stärke, 21, 18–21.
Watanabe, T., Kawamura, S., Sasaki, S. and Matsuda, K. (1969b) Stärke, 21, 44–47.
Wells, J. a., Cunningham, B. C., Graycar, T. P. and Estell, D. a. (1987a) *Proc. Natl. Acad. Sci. U.S.A.*, 84, 1219
Kraulis, P. J. (1991) *J. Appl. Crystallogr.* 34, 946–950
Li, Y. (1996) Genetic construction and biochemical analysis of thermostability mutants of glucoamylase from *Aspergillus awamari*, Ph.d. Dissertation. Iowa State University
O'Rourke, T., Bentley, I. S. and Williams, E. C. (1996) Godfrey, T. and West, S. (eds). *Industrial Enzymology*, Second edition. Stockton Press, New York
Przybyt, M. and Sugier, H. (1988) Starch/Starke, 40, 171–174
Ramachandran, G. N., Ramakrishnan, C. and Sasisekharan, V. (1963) *J. Mol. Biol.*, 7, 95–99
Shein, C. H. (1990) *Bio/Technology*, 8, 308–317
Schimmel, P. R. and Flory, P. J. (1968) *J. Mol. Biol.*, 34, 105–120.
Sinitsyn, A. P., Klibanov, A. M., Klesov, A. A. and Martiek, K. (1978) *Prikl, Biokhim. Mikrobiol.*, 14, 236–243.

---

What is claimed is:

1. A fungal glucoamylase including a mutation of pair Asn20Cys coupled with Ala27Cys forming a disulfide bond between the two stabilizing members wherein the fungal glucoamylase is Aspergillus glucoamylase.

2. The glucoamylase as set forth in claim 1 wherein the mutation provides increased thermal stability and reduced isomaltose formation.

3. The fungal glucoamylase as set forth in claim 1 further including at least one mutation selected from Table 13 wherein cumulative thermal stability is provided by the additional mutations.

4. The fungal glucoamylase as set forth in claim 1 further including mutations Ser30Pro, and Gly137Ala wherein cumulative thermal stability is provided by the additional mutations.

5. The fungal glucoamylase as set forth in claim 1 further including at least one mutation from Table 14 wherein cumulative reduced isomaltose formation is provided by the additional mutations.

6. The fungal glucoamylase as set forth in claim 1 further including a 311-314 Loop mutation wherein cumulative reduced isomaltose formation is provided by the mutation.

7. A fungal glucoamylase including a Ser411Ala mutation and a mutation pair Asn20Cys coupled with Ala27Cys forming a disulfide bond between the two members of the pair wherein the fungal glucoamylase is Aspergillus glucoamylase.

8. The glucoamylase as set forth in claim 7 wherein increased thermal stability, increased pH optimum and reduced isomaltose formation are provided by the mutations.

9. A fungal glucoamylase including a Ser411Ala mutation and a mutation pair Asn20Cys coupled with Ala27Cys forming a disulfide bond between the two members of the pair and a 311-314 Loop mutation wherein the fungal glucoamylase is Aspergillus glucoamylase.

10. The glucoamylase as set forth in claim 9 wherein increased thermal stability, increased pH optimum and reduced isomaltose formation are provided by the mutations.

* * * * *